United States Patent
Suthanthiran et al.

(10) Patent No.: US 9,758,828 B2
(45) Date of Patent: Sep. 12, 2017

(54) METHODS TO DETECT, TREAT AND PREVENT ACUTE CELLULAR REJECTION IN KIDNEY ALLOGRAFTS

(71) Applicants: Manikkam Suthanthiran, Scarsdale, NY (US); Ruchuang Ding, Beechurst, NY (US); Joseph E. Schwartz, East Setauket, NY (US); Abraham Shaked, Wynnewood, PA (US)

(72) Inventors: Manikkam Suthanthiran, Scarsdale, NY (US); Ruchuang Ding, Beechurst, NY (US); Joseph E. Schwartz, East Setauket, NY (US); Abraham Shaked, Wynnewood, PA (US)

(73) Assignees: Cornell University, Ithaca, NY (US); The Trustees of the University of Pennsylvania, Philadelphia, PA (US)

( * ) Notice: Subject to any disclaimer, the term of this patent is extended or adjusted under 35 U.S.C. 154(b) by 186 days.

(21) Appl. No.: 14/170,132

(22) Filed: Jan. 31, 2014

(65) Prior Publication Data
US 2014/0213533 A1    Jul. 31, 2014

Related U.S. Application Data

(60) Provisional application No. 61/758,887, filed on Jan. 31, 2013.

(51) Int. Cl.
| | |
|---|---|
| G01N 33/48 | (2006.01) |
| G01N 31/00 | (2006.01) |
| G06G 7/48 | (2006.01) |
| G06G 7/58 | (2006.01) |
| C12Q 1/68 | (2006.01) |
| A61K 31/365 | (2006.01) |
| A61K 31/56 | (2006.01) |

(Continued)

(52) U.S. Cl.
CPC .......... *C12Q 1/6883* (2013.01); *A61K 31/365* (2013.01); *A61K 31/436* (2013.01); *A61K 31/52* (2013.01); *A61K 31/56* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,187,534 B1 | 2/2001 | Strom |
| 6,900,015 B2 | 5/2005 | Avihingsanon et al. |

(Continued)

FOREIGN PATENT DOCUMENTS

| | | |
|---|---|---|
| EP | 0534858 A1 | 3/1993 |
| WO | WO-2011112719 A1 | 9/2011 |

OTHER PUBLICATIONS

"U.S. Appl. No. 13/583,750, Non Final Office Action mailed Jul. 9, 2015", 18 pgs.

(Continued)

*Primary Examiner* — Larry D Riggs, II
(74) *Attorney, Agent, or Firm* — Schwegman Lundberg & Woessner, P.A.

(57) ABSTRACT

Methods for prevention and treatment of kidney transplant rejection are described that involve determination, analysis and computation of a 3-gene molecular signature of levels of specific RNAs (IP-10 mRNA, CD3ε mRNA, and 18S rRNA) in urinary sample cells. The methods and devices described herein are diagnostic and prognostic of acute cellular rejection in kidney allografts.

17 Claims, 13 Drawing Sheets

(51) Int. Cl.
A61K 31/436 (2006.01)
A61K 31/52 (2006.01)

(56) References Cited

U.S. PATENT DOCUMENTS

| | | | |
|---|---|---|---|
| 2003/0113744 A1 | 6/2003 | O'Toole et al. | |
| 2004/0053284 A1 | 3/2004 | Andrus et al. | |
| 2006/0088836 A1 | 4/2006 | Wohlgemuth | |
| 2007/0031890 A1 | 2/2007 | Wohlgemuth | |
| 2008/0131441 A1 | 6/2008 | Suthanthiran | |
| 2013/0012860 A1 | 1/2013 | Suthanthiran et al. | |
| 2015/0191787 A1 | 7/2015 | Muthukumar et al. | |

OTHER PUBLICATIONS

Veronese, F., et al., "Pathological and Clinical Correlates of FOXP3+ Cells in Renal Allografts during Acute Rejection", American Journal of Transplantation; 7(4), (2007), 914-922.
"U.S. Appl. No. 13/583,750, Preliminary Amendment filed Sep. 10, 2012", 3 pgs.
"U.S. Appl. No. 13/583,750, Restriction Requirement mailed Nov. 12, 2013", 9 pgs.
"International Application Serial No. PCT/US11/27754, International Preliminary Report on Patentability dated Sep. 11, 2012", 6 pgs.
"International Application Serial No. PCT/US11/27754, International Search Report mailed May 18, 2011", 3 pgs.
"International Application Serial No. PCT/US11/27754, Written Opinion mailed May 18, 2011", 5 pgs.
Afaneh, C., et al., "Urinary Cell Levels of mRNA for OX40, OX40L, PD-1, PD-L1 or PD-L2 and Acute Rejection of Human Renal Allografts", Transplantation, 90(12), (2010), 14 pgs.
Anglicheau, D., et al., "Noninvasive Prediction of Organ Graft Rejection and Outcome Using Gene Expression Patterns", Transplantation, 86(2), (2008), 15 pgs.
Dadhania, D., et al., "Molecular signatures of urinary cells distinguish acute rejection of renal allografts from urinary tract infection", (Abstract Only), Transplantation, 75(10), 1752-1754, (2003), 1 pg.
Ding, R., et al., "CD102 mRNA Levels in Urinary Cells Predict Acute Rejection of Renal Allografts", Transplantation, 75(8), (2003), 1307-1312.
Ding, R., et al., "Noninvasive Diagnosis of BK Virus Nephritis by Measurement of Messenger RNA for BK Virus VP1 in Urine", Transplantation, 74(7), (2002), 987-994.
Gibson, U. E. M., et al., "A Novel Method for Real Time Quantitative RT-PCR", Genome Research, 6, (1996), 995-1001.
Heid, C. A., et al., "Real Time Quantitative PCR", Genome Research, 6, (1996), 986-994.
Hsieh, M. F, "", J Immunol 2006; 177, 1855-1863.
Li, B., et al., "Noninvasive Diagnosis of Renal-Allograft Rejection by Measurement of Messenger RNA for Perforin and Granzyme B in Urine", The New England Journal of Medicine, 344(13), (2001), 947-954.
Muthukumar, T., et al., "Messenger RNA for FOXP3 in the Urine of Renal-Allograft Receipients", New England Journal of Medicine, 353(22), (2005), 2342-2351.
Muthukumar, T., et al., "Serine Proteinase Inhibitor-9, an Endogenous Blocker of Granzyme B/Perforin Lytic Pathway, is Hyperexpressed During Acute Rejection of Renal Allografts", Transplantation, 75(9), (2003), 1565-1570.
Prashar, Y., et al., "Analysis of differential gene expression by display of 3' end restriction fragments of cDNA's", Proc. Natl. Acad. Sci. USA, 93, (Jan. 1996), 659-663.
Tatapudi, R. R., et al., "Noninvasive detection of renal allograft inflammation by measurements of mRNA for IP-10 and CXCR3 in urine", Kidney International, 65(6), (2004), 2390-2397.
Tyagi, S., et al., "Beacons of Light", Nature Biotechnology, 24(3), (1996), 303-304.
Velculescu, V. E., et al., "Serial Analysis of Gene Expression", Science, 270(5235), (1995), 484-487.
Zhang, Z., et al., "A Linear Regression Framework for Receiver Operating Characteristics (ROC) Curve Analysis", University of Washington Biostatistics Working Paper Series, (2005), 23 pgs.
U.S. Appl. No. 14/591,542, filed Jan. 7, 2015, Urine MRNA Profile and Acute Dysfunction of Kidney Allograft.
U.S. Appl. No. 13/583,750, filed Sep. 10, 2012, Methods and Compositions to Predict and Detect Acute Rejection.
"U.S. Appl. No. 13/583,750, Final Office Action mailed Jul. 30, 2014", 17 pgs.
"U.S. Appl. No. 13/583,750, Non Final Office Action mailed Mar. 3, 2014", 14 pgs.
"U.S. Appl. No. 13/583,750, Response filed Feb. 12, 2014 to Restriction Requirement mailed Nov. 12, 2013", 8 pgs.
"U.S. Appl. No. 13/583,750, Response filed Jul. 1, 2014 to Non Final Office Action mailed Mar. 3, 2014", 13 pgs.
"U.S. Appl. No. 13/583,750, Response filed Oct. 30, 2014 to Final Office action mailed Jul. 30, 2014", 13 pgs.
Aquino-Dias, E. C., et al., "Non-invasive diagnosis of acute rejection in kidney transplants with delayed graft function", Kidney International 73(7), (2008), 877-884.
Chen, G., et al., "Discordant Protein and mRNA Expression in Lung Adenocarcinomas", Molecular & Cellular Proteomics 1(4), (2002), 304-313.
Cheung, V. G., et al., "Natural variation in human gene expression assessed in lymphoblastoid cells", Nature Genetics, 33(3), (Mar. 2003), 422-425.
Cobb, J P, et al., "Sepsis gene expression profiling: Murine splenic compared with hepatic responses determined by using complementary DNA microarrays", Crit Care Med, 30(12), (2002), 2711-2721.
Flechner, S. M., et al., "Kidney Transplant Rejection and Tissue Injury by Gene Profiling of Biopsies and Peripheral Blood Lymphocytes", American Journal of Transplantation, 4(9), (2004), 1475-1489.
Hoshikawa, Y., et al., "Hypoxia induces different genes in the lungs of rats compared with mice", Physiol Genomics, 12(3), (2003), 209-219.
Kotsch, K., et al., "Enhanced granulysin mrna expression in urinary sediment in early and delayed acute renal allograft rejection", Transplantation, 77(12), (2004), 1866-1875.
"U.S. Appl. No. 13/583,750, Examiner Interview Summary mailed Oct. 10, 2014", 3 pgs.
"U.S. Appl. No. 13/583,750, Examiner Interview Summary mailed Nov. 12, 2015", 3 pgs.
"U.S. Appl. No. 13/583,750, Final Office Action mailed Jan. 25, 2016", 15 pgs.
"U.S. Appl. No. 13/583,750, Response filed Apr. 22, 2016 to Final Office Action mailed Jan. 25, 2016", 16 pgs.
"U.S. Appl. No. 13/583,750, Response filed Nov. 9, 2015 to Non Final Office Action mailed Jul. 9, 2015", 16 pgs.
Simon, T, et al., "American Journal of Transplantation", (2003), 1121-1127.
Simon, T, et al., "Transplantation", vol. 77, No. 10, (May 27, 2004), 1589-1595.
"U.S. Appl. No. 13/583,750, Advisory Action mailed May 11, 2016", 4 pgs.
"U.S. Appl. No. 13/583,750, Response filed May 18, 2016 to Final Office Action mailed Jan. 25, 2016", 17 pgs.
"U.S. Appl. No. 14/591,542, Response filed Jul. 27, 2016 to Restriction Requirement mailed Apr. 27, 2016", 8 pgs.
"U.S. Appl. No. 14/591,542, Restriction Requirement mailed Apr. 27, 2016", 8 pgs.
"U.S. Appl. No. 14/592,537, Non Final Office Action mailed Sep. 15, 2016", 22 pgs.
Anglicheau, D, et al., "", Transplantation & vol. 93, No. 11, (Jun. 15, 2012), 1136-1146.
Bolstad, B M, et al., "", Bioinformatics, (2003), 185-193.
Docherty, N G, et al., "Nephrol Dial Transplant", (2006), 2106-2119.
Dressing, M C, et al., "", Nephrol Dial Transplant, (2010), 4087-4092.
Matignon, M, et al., "", J Am Soc Nephrol 25, (2014), 1-12.

SEQUENCE LISTING

<160> NUMBER OF SEQ ID NOS: 33

<210> SEQ ID NO 1
<211> LENGTH: 2235
<212> TYPE: DNA
<213> ORGANISM: Homo sapiens
<220> FEATURE:
<221> NAME/KEY: misc_feature
<222> LOCATION: (1)...(2235)
<223> OTHER INFORMATION: n = A,T,C or G

<400> SEQUENCE: 1

| | | | | | |
|---|---|---|---|---|---|
| cgctgctcct | cccgtcgccg | tccgggcccg | tccgtccgtc | cgtccgtcgt | cctcctcgct | 60 |
| nnnncggggc | gccgggcccg | tcctcacngg | ccccccgnnnn | ngtccnggcc | cgtcggggcc | 120 |
| tcgccgcgct | ctaccttacc | tacctggttg | atcctgccag | tagcatatgc | ttgtctcaaa | 180 |
| gattaagcca | tgcatgtcta | agtacgcacg | gccggtacag | tgaaactgcg | aatggctcat | 240 |
| taaatcagtt | atggttcctt | tggtcgctcg | ctcctctcct | acttggataa | ctgtggtaat | 300 |
| tctagagcta | atacatgccg | acgggcgctg | accccttcg | cgggggggat | gcgtgcattt | 360 |
| atcagatcaa | aaccaacccg | gtcagcccct | ctccggcccc | ggccgggggg | cgggcgccgg | 420 |
| cggctttggt | gactctagat | aacctcgggc | cgatcgcacg | ccccccgtgg | cggcgacgac | 480 |
| ccattcgaac | gtctgcccta | tcaactttcg | atggtagtcg | ccgtgcctac | catggtgacc | 540 |
| acgggtgacg | gggaatcagg | gttcgattcc | ggagagggag | cctgagaaac | ggctaccaca | 600 |
| tccaaggaag | gcagcaggcg | cgcaaattac | ccactcccga | cccggggagg | tagtgacgaa | 660 |
| aaataacaat | acaggactct | ttcgaggccc | tgtaattgga | atgagtccac | tttaaatcct | 720 |
| ttaacgagga | tccattggag | ggcaagtctg | gtgccagcag | ccgcggtaat | tccagctcca | 780 |
| atagcgtata | ttaaagttgc | tgcagttaaa | aagctcgtag | ttggatcttg | ggagcgggcg | 840 |
| ggcggtccgc | cgcgaggcga | gccaccgccc | gtccccgccc | cttgcctctc | ggcgccccct | 900 |
| cgatgctctt | agctgagtgt | cccgcgggc | ccgaagcgtt | tactttgaaa | aaattagagt | 960 |
| gttcaaagca | ggcccgagcc | gcctggatac | cgcagctagg | aataatggaa | taggaccgcg | 1020 |
| gttctatttt | gttggttttc | ggaactgagg | ccatgattaa | gagggacggc | cggggcatt | 1080 |
| cgtattgcgc | cgctagaggt | gaaattcctt | ggaccggcgc | aagacggacc | agagcgaaag | 1140 |
| catttgccaa | gaatgttttc | attaatcaag | aacgaaagtc | ggaggttcga | agacgatcag | 1200 |
| ataccgtcgt | agttccgacc | ataaacgatg | ccgaccggcg | atgcggcggc | gttattccca | 1260 |
| tgacccgccg | ggcagcttcc | gggaaaccaa | agtctttggg | ttccgggggg | agtatggttg | 1320 |
| caaagctgaa | acttaaagga | attgacgaa | gggcaccacc | aggagtggag | cctgcggctt | 1380 |
| aatttgactc | aacacgggaa | acctcacccg | gcccggacac | ggacaggatt | gacagattga | 1440 |
| tagctctttc | tcgattccgt | gggtggtggt | gcatggccgt | tcttagttgg | tggagcgatt | 1500 |
| tgtctggtta | attccgataa | cgaacgagac | tctggcatgc | taactagtta | cgcgaccccc | 1560 |
| gagcggtcgg | cgtcccccaa | cttcttagag | ggacaagtgg | cgttcagcca | cccgagattg | 1620 |
| agcaataaca | ggtctgtgat | gcccttagat | gtccggggct | gcacgcgcgc | tacactgact | 1680 |
| ggctcagcgt | gtgcctaccc | tacgccggca | ggcgcgggta | accgttgaa | ccccattcgt | 1740 |
| gatgggatc | ggggattgca | attattcccc | atgaacgagg | aattcccagt | aagtgcgggt | 1800 |
| cataagcttg | cgttgattaa | gtccctgccc | tttgtacaca | ccgcccgtcg | ctactaccga | 1860 |
| ttggatggtt | tagtgaggcc | ctcggatcgg | ccccgccggg | gtcggccac | ggccctggcg | 1920 |
| gagcgctgag | aagacggtcg | aacttgacta | tctagaggaa | gtaaaagtcg | taacaaggtt | 1980 |

```
tccgtaggtg aacctgcgga aggatcatta acggagcccg gacggcggcc cgcggcggcg    2040
ccgcgccgcg cttccctccg cacacccacc ccccaccgc gacggcgcgt gcgggcgggg    2100
ccgtgcccgt tcgttcgctc gctcgttcgt tcgccgcccg gcccggccgc gagagccgag    2160
aactcgggag ggagacgggg gagagagaga gagagagaga gagagagaga gagagagaga    2220
gaaagaaggg cgtgt                                                    2235
```

<210> SEQ ID NO 2  
<211> LENGTH: 1534  
<212> TYPE: DNA  
<213> ORGANISM: Homo sapiens

<400> SEQUENCE: 2

```
tattgtcaga gtcctcttgt ttggccttct aggaaggctg tgggacccag ctttcttcaa      60
ccagtccagg tggaggcctc tgccttgaac gtttccaagt gaggtaaaac ccgcaggccc     120
agaggcctct ctacttcctg tgtggggttc agaaaccctc ctcccctccc agcctcaggt     180
gcctgcttca gaaaatgaag tagtaagtct gctggcctcc gccatcttag taaagtaaca     240
gtcccatgaa acaaagatgc agtcgggcac tcactggaga gttctgggcc tctgcctctt     300
atcagttggc gtttggggc aagatggtaa tgaagaaatg ggtggtatta cacagacacc      360
atataaagtc tccatctctg gaaccacagt aatattgaca tgccctcagt atcctggatc     420
tgaaatacta tggcaacaca atgataaaaa cataggcggt gatgaggatg ataaaaacat     480
aggcagtgat gaggatcacc tgtcactgaa ggaattttca gaattggagc aaagtggtta     540
ttatgtctgc taccccagag gaagcaaacc agaagatgcg aacttttatc tctacctgag     600
ggcaagagtg tgtgagaact gcatggagat ggatgtgatg tcggtggcca caattgtcat     660
agtggacatc tgcatcactg ggggcttgct gctgctggtt tactactgga gcaagaatag     720
aaaggccaag gccaagcctg tgacacgagg agcgggtgct ggcggcaggc aaaggggaca     780
aaacaaggag aggccaccac ctgttcccaa cccagactat gagcccatcc ggaaaggcca     840
gcgggacctg tattctggcc tgaatcagag acgcatctga ccctctggag aacactgcct     900
cccgctggcc caggtctcct ctccagtccc cctgcgactc cctgtttcct gggctagtct     960
tggaccccac gagagagaat cgttcctcag cctcatggtg aactcgcgcc ctccagcctg    1020
atcccccgct ccctcctccc tgccttctct gctggtaccc agtcctaaaa tattgctgct    1080
tcctcttcct ttgaagcatc atcagtagtc acaccctcac agctggcctg ccctcttgcc    1140
aggatattta tttgtgctat tcactccctt ccctttggat gtaacttctc cgttcagttc    1200
cctccttttc ttgcatgtaa gttgtccccc atcccaaagt attccatcta cttttctatc    1260
gccgtcccct tttgcagccc tctctgggga tggactgggg aaatgttgac agaggccctg    1320
ccccgttcac agatcctggc cctgagccag ccctgtgctc ctccctcccc caacactccc    1380
taccaacccc ctaatcccct actccctcca ccccccctcc actgtaggcc actggatggt    1440
catttgcatc tccgtaaatg tgctctgctc ctcagctgag agagaaaaaa ataaactgta    1500
tttggctgca agaaaaaaaa aaaaaaaaa aaaa                                 1534
```

<210> SEQ ID NO 3  
<211> LENGTH: 1172  
<212> TYPE: DNA  
<213> ORGANISM: Homo sapiens

<400> SEQUENCE: 3

```
gagacattcc tcaattgctt agacatattc tgagcctaca gcagaggaac ctccagtctc      60
agcaccatga atcaaactgc gattctgatt tgctgcctta tctttctgac tctaagtggc     120
attcaaggag tacctctctc tagaaccgta cgctgtacct gcatcagcat tagtaatcaa     180
cctgttaatc caaggtcttt agaaaaactt gaaattattc ctgcaagcca attttgtcca     240
cgtgttgaga tcattgctac aatgaaaaag aagggtgaga agagatgtct gaatccagaa     300
tcgaaggcca tcaagaattt actgaaagca gttagcaagg aaatgtctaa agatctcct      360 taaaaccaga ggggagcaaa atcgatgcag tgcttccaag gatggaccac acagaggctg     420
cctctcccat cacttcccta catggagtat atgtcaagcc ataattgttc ttagtttgca     480
gttacactaa aaggtgacca atgatggtca ccaaatcagc tgctactact cctgtaggaa     540
ggttaatgtt catcatccta agctattcag taataactct accctggcac tataatgtaa     600
gctctactga ggtgctatgt tcttagtgga tgttctgacc ctgcttcaaa tatttccctc     660
acctttccca tcttccaagg gtactaagga atctttctgc tttggggttt atcagaattc     720
tcagaatctc aaataactaa aaggtatgca atcaaatctg cttttttaaag aatgctcttt    780 acttcatgga cttccactgc catcctccca aggggcccaa attctttcag tggctaccta    840
catacaattc caaacacata caggaaggta gaaatatctg aaaatgtatg tgtaagtatt    900
cttatttaat gaaagactgt acaaagtata agtcttagat gtatatattt cctatattgt    960
tttcagtgta catggaataa catgtaatta agtactatgt atcaatgagt aacaggaaaa   1020
ttttaaaaat acagatagat atatgctctg catgttacat aagataaatg tgctgaatgg   1080
ttttcaaata aaaatgaggt actctcctgg aaatattaag aaagactatc taaatgttga   1140
aagatcaaaa ggttaataaa gtaattataa ct                                  1172
```

```
<210> SEQ ID NO 4
<211> LENGTH: 26
<212> TYPE: DNA
<213> ORGANISM: Homo sapiens

<400> SEQUENCE: 4
aagaaatggg tggtattaca cagaca                                          26

<210> SEQ ID NO 5
<211> LENGTH: 25
<212> TYPE: DNA
<213> ORGANISM: Homo sapiens

<400> SEQUENCE: 5
tgccatagta tttcagatcc aggat                                           25

<210> SEQ ID NO 6
<211> LENGTH: 33
<212> TYPE: DNA
<213> ORGANISM: Homo sapiens

<400> SEQUENCE: 6
ccatctctgg aaccacagta atattgacat gcc                                  33

<210> SEQ ID NO 7
<211> LENGTH: 23
<212> TYPE: DNA
<213> ORGANISM: Homo sapiens

<400> SEQUENCE: 7
ggaccagtac agcttcagca ctg                                             23
```

<210> SEQ ID NO 8
<211> LENGTH: 20
<212> TYPE: DNA
<213> ORGANISM: Homo sapiens

<400> SEQUENCE: 8
gccctcttga agtcagggtg                                                   20

<210> SEQ ID NO 9
<211> LENGTH: 30
<212> TYPE: DNA
<213> ORGANISM: Homo sapiens

<400> SEQUENCE: 9
tgccgcttct acagtttcca tgtggtacac                                        30

<210> SEQ ID NO 10
<211> LENGTH: 24
<212> TYPE: DNA
<213> ORGANISM: Homo sapiens

<400> SEQUENCE: 10
gcgaatctga cttacgccat tatt                                              24

<210> SEQ ID NO 11
<211> LENGTH: 20
<212> TYPE: DNA
<213> ORGANISM: Homo sapiens

<400> SEQUENCE: 11
caagagggcc tccagagtcc                                                   20

<210> SEQ ID NO 12
<211> LENGTH: 27
<212> TYPE: DNA
<213> ORGANISM: Homo sapiens

<400> SEQUENCE: 12
cccacgcaca actcaatggt actgtcg                                           27

<210> SEQ ID NO 13
<211> LENGTH: 22
<212> TYPE: DNA
<213> ORGANISM: Homo sapiens

<400> SEQUENCE: 13
tgtccacgtg ttgagatcat tg                                                22

<210> SEQ ID NO 14
<211> LENGTH: 20
<212> TYPE: DNA
<213> ORGANISM: Homo sapiens

<400> SEQUENCE: 14
ggccttcgat tctggattca                                                   20

<210> SEQ ID NO 15
<211> LENGTH: 24
<212> TYPE: DNA
<213> ORGANISM: Homo sapiens

<400> SEQUENCE: 15
tacaatgaaa aagaagggtg agaa                                          24

<210> SEQ ID NO 16
<211> LENGTH: 18
<212> TYPE: DNA
<213> ORGANISM: Homo sapiens

<400> SEQUENCE: 16
acccagcagc cagagcac                                                 18

<210> SEQ ID NO 17
<211> LENGTH: 20
<212> TYPE: DNA
<213> ORGANISM: Homo sapiens

<400> SEQUENCE: 17
caacctcggc gtcatttagc                                               20

<210> SEQ ID NO 18
<211> LENGTH: 28
<212> TYPE: DNA
<213> ORGANISM: Homo sapiens

<400> SEQUENCE: 18
cttggtggtc actcacctca aggaccat                                      28

<210> SEQ ID NO 19
<211> LENGTH: 19
<212> TYPE: DNA
<213> ORGANISM: Homo sapiens

<400> SEQUENCE: 19
cgtgctcagc tcccttctg                                                19

<210> SEQ ID NO 20
<211> LENGTH: 21
<212> TYPE: DNA
<213> ORGANISM: Homo sapiens

<400> SEQUENCE: 20
cctggtgtcc tcttggttct g                                             21

<210> SEQ ID NO 21
<211> LENGTH: 27
<212> TYPE: DNA
<213> ORGANISM: Homo sapiens

<400> SEQUENCE: 21
accaagaccc cagcaccaac catacct                                       27

<210> SEQ ID NO 22
<211> LENGTH: 20
<212> TYPE: DNA
<213> ORGANISM: Homo sapiens

<400> SEQUENCE: 22
gcgtgctaat ggtggaaacc                                               20

<210> SEQ ID NO 23
<211> LENGTH: 22
<212> TYPE: DNA
<213> ORGANISM: Homo sapiens

<400> SEQUENCE: 23
cggagctctg atgtgttgaa ga                                                  22

<210> SEQ ID NO 24
<211> LENGTH: 37
<212> TYPE: DNA
<213> ORGANISM: Homo sapiens

<400> SEQUENCE: 24
acaacgaaat ctatgacaag ttcaagcaga gtacaca                                  37

<210> SEQ ID NO 25
<211> LENGTH: 22
<212> TYPE: DNA
<213> ORGANISM: Homo sapiens

<400> SEQUENCE: 25
tcaacacctg ggtctcaaaa aa                                                  22

<210> SEQ ID NO 26
<211> LENGTH: 20
<212> TYPE: DNA
<213> ORGANISM: Homo sapiens

<400> SEQUENCE: 26
cagcctggtt tctgcatcaa                                                     20

<210> SEQ ID NO 27
<211> LENGTH: 32
<212> TYPE: DNA
<213> ORGANISM: Homo sapiens

<400> SEQUENCE: 27
agctacccgg caacaactct tcaattttac ct                                       32

<210> SEQ ID NO 28
<211> LENGTH: 20
<212> TYPE: DNA
<213> ORGANISM: Homo sapiens

<400> SEQUENCE: 28
gcccgaagcg tttactttga                                                     20

<210> SEQ ID NO 29
<211> LENGTH: 24
<212> TYPE: DNA
<213> ORGANISM: Homo sapiens

<400> SEQUENCE: 29
tccattattc ctagctgcgg tatc                                                24

<210> SEQ ID NO 30
<211> LENGTH: 19
<212> TYPE: DNA
<213> ORGANISM: Homo sapiens

<400> SEQUENCE: 30
aaagcaggcc cgagccgcc                                                      19

<210> SEQ ID NO 31
<211> LENGTH: 21
<212> TYPE: DNA
<213> ORGANISM: Mus musculus

```
<400> SEQUENCE: 31
cccacatctg gagcagagtc a                                             21

<210> SEQ ID NO 32
<211> LENGTH: 23
<212> TYPE: DNA
<213> ORGANISM: Mus musculus

<400> SEQUENCE: 32
cagatgccat ttttcaggtc ttg                                           23

<210> SEQ ID NO 33
<211> LENGTH: 26
<212> TYPE: DNA
<213> ORGANISM: Mus musculus

<400> SEQUENCE: 33
caggtgacaa gtgacggtgg tctcca                                        26
```

METHODS TO DETECT, TREAT AND PREVENT ACUTE CELLULAR REJECTION IN KIDNEY ALLOGRAFTS

This patent claims the benefit of priority, under 35 U.S.C. §119(e), to U.S. Provisional Patent Application Ser. No. 61/758,887 filed on Jan. 31, 2013, the contents of which application is incorporated herein by reference in its entirety.

GOVERNMENT FUNDING

This invention was made with Government support under Grant Number U01 AI63589 awarded by National Institutes of Health. The United States Government has certain rights in the invention.

BACKGROUND

Organ transplantation or the transfer of an organ from one human to another continues to rise throughout the world as the treatment of choice when an organ is irreversibly damaged or organ function is severely impaired. Organ transplantation is not without complications, not only from the transplant surgery itself, but also from the transplant recipient's own immune system and this process, if it happens suddenly, is called acute rejection.

For example, when acute rejection of a kidney transplant occurs, it manifests itself by a sudden deterioration in kidney transplant function. About 30 percent of transplant recipients experience an episode of acute rejection. Acute rejection can be associated with reduction in the one-year survival rate of kidney grafts from a deceased donor of about 20 percent, and the projected half-life is about four years shorter in patients who have had an episode of acute rejection compared to patients who have not had an episode of acute rejection.

Sometimes, acute rejection can result from the activation of recipient's T cells and/or B cells. The rejection primarily due to T cells is classified as T cell mediated acute rejection or acute cellular rejection (ACR) and the rejection in which B cells are primarily responsible is classified as antibody mediated acute rejection (AMR). Often times, acute rejection of either type can result in the complete loss of transplant function and transplant failure.

An increase in the level of serum creatinine, a clinically used measure of kidney function, is often the first clinical indicator of acute rejection, and is currently the best surrogate marker of acute rejection of either type. However, this biomarker lacks sensitivity and specificity because graft dysfunction can occur due to non-immunological causes.

Two of the commonly used drugs prescribed to transplant recipients to prevent rejection, cyclosporine and tacrolimus, can cause kidney toxicity, and this complication is not readily identified solely on the basis of blood concentrations of cyclosporine/tacrolimus. In kidney transplant patients, the clinical importance of distinguishing acute rejection from cyclosporine/tacrolimus toxicity cannot be overemphasized because the treatment approaches are diametrically opposite. In one instance, continued administration of cyclosporine/tacrolimus for rejection is critical whereas, in the other instance, a reduction in dosage or discontinuation of cyclosporine/tacrolimus is indicated to prevent further kidney toxicity. Furthermore, deterioration in kidney function is not always available as a clinical clue to diagnose rejection because many of the kidney transplants suffer from acute (reversible) renal failure in the immediate post-transplantation period due to injury from organ procurement and the ex-vivo preservation procedures involved.

Currently, acute rejection is diagnosed by performing an invasive core needle biopsy procedure, which obtains a biopsy of the kidney graft. The histological features in the allograft biopsy tissues are then observed. However, this invasive biopsy procedure is associated with complications such as bleeding, arteriovenous fistula, graft loss, and, in severe cases, even death.

Development of a noninvasive test either to anticipate an episode of acute rejection or to diagnose acute rejection without performing the transplant biopsy procedure is a major and an unmet goal in organ transplantation.

SUMMARY

As described herein, the expression levels of just three RNAs in a subject's urine can be used to determine kidney allograft status. The test is noninvasive and can be used to determine whether existing problems are present or whether problems may develop. Thus, one benefit of such a noninvasive test is that allograft function can be monitored and rejection can be identified prior to organ injury and graft dysfunction. Invasive biopsies, with complications such as bleeding and even death of the patient can be avoided. Preemptive anti-rejection therapy can quickly be initiated before rejection problems have progressed because acute transplant rejection can be anticipated. Such a non-invasive test can illuminate the mechanisms responsible for acute rejection. The "one size fits all" approach typically used where all transplant recipients are treated the same way can be avoided, and anti-rejection therapy can be adapted to the specific needs of the patient.

The methods provided herein relate the $\log_{10}$ 18S-normalized CD3ε mRNA, the $\log_{10}$ 18S-normalized IP-10 mRNA, and $\log_{10}$ 18S rRNA expression levels determined from the urine of a subject with a kidney allograft to the subject's kidney allograft status. This three-gene expression relationship is referred to as a 3-gene molecular signature, which can be expressed as follows:

$$\text{signature} = -6.1487 + 0.8534 \log_{10}(CD3\varepsilon/18S) + 0.6376 \log_{10}(IP\text{-}10/18S) + 1.6464 \log_{10}(18S)$$

where:
CD3ε refers to an absolute urinary CD3ε mRNA copy number per microgram of total RNA in a subject's urine sample;
IP-10 refers to an absolute urinary IP-10 mRNA copy number per microgram of total RNA in a subject's urine sample;
18S refers to an absolute urinary 18S rRNA copy number per microgram of total RNA times $10^{-6}$ in a subject's urine sample.
Each measurement of absolute urinary CD3ε mRNA, IP-10 mRNA, and 18S rRNA copy number is a measurement taken from the same sample.

This 3-gene molecular signature represents an excellent-fitting parsimonious test for detection and prediction of acute cellular rejection (ACR) from these mRNA and rRNA levels in urine samples of kidney transplant patients. This signature, hereinafter referred to as "the signature", "diagnostic signature", "3-gene molecular signature" is diagnostic of acute cellular rejection, especially when the value of this signature is greater than −1.21.

The likelihood of acute cellular rejection in a patient can also be monitored by detecting a continuing rise in the diagnostic signature over time. Hence, the methods described herein have prognostic as well as diagnostic value.

In addition, changes in this signature over time provide a method to monitor the efficacy of immunosuppressive therapy in maintaining a stable kidney allograft in humans, wherein an increase in the value of this diagnostic signature over time is indicative of reduced efficacy, and a reduction in the value of this diagnostic signature over time is indicative of increased efficacy.

Further, the changes observed in this diagnostic signature provide a method to guide immunosuppressive therapy for humans with kidney allograft.

DESCRIPTION OF THE FIGURES

FIG. 1A shows a flow chart of patient numbers and events in the Clinical Trials in Organ Transplantation-04 (CTOT-04) Urinary Cell mRNA Profiling Study. Four hundred and ninety two kidney transplant recipients were prospectively enrolled in the multicenter CTOT-04 Urinary Cell mRNA Profiling Study and 4300 urine samples were collected from 485 patients for urinary cell mRNA profiling. The schedule for the collection of sequential urine samples was post-transplant days 3, 7, 15 and 30 and months 2, 3, 4, 5, 6, 9 and 12, and at the time of renal allograft biopsy and two-weeks thereafter. Urine cell pellets were prepared at the clinical sites and shipped to the Gene Expression Monitoring Core at Weill Cornell Medical Center (WCMC). Levels of mRNA for a pre-specified mRNA panel (CD3ε, perforin, granzyme B, PI-9, CD103, IP-10, CXCR3, and TGF-β1) and 18S rRNA were measured in urinary cells with the use of preamplification enhanced quantitative real time PCR assays. Prior to data analysis for the association of mRNA levels with allograft status, the urine specimen was classified as either (i) quality control (QC) passed if the 18S rRNA copy number was greater than or equal to $5 \times 10^7$ and the TGF-β1 mRNA copy number was greater than or equal to 100 copies per microgram of total RNA isolated from the urine pellet or (ii) failed if either of these copy number thresholds were not met. Among the 4300 urine specimens, 3559 passed quality control parameters and 741 did not. Two hundred and twenty of the enrolled 485 patients underwent 410 kidney allograft biopsies (Biopsy group) and 265 did not have a recorded biopsy (No Biopsy group). The number of patients with biopsy-matched urine samples (urine collected minus 3 days to plus 1 day of biopsy and QC-passed) are shown for patients with acute cellular rejection (ACR Biopsy group, acute cellular rejection was defined as Banff Grade 1A or higher), without any acute rejection features in biopsy (No Rejection Biopsy group), acute antibody mediated rejection (AMR Biopsy group), Borderline changes (Borderline Biopsy group), or Other biopsy findings (Other Biopsy group). The number of patients listed under different biopsy diagnostic categories exceeds the 220 patients in the Biopsy group since several patients had multiple biopsies with different diagnoses. In the No Biopsy group, 202 of 265 patients met the following criteria: (i) average serum creatinine less than or equal to 2.0 mg/dl for available 6-, 9-, and 12-month assessments post-transplantation (in 3 of 202 patients, 6-, 9-, and 12-month creatinine level was not available but their 24-month creatinine level was less than or equal to 2.0 mg/dl); (ii) no graft loss or death during the first 12 months following transplantation; (iii) no treatment for acute rejection; and (iv) no evidence of infection by Cytomegalovirus (CMV) or BK virus (BKV); this group of 202 patients was labeled the Stable (no biopsy) group. Sixty three patients in the No Biopsy group did not meet the criteria listed above; among these 63 patients, 47 had no serum creatinine values beyond 5-mos post-transplantation, 4 had serum creatinine values at 6-, 9-, and/or 12-months that averaged>2.0 mg/dl, 9 were treated for CMV, BKV infection or both, 1 lost his/her graft within the first 12 months, and 2 patients died within the first 12 months. The number of patients and the number of longitudinally collected urine samples are shown for the patients who met or did not meet the criteria for inclusion in the Stable (no biopsy) group. (NW: Northwestern Memorial Hospital, Northwestern University Feinberg School of Medicine, Chicago, Ill.; U Penn: Hospital of University of Pennsylvania, Philadelphia, Pa.; UW: University of Wisconsin Hospital and Clinics, Madison, Wis.; NYPH-CUMC: New York Presbyterian Hospital-Columbia University Medical Center, New York, N.Y.; NYPH-WCMC: New York Presbyterian Hospital-Weill Cornell Medical Center, New York, N.Y.; WCMC: Weill Cornell Medical College, New York, N.Y.). FIG. 1B summarizes information about patients, biopsies and urine samples in the CTOT-04 clinical trial. A total of 4300 urine samples were collected from 485 patients for urinary-cell messenger RNA (mRNA) profiling after transplantation on days 3, 7, 15, and 30; in months 2, 3, 4, 5, 6, 9, and 12; and at the time of kidney-allograft biopsy and 2 weeks thereafter. Of the 4300 urine specimens, 3559 were classified as passing quality control (QC) and 741 were classified as not passing. A total of 220 patients underwent 410 kidney-allograft biopsies, and 265 did not undergo biopsy. The numbers of patients with biopsy-matched urine samples (urine samples that were collected from 3 days before to 1 day after biopsy and that passed QC) are shown for patients with acute cellular rejection (defined as Banff grade IA or higher), for those without any rejection features in the biopsy sample, for those with acute antibody-mediated rejection, for those with borderline changes, and for those with other biopsy findings. The number of patients listed under different diagnostic categories exceeds the 220 patients who underwent biopsy because several patients had multiple biopsies with different diagnoses. Among the 265 patients who did not undergo biopsy, 202 met the criteria for stable graft function, of whom 201 had urine samples that passed QC. Patient-enrollment information and recipient and donor characteristics are provided in the Examples.

18S]+1.6464 log 10[18S]) as follows. Absolute levels of CD3ε mRNA, IP-10 mRNA, and 18S rRNA in the cells from each urine sample were measured with the use of polymerase-chain reaction assays, with the units of measurement being copies per microgram of total RNA for each mRNA measure and 18S rRNA copies ($\times 10^{-6}$) per microgram of total RNA. The mRNA copy numbers were 18S-normalized by dividing the mRNA copy number by the 18S rRNA copy number in the same sample, and the ratio was $\log_{10}$-transformed.

Figure 6A:
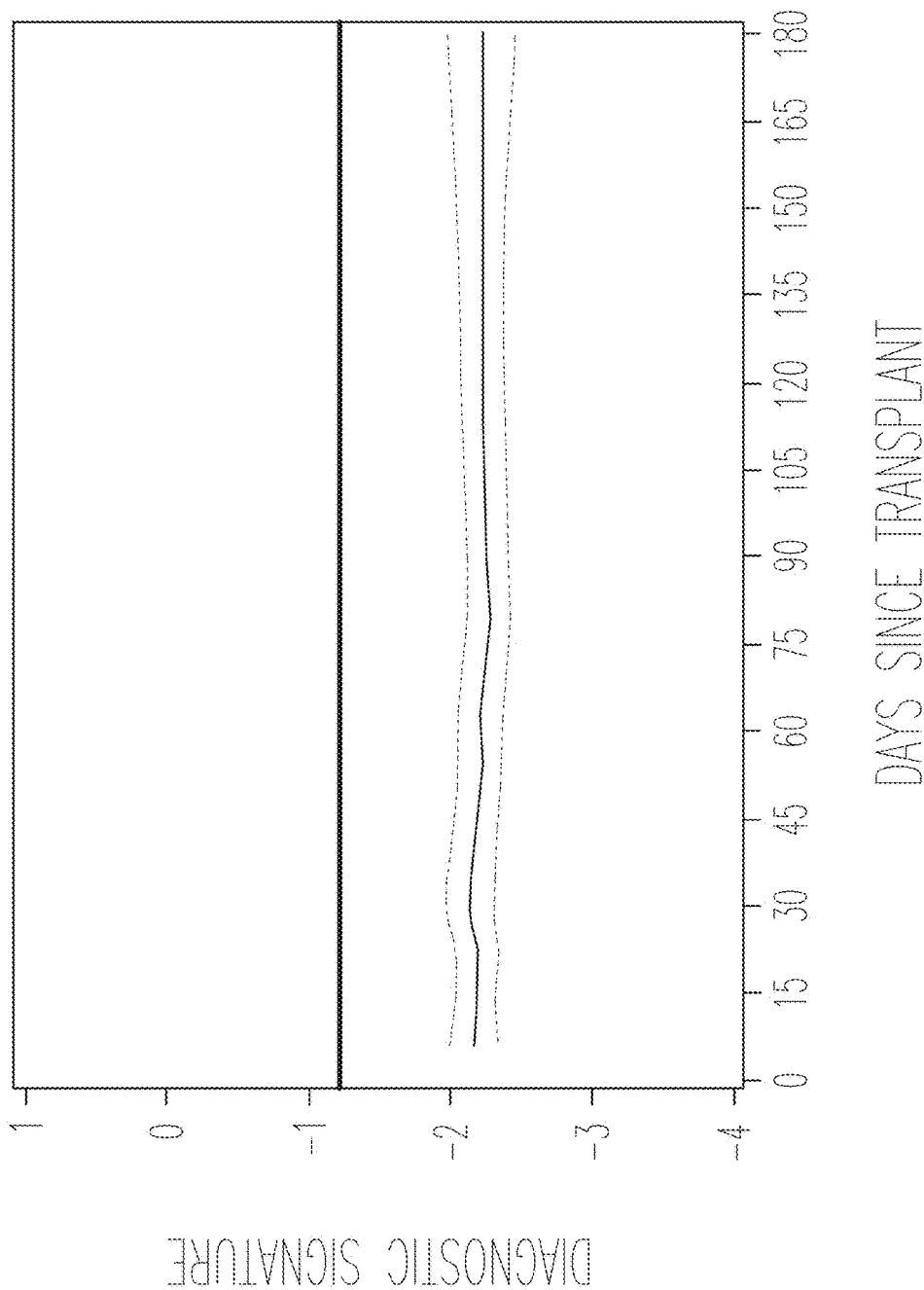
Figure 6B:
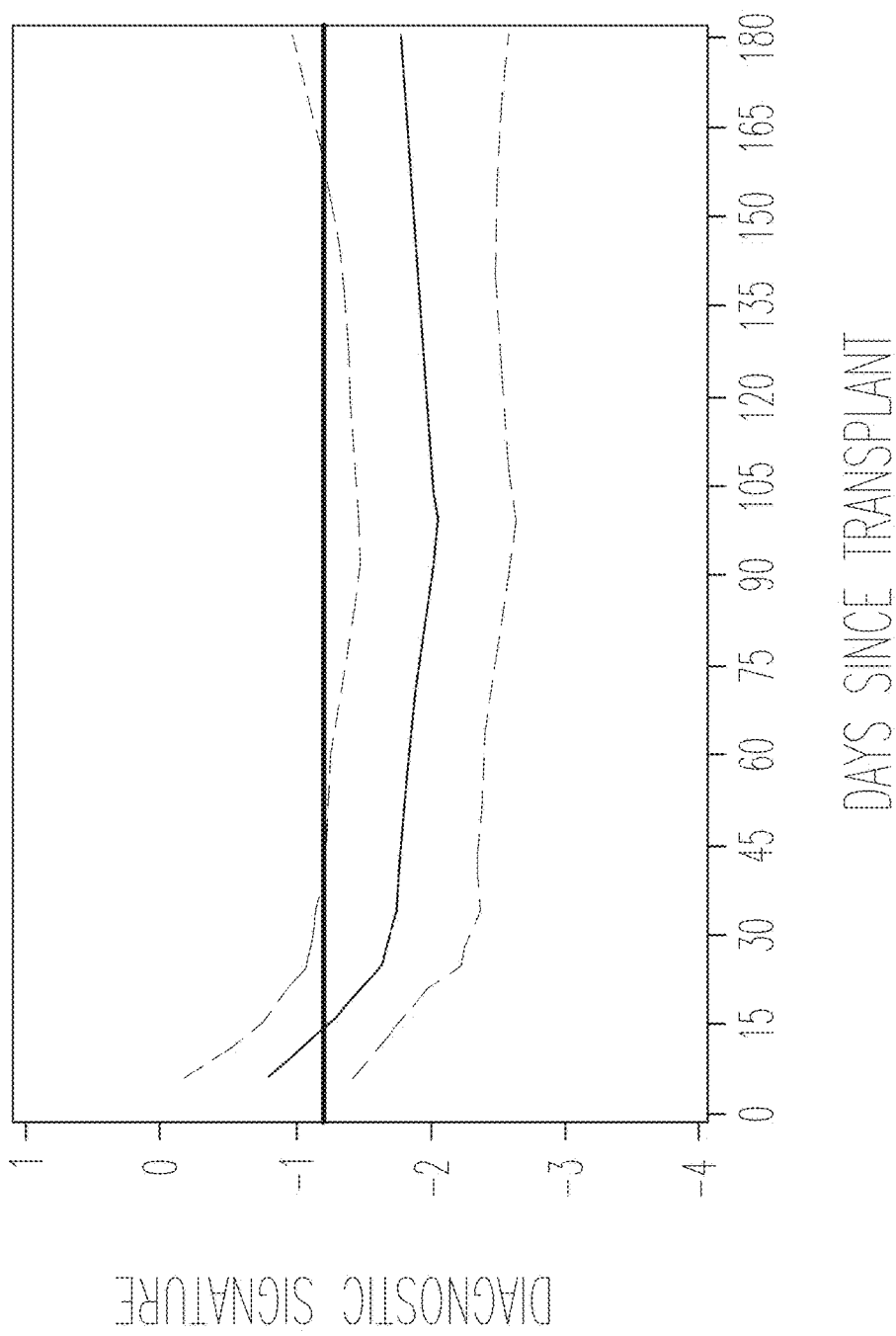
Figure 6C:
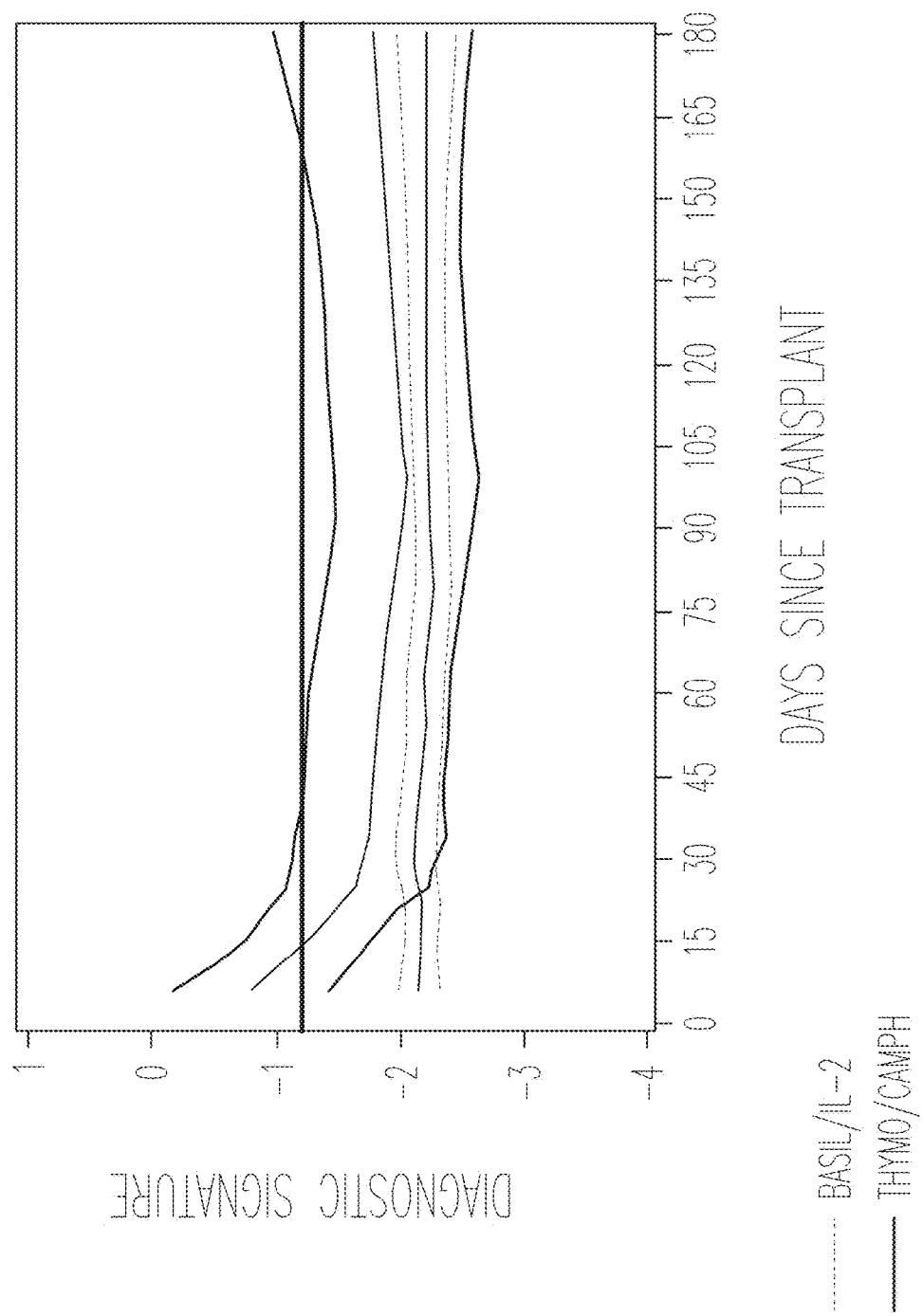

FIGS. 6A-6C illustrate the Impact of Induction Therapy on the Longitudinal Trajectory of Diagnostic Signature. LOESS curves (mean and 95% confidence intervals [shaded area]) portraying the average within-person prospective trajectory of the diagnostic signature during days 5-180 post-transplant for those who received T cell depleting antibodies (Thymoglobulin/CAMPATH-1H) or non-depleting anti-IL-2 receptor antibodies (Basiliximab). These trajectories are based only on those patients in the Stable (no biopsy) group and the Only No Rejection Biopsy group. FIG. 6A shows that the diagnostic signature score of those who received Thymoglobulin/CAMPATH-1H is flat during the first 6 months of transplantation; FIG. 6B shows, for those who received anti-IL-2 receptor antibodies, a substantially elevated diagnostic signature early on, decreasing rapidly during the first 30 days, and then more gradually through the next two months post-transplant. FIG. 6C shows both trajectories to highlight the difference in trajectories, especially during the first month post-transplant, based on whether patients received T cell depleting or non-depleting induction therapy. The difference between the 29 patients who received Basiliximab and the 265 patients who received either Thymoglobulin or CAMPATH-1H is substantive and significant ($\chi 2=16.44$, df=3, p=0.0009). In all panels, the central lines indicate the trajectory, the associated dashed lines the 95% confidence interval, and the straight lines at about −1.2 shown the diagnostic threshold.

In the following description, reference is made to the accompanying drawings that form a part hereof, and in which is shown by way of illustration specific embodiments that may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

DETAILED DESCRIPTION

Methods and devices are described herein for detecting, monitoring, and predicting acute cellular rejection in a kidney transplant patient from levels of RNA in the patient's urine. Acute cellular rejection is a treatable cause of kidney allograft failure. As described herein, acute cellular rejection can be noninvasively and accurately diagnosed using a 3-gene signature determined from quantified levels of CD3ε mRNA, IP-10 mRNA and 18S rRNA in urine samples.

For example, the 3-gene diagnostic signature measured in urine specimens from clinically stable allograft patients can be used to monitor the likelihood of such a patient to subsequently develop acute cellular rejection. The studies reported here demonstrate that the diagnostic signature obtained from measurements conducted on urine specimens from patients with normal allograft biopsies and in clinically stable patients was relatively flat and distinct compared to the progressive increase observed in specimens from those who later developed biopsy confirmed acute cellular rejection.

The diagnostic signature can also serve to direct the immunosuppressive therapy of a transplant patient. The levels of this signature reflect the potency of immunosuppressive regimens. For example, a marked rise in the mRNA levels in the absence of clinical manifestations of acute cellular rejection indicates that preemptive anti-rejection therapy can be needed.

In addition, the gene signature can distinguish acute cellular rejection from antibody-mediated rejection (AMR), borderline and other changes.

The RNA expression levels correlated with development of acute cellular rejection (and other kidney problems) include 18S-normalized CD3ε mRNA, IP-10 mRNA and 18S rRNA expression levels.

The 3-gene signature discriminated acute cellular rejection biopsies from biopsies without rejection and the AUC was 0.85 (95% CI: 0.78-0.91, P<0.0001) by ROC curve analysis. The optimism-adjusted AUC was 0.83 by bootstrap re-sampling and the Hosmer-Lemeshow test indicated excellent fit (P=0.77). The calibration curve showed excellent calibration (Cox's intercept=−0.06; slope=0.92). In an external validation dataset, the AUC was 0.74 (95% CI: 0.61 to 0.86, P=0.0002) and not different from CTOT-04's AUC (P=0.13). The signature distinguished ACR from acute antibody mediated rejection and borderline rejection (AUC=0.78, P<0.0001), patients induced with anti-IL-2 receptor antibodies from T cell depleting antibodies (P=0.0009), and diagnostic of ACR in both groups. Urinary tract infection did not impact the signature (P=0.69). The average trajectory of the signature in repeat urine samples remained below the threshold diagnostic of ACR in the group without an ACR whereas there was a sharp rise during the weeks prior to an ACR biopsy (P<0.0001).

Heretofore, robust yardsticks for defining the immune status of the transplant recipient have not been developed. The relatively flat trajectory of the 3-gene diagnostic signature of those who do not manifest acute cellular rejection is in contrast to this signature's increasing trajectory in those who do develop acute cellular rejection. Thus, the 3-gene diagnostic signature provides a tool not only for detecting acute cellular rejection but also for monitoring a subject's immune status and for titrating an appropriate immunosuppressive therapy. The finding that the signature can reflect the potency of immunosuppressive therapy offers new opportunities for more precise treatment and reduced trauma to the patient.

Although acute cellular rejection is frequently treatable, it is a well-recognized precursor of chronic rejection and ultimate graft loss. Current preventive strategies include immunosuppression, initiated at the time of transplant with adjustments in medications made based on drug levels, toxicity and clinical events such as increased creatinine. The marked increase in the trajectory of the diagnostic signature weeks preceding acute cellular rejection, in addition to foreshadowing the development of ACR, offers new opportunities for preemptive anti-rejection therapy, prior to irreversible tissue injury.

In sum, the well-calibrated, parsimonious diagnostic signature described herein is determined from the RNA expression levels of three genes relevant to acute cellular rejection. The signature provides both physician and patient with direct measures of risk (the predicted probability that a biopsy would reveal acute cellular rejection) and a means of assessing progress/decline over repeated assessments. The signature provides a reliable method for discrimination and diagnosis and an exceptional tool for assessing the likelihood of acute cellular rejection in a given patient at any point following transplantation. The results of the CTOT-4 clinical trial study described herein show that, in addition to minimizing invasive biopsies, the urinary cell mRNA and rRNA profiling described here can direct preemptive anti-rejection therapy and personalized immunosuppression.

Determination of CD3ε mRNA, IP-10 mRNA and 18S rRNA Expression Levels

Any procedure available to those of skill in the art can be employed to determine the expression levels of CD3ε mRNA, IP-10 mRNA and 18S rRNA. For example, probes, primers, and/or antibodies can be employed in quantitative nucleic acid amplification reactions (e.g., quantitative polymerase chain reaction (PCR)), primer extension, Northern blot, immunoassay, immunosorbent assay (ELISA), radioimmunoassay (RIA), immunofluorimetry, immunoprecipitation, equilibrium dialysis, immunodiffusion, immunoblotting, mass spectrometry and other techniques available to the skilled artisan.

In some embodiments, the expression levels of CD3ε mRNA, IP-10 mRNA and 18S rRNA are determined using probes or primers that can hybridize to the CD3ε mRNA, IP-10 mRNA or 18S rRNA. Sequences for CD3ε mRNA, IP-10 mRNA and 18S rRNA are readily available and can be used to make such probes and primers.

For example, the following sequence for a human 18S rRNA is available from the National Center for Biotechnology Information database (see website at ncbi.nlm.nih.gov) as accession number K03432 (SEQ ID NO:1).

```
    1 CGCTGCTCCT CCCGTCGCCG TCCGGGCCCG TCCGTCCGTC

41 CGTCCGTCGT CCTCCTCGCT NNNNCGGGGC GCCGGGCCCG

61 TCCTCACNGG CCCCCGNNNN NGTCCNGGCC CGTCGGGGCC

121 TCGCCGCGCT CTACCTTACC TACCTGGTTG ATCCTGCCAG

161 TAGCATATGC TTGTCTCAAA GATTAAGCCA TGCATGTCTA

201 AGTACGCACG GCCGGTACAG TGAAACTGCG AATGGCTCAT

241 TAAATCAGTT ATGGTTCCTT TGGTCGCTCG CTCCTCTCCT

281 ACTTGGATAA CTGTGGTAAT TCTAGAGCTA ATACATGCCG

321 ACGGGCGCTG ACCCCCTTCG CGGGGGGGAT GCGTGCATTT

361 ATCAGATCAA AACCAACCCG GTCAGCCCCT CTCCGGCCCC

401 GGCCGGGGGG CGGGCGCCGG CGGCTTTGGT GACTCTAGAT

441 AACCTCGGGC CGATCGCACG CCCCCCGTGG CGGCGACGAC

481 CCATTCGAAC GTCTGCCCTA TCAACTTTCG ATGGTAGTCG

521 CCGTGCCTAC CATGGTGACC ACGGGTGACG GGGAATCAGG

561 GTTCGATTCC GGAGAGGGAG CCTGAGAAAC GGCTACCACA

601 TCCAAGGAAG GCAGCAGGCG CGCAAATTAC CCACTCCCGA

641 CCCGGGGAGG TAGTGACGAA AAATAACAAT ACAGGACTCT

681 TTCGAGGCCC TGTAATTGGA ATGAGTCCAC TTTAAATCCT

721 TTAACGAGGA TCCATTGGAG GGCAAGTCTG GTGCCAGCAG

761 CCGCGGTAAT TCCAGCTCCA ATAGCGTATA TTAAAGTTGC

801 TGCAGTTAAA AAGCTCGTAG TTGGATCTTG GGAGCGGGCG

841 GGCGGTCCGC CGCGAGGCGA GCCACCGCCC GTCCCCGCCC

881 CTTGCCTCTC GGCGCCCCCT CGATGCTCTT AGCTGAGTGT

921 CCCGCGGGGC CCGAAGCGTT TACTTTGAAA AAATTAGAGT

961 GTTCAAAGCA GGCCCGAGCC GCCTGGATAC CGCAGCTAGG

1001 AATAATGGAA TAGGACCGCG GTTCTATTTT GTTGGTTTTC

1041 GGAACTGAGG CCATGATTAA GAGGGACGGC CGGGGGCATT

1081 CGTATTGCGC CGCTAGAGGT GAAATTCCTT GGACCGGCGC

1121 AAGACGGACC AGAGCGAAAG CATTTGCCAA GAATGTTTTC

1161 ATTAATCAAG AACGAAAGTC GGAGGTTCGA AGACGATCAG

1201 ATACCGTCGT AGTTCCGACC ATAAACGATG CCGACCGGCG

1241 ATGCGGCGGC GTTATTCCCA TGACCCGCCG GGCAGCTTCC

1281 GGGAAACCAA AGTCTTTGGG TTCCGGGGGG AGTATGGTTG

1321 CAAAGCTGAA ACTTAAAGGA ATTGACGGAA GGGCACCACC

1361 AGGAGTGGAG CCTGCGGCTT AATTTGACTC AACACGGGAA

1401 ACCTCACCCG GCCCGGACAC GGACAGGATT GACAGATTGA

1441 TAGCTCTTTC TCGATTCCGT GGGTGGTGGT GCATGGCCGT

1481 TCTTAGTTGG TGGAGCGATT TGTCTGGTTA ATTCCGATAA

1521 CGAACGAGAC TCTGGCATGC TAACTAGTTA CGCGACCCCC

1561 GAGCGGTCGG CGTCCCCCAA CTTCTTAGAG GACAAGTGG

1601 CGTTCAGCCA CCCGAGATTG AGCAATAACA GGTCTGTGAT

1641 GCCCTTAGAT GTCCGGGGCT GCACGCGCGC TACACTGACT

1681 GGCTCAGCGT GTGCCTACCC TACGCCGGCA GGCGCGGGTA

1721 ACCCGTTGAA CCCCATTCGT GATGGGGATC GGGGATTGCA

1761 ATTATTCCCC ATGAACGAGG AATTCCCAGT AAGTGCGGGT

1801 CATAAGCTTG CGTTGATTAA GTCCCTGCCC TTTGTACACA

1841 CCGCCCGTCG CTACTACCGA TTGGATGGTT TAGTGAGGCC

1881 CTCGGATCGG CCCCGCCGGG GTCGGCCCAC GGCCCTGGCG

1921 GAGCGCTGAG AAGACGGTCG AACTTGACTA TCTAGAGGAA

1961 GTAAAAGTCG TAACAAGGTT TCCGTAGGTG AACCTGCGGA

2001 AGGATCATTA ACGGAGCCCG GACGGCGGCC CGCGGCGGCG

2041 CCGCGCCGCG CTTCCCTCCG CACACCCACC CCCCACCGC

2081 GACGGCGCGT GCGGGCGGGG CCGTGCCCGT TCGTTCGCTC

2121 GCTCGTTCGT TCGCCGCCCG GCCGGCCGC GAGAGCCGAG

2161 AACTCGGGAG GGAGACGGGG GAGAGAGAGA GAGAGAGAGA

2201 GAGAGAGAGA GAGAGAGAGA GAAAGAAGGG CGTGT
```

A cDNA sequence for a human CD3ε is also available from the National Center for Biotechnology Information database as accession number NM_000733 (SEQ ID NO:2.

```
    1 TATTGTCAGA GTCCTCTTGT TGGCCTTCT AGGAAGGCTG

41 TGGGACCCAG CTTTCTTCAA CCAGTCCAGG TGGAGGCCTC
```

```
 81 TGCCTTGAAC GTTTCCAAGT GAGGTAAAAC CCGCAGGCCC
121 AGAGGCCTCT CTACTTCCTG TGTGGGGTTC AGAAACCCTC
161 CTCCCCTCCC AGCCTCAGGT GCCTGCTTCA GAAAATGAAG
201 TAGTAAGTCT GCTGGCCTCC GCCATCTTAG TAAAGTAACA
241 GTCCCATGAA ACAAAGATGC AGTCGGGCAC TCACTGGAGA
281 GTTCTGGGCC TCTGCCTCTT ATCAGTTGGC GTTTGGGGGC
321 AAGATGGTAA TGAAGAAATG GGTGGTATTA CACAGACACC
361 ATATAAAGTC TCCATCTCTG GAACCACAGT AATATTGACA
401 TGCCCTCAGT ATCCTGGATC TGAAATACTA TGGCAACACA
441 ATGATAAAAA CATAGGCGGT GATGAGGATG ATAAAAACAT
481 AGGCAGTGAT GAGGATCACC TGTCACTGAA GGAATTTTCA
521 GAATTGGAGC AAAGTGGTTA TTATGTCTGC TACCCCAGAG
561 GAAGCAAACC AGAAGATGCG AACTTTTATC TCTACCTGAG
601 GGCAAGAGTG TGTGAGAACT GCATGGAGAT GGATGTGATG
641 TCGGTGGCCA CAATTGTCAT AGTGGACATC TGCATCACTG
681 GGGGCTTGCT GCTGCTGGTT TACTACTGGA GCAAGAATAG
721 AAAGGCAAG GCCAAGCCTG TGACACGAGG AGCGGGTGCT
761 GGCGGCAGGC AAAGGGGACA AAACAAGGAG AGGCCACCAC
801 CTGTTCCCAA CCCAGACTAT GAGCCCATCC GGAAAGGCCA
841 GCGGGACCTG TATTCTGGCC TGAATCAGAG ACGCATCTGA
881 CCCTCTGGAG AACACTGCCT CCCGCTGGCC CAGGTCTCCT
921 CTCCAGTCCC CCTGCGACTC CCTGTTTCCT GGGCTAGTCT
961 TGGACCCCAC GAGAGAGAAT CGTTCCTCAG CCTCATGGTG
1001 AACTCGCGCC CTCCAGCCTG ATCCCCGCT CCCTCCTCCC
1041 TGCCTTCTCT GCTGGTACCC AGTCCTAAAA TATTGCTGCT
1081 TCCTCTTCCT TTGAAGCATC ATCAGTAGTC ACACCCTCAC
1121 AGCTGGCCTG CCCTCTTGCC AGGATATTTA TTTGTGCTAT
1161 TCACTCCCTT CCCTTTGGAT GTAACTTCTC CGTTCAGTTC
1201 CCTCCTTTTC TTGCATGTAA GTTGTCCCCC ATCCCAAAGT
1241 ATTCCATCTA CTTTTCTATC GCCGTCCCCT TTTGCAGCCC
1281 TCTCTGGGGA TGGACTGGGT AAATGTTGAC AGAGGCCCTG
1321 CCCCGTTCAC AGATCCTGGC CCTGAGCCAG CCCTGTGCTC
1361 CTCCCTCCCC CAACACTCCC TACCAACCCC CTAATCCCCT
1401 ACTCCCTCCA CCCCCCCTCC ACTGTAGGCC ACTGGATGGT
1441 CATTTGCATC TCCGTAAATG TGCTCTGCTC CTCAGCTGAG
1481 AGAGAAAAAA ATAAACTGTA TTTGGCTGCA GAAAAAAAAA
1521 AAAAAAAAAA AAAA
```

The following cDNA sequence is also available for a human IP-10 from the National Center for Biotechnology Information database as accession number NM_001565.1 (GI:4504700) (SEQ ID NO:3).

```
   1 GAGACATTCC TCAATTGCTT AGACATATTC TGAGCCTACA
  41 GCAGAGGAAC CTCCAGTCTC AGCACCATGA ATCAAACTGC
  81 GATTCTGATT TGCTGCCTTA TCTTTCTGAC TCTAAGTGGC
 121 ATTCAAGGAG TACCTCTCTC TAGAACCGTA CGCTGTACCT
 161 GCATCAGCAT TAGTAATCAA CCTGTTAATC CAAGGTCTTT
 201 AGAAAAACTT GAAATTATTC CTGCAAGCCA ATTTTGTCCA
 241 CGTGTTGAGA TCATTGCTAC AATGAAAAAG AAGGGTGAGA
 281 AGAGATGTCT GAATCCAGAA TCGAAGGCCA TCAAGAATTT
 321 ACTGAAAGCA GTTAGCAAGG AAATGTCTAA AAGATCTCCT
 361 TAAAACCAGA GGGGAGCAAA ATCGATGCAG TGCTTCCAAG
 401 GATGGACCAC ACAGAGGCTG CCTCTCCCAT CACTTCCCTA
 441 CATGGAGTAT ATGTCAAGCC ATAATTGTTC TTAGTTTGCA
 481 GTTACACTAA AAGGTGACCA ATGATGGTCA CCAAATCAGC
 521 TGCTACTACT CCTGTAGGAA GGTTAATGTT CATCATCCTA
 561 AGCTATTCAG TAATAACTCT ACCCTGGCAC TATAATGTAA
 601 GCTCTACTGA GGTGCTATGT TCTTAGTGGA TGTTCTGACC
 641 CTGCTTCAAA TATTTCCCTC ACCTTTCCCA TCTTCCAAGG
 681 GTACTAAGGA ATCTTTCTGC TTTGGGGTTT ATCAGAATTC
 721 TCAGAATCTC AAATAACTAA AAGGTATGCA ATCAAATCTG
 761 CTTTTTAAAG AATGCTCTTT ACTTCATGGA CTTCCACTGC
 801 CATCCTCCCA AGGGGCCCAA ATTCTTTCAG TGGCTACCTA
 841 CATACAATTC CAAACACATA CAGGAAGGTA GAAATATCTG
 881 AAAATGTATG TGTAAGTATT CTTATTTAAT GAAAGACTGT
 921 ACAAAGTATA AGTCTTAGAT GTATATATTT CCTATATTGT
 961 TTTCAGTGTA CATGGAATAA CATGTAATTA AGTACTATGT
1001 ATCAATGAGT AACAGGAAAA TTTTAAAAAT ACAGATAGAT
1041 ATATGCTCTG CATGTTACAT AAGATAAATG TGCTGAATGG
1081 TTTTCAAATA AAAATGAGGT ACTCTCCTGG AAATATTAAG
1121 AAAGACTATC TAAATGTTGA AAGATCAAAA GGTTAATAAA
1161 GTAATTATAA CT
```

The level of expression is determined for one or more genes in sample obtained from a subject. The sample can be a fluid sample such as a blood sample, a peripheral blood mononuclear cell (PBMC) sample, a urine sample, a sample of broncho-alveolar lavage fluid, a sample of bile, pleural fluid or peritoneal fluid, any other fluid secreted or excreted by a normally or abnormally functioning allograft, or any other fluid resulting from exudation or transudation through an allograft or in anatomic proximity to an allograft, or any fluid in fluid communication with the allograft. One convenient example of a sample for determination of the level of gene expression is a urine sample.

RNA can be isolated from the samples by procedures available in the art. Commercially available kits can be employed for such isolation. Alternatively, the urine sample can be treated to lyse any cells therein and the RNA expression levels can be determined with little or no RNA purification step.

For example, the CD3ε mRNA, IP-10 mRNA and 18S rRNA can be determined from a urinary cell sample from the recipient of an organ transplant. Any method known to those in the art can be employed for determining the level of CD3ε mRNA, IP-10 mRNA and 18S rRNA. For example, total RNA, which includes mRNA and rRNA, can be isolated from the sample by use of a commercial kit, such as the TRI Reagent® commercially available from Molecular Research Center, Inc. (Cincinnati, Ohio), can be used to isolate RNA.

Any method known to those in the art can be employed for determining the level of gene expression. For example, one method for measuring gene expression is by real-time RT-PCR. Classical TaqMan® Gene Expression Assays or TaqMan® Low Density Array microfluidic cards (Applied Biosystems) can be employed. Such methods provide quantitative measurements of RNA levels.

In another example, a microarray can be used. Microarrays are known in the art and consist of a surface to which probes that correspond in sequence to gene products (e.g. mRNAs, polypeptides, fragments thereof etc.) can be specifically hybridized or bound to a known position. Hybridization intensity data detected by the scanner are automatically acquired and processed by the Affymetrix Microarray Suite (MAS5) software. Raw data is normalized to expression levels using a target intensity of 150.

The transcriptional state of a cell may be measured by other gene expression technologies known in the art. Several such technologies produce pools of restriction fragments of limited complexity for electrophoretic analysis, such as methods combining double restriction enzyme digestion with phasing primers (e.g. EP-A1-0534858), or methods selecting restriction fragments with sites closest to a defined mRNA end (e.g. Prashar et al; Proc. Nat. Acad. Sci., 93, 659-663, 1996). Other methods statistically sample cDNA pools, such as by sequencing sufficient bases (e.g. 20-50 bases) in each multiple cDNAs to identify each cDNA, or by sequencing short tags (e.g. 9-10 bases) which are generated at known positions relative to a defined mRNA end (e.g. Velculescu, Science, 270, 484-487, 1995) pathway pattern.

The quantification of CD3ε mRNA, IP-10 mRNA and 18S rRNA from the total mRNA of a sample can be performed by any method known to those in the art. For example, kinetic, quantitative PCR involves reverse transcribing CD3ε mRNA, IP-10 mRNA and 18S rRNA by using reverse-transcriptase polymerase chain reaction (RT-PCR) to obtain CD3ε, IP-10, and 18S rRNA cDNA. The cDNA can then, for example, be amplified by PCR followed by quantitation using a suitable detection apparatus. Determination of CD3ε mRNA, IP-10 mRNA and 18S rRNA expression levels can involve a preamplification step followed by an amplification process. See Example 2 for exemplary methods for quantitation of CD3ε mRNA, IP-10 mRNA and 18S rRNA by kinetic, quantitative PCR.

Amplification systems utilizing, for example, PCR or RT-PCR methodologies are available to those skilled in the art. For a general overview of amplification technology, see, for example, Dieffenbach et al., PCR Primer: A Laboratory Manual, Cold Spring Harbor Laboratory Press, New York (1995).

An alternative method for determining the level of CD3ε mRNA, IP-10 mRNA and 18S rRNA includes the use of molecular beacons and other labeled probes useful in, for example multiplex PCR. In a multiplex PCR assay, the PCR mixture contains primers and probes directed to the CD3ε mRNA, IP-10 mRNA and 18S rRNA. Typically, a single fluorophore is used in the assay. The molecular beacon or probe is detected to determine the level of CD3ε mRNA, IP-10 mRNA and 18S rRNA. Molecular beacons are described, for example, by Tyagi and Kramer (Nature Biotechnology 14, 303-308, (1996)) and by Andrus and Nichols in U.S. Patent Application Publication No. 20040053284.

Another method includes, for instance, quantifying cDNA (obtained by reverse transcribing the CD3ε mRNA, IP-10 mRNA and 18S rRNA using a fluorescence based real-time detection method, such as the ABI PRISM 7500, 7700, or 7900 Sequence Detection System (TaqMan®) commercially available from Applied Biosystems, Foster City, Calif., or similar system as described by Heid et al., (Genome Res. 1996; 6:986-994) and Gibson et al. (Genome Res. 1996; 6:995-1001).

Generally, the level of CD3ε mRNA, IP-10 mRNA and 18S rRNA in a sample is upregulated if the gene expression of CD3ε mRNA, IP-10 mRNA and 18S rRNA is increased. In some embodiments, upregulation includes increases above a baseline level of 10%, 15%, 20%, 25%, 30%, 35%, 40%, 45%, 50%, 55%, 60%, 65%, 70%, 75%, 80%, 85%, 90%, 95%, 100% or higher.

For example, a discriminatory level for upregulated gene expression (e.g., the baseline magnitude of gene expression) of CD3ε mRNA, IP-10 mRNA and 18S rRNA includes the mean±95% confidence interval of a group of values observed in non-rejecting transplants (e.g., baseline levels or control levels). Upregulation of CD3ε mRNA, IP-10 mRNA and 18S rRNA expression is considered to be significantly greater if the value is greater than the mean±95% confidence interval of a group of values observed in non-rejecting transplants. Similarly, the level of CD3ε mRNA, IP-10 mRNA and 18S rRNA in the sample is considered to be significantly lower if the amount of CD3ε mRNA, IP-10 mRNA and 18S rRNA detected is lower than the mean±95% confidence interval of the amount detected in non-rejecting transplants.

In some embodiments, the expression level is determined using log-transformed levels of CD3ε mRNA, IP-10 mRNA and 18S rRNA in a urine cell sample from the patient. The log transformation or RNA levels substantially reduced the positive skew in the data. In some embodiments, the level of gene expression is determined using log-transformed RNA levels determined by normalizing mRNA levels to 18S rRNA using a logistic regression model of CD3ε mRNA, IP-10 mRNA and 18S rRNA or a weighted combination of log transformed, normalized RNA levels of CD3ε mRNA, IP-10 mRNA and 18S rRNA based on a logistic regression model. Logistic regression models are used for prediction of the probability of occurrence of acute rejection by fitting data to a logistic curve. It is a generalized linear model used for binomial regression.

In some embodiments, for interpretation of quantitative gene expression measurements, a normalizer may be used to correct expression data for differences in cellular input, RNA quality, and RT efficiency between samples. In some embodiments, to accurately assess whether increased RNA is significant, the gene expression can be normalized to accurately compare levels of expression between samples, for example, between a baseline (control) level and an expression level detected in a test sample. In quantitative assays, such as for example, quantitative real-time Reverse Transcriptase-PCR(RT-PCR) normalization can be performed using housekeeping genes (e.g., 18S rRNA) as references against the expression level of a gene under investigation. Normalization includes rendering the measurements of different arrays or PCR or in particular RT-PCR experiments comparable by reducing or removing the technical variability. Within these experiments there exists a multiplicity of sources capable of falsifying the measurements. Possible technical sources of interference are: different efficiency in reverse transcription, labeling or hybridization reactions, as well as problems with the arrays, batch effects in reagents, or lab-specific conditions. A more robust detection of gene expression can occur when normalization is employed.

Normalization can involve use of a "housekeeping gene" which is utilized as a reference, internal control or reference value in the quantification of gene expression. The housekeeping gene allows an identification and quantitative analysis of a gene whose activity is regulated differentially in different pathological conditions. A housekeeping gene exhibits minimum change of expression and transcription across different RNA samples and thus serves as a control, or reference, for the measurement of variable gene activities across different samples. Housekeeping genes for mRNA detection include, for example, 2-Microglobulin ($\beta$2M), Glucose-6-phosphate dehydrogenase (G6PDH), 5-aminolevulinate synthase (ALAS or ALAS 1) Hypoxanthinephosphoribosyltransferase (HPRT), Porphobilinogen deaminase (PBGD), 18S rRNA, or the like. Various housekeeping genes and normalization reagents are available from many sources including Applied Biosystems, (Foster City, Calif.), and geNorm® kits Hoffmann-La Roche (Nutley, N.J.).

In some embodiments, 18S rRNA is used for normalization in gene expression analysis. For example, the values of 18S rRNA-normalized CD3$\epsilon$ mRNA and 18S rRNA-normalized IP-10 mRNA can be used in the diagnostic signature provided herein.

Comparison of Expression Levels

Statistical calculations can be performed using, for example, GraphPad Prism software version 4.0 (GraphPad Software, Inc. La Jolla, Calif.). By using 18S rRNA-normalized levels, the Mann-Whitney U test to test the difference between the group with acute rejection and the group with normal biopsy results can be obtained. Categorical variables can be compared using, for example, Fisher's exact test or chi-square analysis.

Receiver Operating Characteristic (ROC) curves can be generated for individual mRNA levels and a linear combination of mRNA levels to determine the cutoff points that yielded the highest combined sensitivity and specificity for detecting ACR or anticipating ACR. This involves measuring the mRNA levels of CD3$\epsilon$ mRNA, IP-10 mRNA and 18S rRNA alone or in any combination. For example, all three markers can be measured separately, all together, or in any combination. Thus, the RNA levels of CD3$\epsilon$ mRNA, IP-10 mRNA and 18S rRNA can all be measured together. Alternatively, the RNA levels of CD3$\epsilon$ mRNA can be measured with IP-10 mRNA; or the RNA levels of CD3$\epsilon$ mRNA can be measured with 18S rRNA; or the RNA levels of IP-10 mRNA can be measured 18S rRNA. These combinations are then weighted based on increased expression. Such statistical analyses with different biomarkers are described in Afaneh et al., Transplantation 90(12):1381-7 (2010), and Zhang et al., A Linear Regression Framework For Receiver Operating Characteristics (ROC) Curve Analysis University of Washington Biostatistics Working Paper Series 253, Col. Biostat. Res. Archive (2005). The references are hereby incorporated by reference into the present application. Other statistical analysis methods for quantifying biomarkers known in the art can be used as well.

In some embodiments, the RNA levels of CD3$\epsilon$ mRNA, IP-10 mRNA and 18S rRNA are compared to a base line level or a control level observed in non-rejecting organs and may include the level of CD3$\epsilon$ mRNA, IP-10 mRNA and 18S rRNA of the same patient before the organ transplant; the average level of CD3$\epsilon$ mRNA, IP-10 mRNA and 18S rRNA in patients of similar age, gender, race, graft-donor source, Banff histologic grade, or initial anti-rejection treatment as the patient; a value for the level of CD3$\epsilon$ mRNA, IP-10 mRNA and 18S rRNA available in a control population; and/or a value for the level of CD3$\epsilon$ mRNA, IP-10 mRNA and 18S rRNA accepted in the art.

A baseline or control sample can be the level of CD3$\epsilon$ mRNA, IP-10 mRNA and 18S rRNA from a healthy person or a person with a well-functioning (e.g., stable) transplanted organ. A well-functioning (e.g., stable) transplanted organ may be defined as a transplanted organ without acute rejection, and preferably a transplanted organ that has not developed transplant dysfunction or morphologic evidence of transplant injury in areas of the transplant. For example, a stable functioning kidney transplant may be defined as having a serum creatinine concentration that has not changed by more than approximately 0.2 mg per deciliter during the seven days before and the seven days after collection of the biologic specimen for CD3$\epsilon$ mRNA, IP-10 mRNA and 18S rRNA measurements.

It will be understood by those of ordinary skill in the art that it is not necessary to determine the level of CD3$\epsilon$ mRNA, IP-10 mRNA and 18S rRNA in a baseline or control sample every time the method is conducted. For example, the level of CD3$\epsilon$ mRNA, IP-10 mRNA and 18S rRNA in a urinary sample from a subject with a transplanted organ or in a sample from the peripheral blood of the subject can be compared to that of one or more previously determined control samples or to a level recognized by the physician or clinician conducting the method of a consensus of medical and/or clinical practitioners.

In some embodiments, there is provided a method for detecting acute rejection where levels of gene expression are compared to a baseline level of gene expression, which is performed using log-transformed levels of CD3$\epsilon$ mRNA, IP-10 mRNA and 18S rRNA in a urine cell sample and comparing it with log-transformed levels of CD3$\epsilon$ mRNA, IP-10 mRNA and 18S rRNA of a baseline sample from a subject without acute rejection of a transplanted organ. If there is upregulation of RNA levels of CD3$\epsilon$ mRNA, IP-10 mRNA and 18S rRNA from the urine cell sample relative to the baseline level of expression of these genes in the baseline sample, this indicates acute rejection of the transplanted organ. If this is the case, then further steps such as determining the patient's serum creatinine level in peripheral blood, or administering treatment may be indicated. For example, the treatment can include plasmapheresis and/or increased dosages of an anti-rejection agent or a new anti-rejection agent can be added. Anti-rejection agents, include for example, azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD 154, anti-CD3 antibody, thymoglobin, OKT3, corticosteroid, or a combination thereof.

Predicting Kidney Dysfunction (e.g., Acute Transplant Rejection)

A method is described herein for detecting or predicting kidney dysfunction (e.g., acute cellular rejection). Such a method involves: obtaining a biological sample from the subject; determining amounts of CD3$\epsilon$ mRNA, IP-10 mRNA and 18S rRNA in the sample; and comparing the amount of CD3$\epsilon$ mRNA, IP-10 mRNA and 18S rRNA in the sample to a control or baseline amount of CD3$\epsilon$ mRNA, IP-10 mRNA and 18S rRNA, wherein increases between the amount of CD3ε mRNA, IP-10 mRNA and 18S rRNA in the sample relative to the control indicates that the subject can have or can develop kidney dysfunction (e.g., acute cellular rejection).

Any method known to those in the art, as discussed above, can be employed for determining the level of gene expression. Examples include Microarrays, TaqMan® Gene Expression Assays (Applied Biosystems), molecular beacons, scorpions, SYBR Green, and/or RT-PCR. The Example section describes quantitative data obtained by quantitative nucleic acid amplification (e.g., real-time RT-PCR) in a small reaction volume.

Upregulation can be an increase above a control or baseline level of 10%, 15%, 20%, 25%, 30%, 35%, 40%, 45%, 50%, 55%, 60%, 65%, 70%, 75%, 80%, 85%, 90%, 95%, 100% or higher.

In some embodiments, the method of determining gene expression can include normalizing the determined amounts of CD3ε mRNA and IP-10 mRNA against the amount of 18S rRNA in the sample, to generate 18S rRNA-normalized CD3ε mRNA and 18S rRNA-normalized IP-10 mRNA.

In some embodiments, the method of determining gene expression can include log-transforming the determined amounts of CD3ε mRNA, IP-10 mRNA, and 18S rRNA.

In some embodiments, the method of determining gene expression can include log-transforming the determined values of 18S rRNA-normalized CD3ε mRNA, 18S rRNA-normalized IP-10 mRNA, and 18S rRNA.

In some embodiments, the method can include using a logistic regression model to evaluate CD3ε mRNA, IP-10 mRNA, and 18S rRNA expression levels, or a weighted combination of log transformed, normalized RNA levels of CD3ε mRNA, IP-10 mRNA, and 18S rRNA based on a logistic regression model.

The method can detect or predict kidney dysfunction (e.g., acute cellular rejection) a number of days prior to acute rejection. For example, the method can detect or predict kidney dysfunction (e.g., acute cellular rejection) 90 to 60 days before confirmation by biopsy, or 59 to 30 days before confirmation by biopsy, or 29 to 16 days before confirmation by biopsy. Thus, kidney transplant dysfunction such as acute cellular rejection can be predicted about 3 months to about two weeks before it happens. Therefore, this mRNA profile analysis can be a new non-invasive "gold standard" to replace and/or supplement an invasive allograft biopsy.

If an increase in CD3ε mRNA, IP-10 mRNA, and 18S rRNA expression levels is determined, the patient can be informed that there is increased risk of developing transplant rejection. The increased risk varies in different patients, and the organ transplanted. Generally, the increased risk for developing acute rejection is at least about 25%, at least about 50%, at least about 75%, or at least about 90%, or at least about 99% or at least about 100%.

The method can further comprise determining the patient's serum creatinine protein level. The determination of the level of serum creatinine can be made by any method known to those skilled in the art. The next step in this embodiment can include correlating the level of serum creatinine in peripheral blood with predicting acute rejection and eventual loss of the transplanted organ. A significantly greater level of serum creatinine in peripheral blood and increased levels of CD3ε mRNA, IP-10 mRNA, and 18S rRNA in urine correlates with acute rejection and may also increase risk of loss of the transplanted kidney.

Generally, the level of serum creatinine in peripheral blood is considered to be significantly greater if the level is at least about 25% greater than the level of creatinine in a control sample. Commercial kits can be utilized to test creatinine. An example of a commercial kit for determining creatinine level is the QuantiChrom® Creatinine Assay Kit from BioAssay Systems (Hayward, Calif.).

In this embodiment, a control sample is typically the level of serum creatinine in peripheral blood of a healthy person or a person with a well-functioning (e.g., stable) transplant. For example, the normal level of serum creatinine in a healthy person or a person with a well-functioning transplant is generally about 0.8-1.6 milligrams/deciliter. In either case, the person may be the patient or a person different from the patient.

It is not necessary to determine the level of creatinine in a control sample every time the method is conducted. For example, the serum creatinine level from the patient can be compared to that of one or more previously determined control samples or to a level recognized by the physician or clinician conducting the method, or by a consensus of medical and/or clinical practitioners.

In another embodiment, the method further comprises informing medical personnel or the patient about the test results. Information about whether the patient will have acute rejection can also be communicated. If the patient is likely to develop kidney dysfunction, the patient can be prescribed and/or administered a treatment to delay rejection of the transplanted organ. Such treatment can include increased or decreased dose of an anti-rejection agent or an anti-rejection agent can be added. Anti-rejection agents, include for example, azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD 154, anti-CD3 antibody, thymoglobin, OKT3, corticosteroid, or a combination thereof.

For example, if acute rejection is predicted, a steroid pulse therapy can be started and may include the administration for three to six days of a high dose corticosteroid (e.g., greater than 100 mg). An antibody can be added. An example of an antibody therapy includes the administration for seven to fourteen days of the polyclonal antibody Thymoglobin or the monoclonal antibody, OT3.

Another example of a treatment that can be administered is plasmapheresis. Plasmapheresis is a process in which the fluid part of the blood (i.e., plasma) is removed from blood cells. Typically, the plasma is removed by a device known as a cell separator. The cells are generally returned to the person undergoing treatment, while the plasma, which contains antibodies, is discarded.

In some embodiments, the method for predicting acute rejection employs log-transformed RNA values determined from an urine sample and that are determined by combinations of log transformed and/or normalized RNA values using a logistic regression model of CD3ε mRNA, IP-10 mRNA, and 18S rRNA expression levels, which predict acute rejection of the transplanted organ within about 90 to about 60 days after the urine sample is tested. In some embodiments, the log-transformed RNA levels of the urine sample are determined by combinations of log transformed, normalized RNA levels using a logistic regression model of CD3ε mRNA, IP-10 mRNA, and 18S rRNA expression levels that predicts acute rejection of the transplanted organ in about 59 to about 30 days after the urine sample is tested. In some embodiments, the log-transformed RNA levels of the urine sample are determined by combinations of log transformed, normalized CD3ε mRNA, IP-10 mRNA, and 18S rRNA expression levels that predict acute rejection of the transplanted organ in about 29 to about 15 days after the urine sample is tested.

Quantified expression levels of 18S rRNA-normalized CD3ε mRNA, 18S rRNA-normalized IP-10 mRNA, and 18S rRNA can be used in the diagnostic signature algorithm provided herein. In some instances, the values of 18S-normalized CD3ε mRNA, 18S-normalized IP-10 mRNA and 18S rRNA can deviate from a normal distribution (P<0.001). $\log_{10}$-transformation of these values can substantially reduce this deviation.

Moreover, 18S rRNA can be expressed at higher levels than CD3ε mRNA and IP-10 mRNA. Hence, the quantified amount of 18S rRNA in the diagnostic signature algorithm is adjusted by a factor of $10^{-6}$ to allow better relationship between the expression levels of these three genes.

Diagnostic Signature

A diagnostic signature algorithm is provided herein as follows that can be employed in a method for detecting, monitoring and diagnosing kidney function from a urine sample obtained from a subject. The method for detecting developing or existing dysfunction or rejection of a kidney transplant in a subject from a urine sample obtained from the subject involves:

(a) determining an absolute urinary CD3ε mRNA copy number per microgram of total RNA in the urine sample;
(b) determining an absolute urinary IP-10 mRNA copy number per microgram of total RNA in the urine sample;
(c) determining an absolute urinary 18S rRNA copy number per microgram of total RNA times $10^{-6}$ in the urine sample;
(d) ascertaining a diagnostic signature of developing or existing dysfunction or rejection of a kidney transplant in the subject with the following algorithm:

$$\text{signature} = -6.1487 + 0.8534 \log_{10}(CD3\varepsilon/18S) + 0.6376 \log_{10}(IP\text{-}10/18S) + 1.6464 \log_{10}(18S)$$

where:
CD3ε is the absolute urinary CD3ε mRNA copy number per microgram of total RNA in the urine sample;
IP-10 is the absolute urinary IP-10 mRNA copy number per microgram of total RNA in the urine sample; and
18S is the an absolute urinary 18S rRNA copy number per microgram of total RNA in the urine sample times $10^{-6}$;
to thereby detect a developing or existing dysfunction or rejection of a kidney transplant in the subject.

The RNA expression levels are determined as described herein, or using other procedures available to those of skill in the art.

When the value of the diagnostic signature is below a threshold of −1.213 (or −1.21) the subject is not prone to development of tissue rejection. However, when testing of a subject's urine sample is above a threshold of −1.213 (or −1.21) treatment of the subject for tissue rejection is indicated.

This model was developed via logistic regression analysis to identify parsimonious subsets of the eight mRNA measures—CD3ε, perforin, granzyme B, PI-9, CD103, IP-10, CXCR3, and TGF-β1—and 18S rRNA from matched urine samples that discriminated the acute cellular rejection biopsies from No Rejection biopsies. Acute cellular rejection was defined as Banff Grade 1A or higher and No Rejection biopsies were those classified by the on-site pathologist as showing no histological features of rejection. From those models in which each predictor was significant at P<0.05, one with the greatest log-likelihood and greatest area under the receiver-operating-characteristic (ROC) curve was provisionally selected as the best-fitting model. The regression estimates from this model defined a diagnostic signature, and area under the curve (AUC), sensitivity, and specificity were used to evaluate the ability of this signature to discriminate ACR biopsies from No Rejection biopsies.

The model was validated in several ways. The generalizability of the fitted model to other data sets was evaluated using bootstrap re-sampling methods. Logistic regression with backwards elimination was used to identify the best subset of the mRNA measures and 18S rRNA in each of 500 data sets obtained by sampling with replacement from the original data set. The best subset model was then fit to 500 additional bootstrap samples from which optimism-adjusted measures of discrimination (i.e., AUC) and model fit (i.e., Cox's intercept and slope) and a LOESS-smoothed calibration plot, were obtained (LOESS: locally estimated scatter-plot smoothing).

Figure 3A:
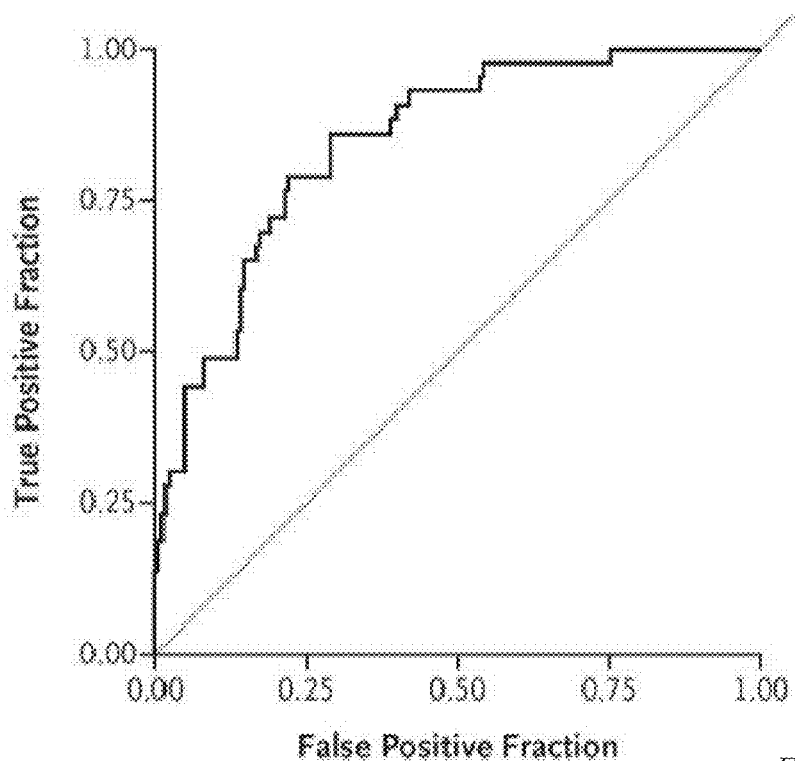
FIG. 3A-3D shows Receiver-Operator-Characteristic Curves and a Calibration Curve for the Diagnostic Signature. The fraction of true positive results (sensitivity) and false positive results (1-specificity) for the diagnostic signature (calculated from 18S-normalized CD3ε mRNA, 18S-normalized IP-10 mRNA and 18S rRNA, all logged) as biomarker of acute cellular rejection in CTOT-04 subjects are shown in FIG. 3A and FIG. 3B, and the calibration plot based on bootstrap validation is shown in FIG. 3C. The area under the curve (AUC) was 0.85 (95% CI: 0.78-0.91) for acute cellular rejection vs. No Rejection Biopsy group (FIG. 3A) and 0.81 (95% CI: 0.75-0.87) for acute cellular rejection vs. Stable (no biopsy) group (FIG. 3B). Adding 18S-normalized perforin to the best-fitting model provided no additional improvement, largely because perforin was very highly correlated with CD3ε. Alternative combinations of mRNA for perforin and IP-10 or perforin and CD3ε also predicted acute cellular rejection accurately; the AUCs were 0.84 (95% CI: 0.78-0.90; P<0.0001) for the combination of 18S-normalized perforin mRNA, 18S-normalized IP-10 mRNA and 18S rRNA, and 0.84 (95% CI: 0.76-0.91; P<0.0001) for the combination of 18S-normalized-CD3ε mRNA, 18S-normalized-perforin mRNA and 18S rRNA. Bootstrap validation confirmed the optimal model as including 18S-normalized CD3ε mRNA, 18S-normalized IP-10 mRNA and 18S rRNA as predictors. Optimism-corrected estimates of the AUC, Cox's intercept and slope statistics were (respectively): 0.83, -0.06, and 0.92. The LOESS-smoothed estimates of the calibration curves of the optimism-adjusted and the unadjusted calibration curves are overlaid on a diagonal reference line that represents perfect model calibration (FIG. 3C). None of the single-marker models calibrated as well as the 3-gene model. Based on these results, the 3-gene model of 18S-normalized CD3ε mRNA, 18S-normalized IP-10 mRNA and 18S rRNA, all logged, is superior to any of the single-gene models considered and the three-gene diagnostic signature can be expected to perform well in an independent population of patients. The ROC curve showing how well the 3-gene signature discriminated acute cellular rejection biopsies from No Rejection biopsies in the CTOT-01 external validation set had an AUC of 0.74 (95% CI: 0.61 to 0.86, P=0.0002) (FIG. 3D). This AUC was lower than the CTOT-04 AUC of 0.85 (FIG. 3A), but not significantly lower (P=0.13). Among the 71 CTOT-01 cDNA samples assayed for the levels of transcripts included in the diagnostic signature, 21 subjects provided 24 samples with Banff acute cellular rejection grade IA or higher and 43 subjects provided the remaining 47 samples with No Rejection biopsies (biopsies without acute cellular rejection, antibody mediated rejection (AMR) or Borderline changes). Of the 24 acute cellular rejection biopsies, 11 were classified as Banff acute cellular rejection grade IA, 4 as IB, 7 as IIA, 1 as IIB, and 1 as grade III and these resulted from 17 for-cause biopsies and 7 surveillance biopsies. Of the 47 non-acute cellular rejection biopsies, 19 were for-cause biopsies and 28 were surveillance biopsies.
Figure 3B:
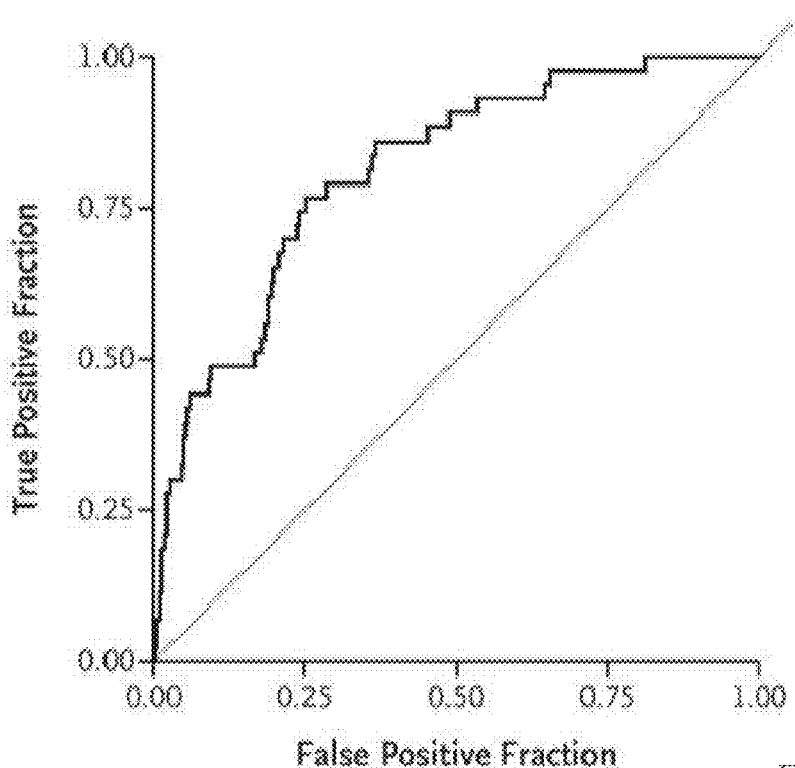

ROC curve analysis showed that this 3-gene signature yielded an AUC of 0.85 (95% confidence interval [CI] 0.78 to 0.91, P<0.0001). Using the cutpoint of −1.213, which maximizes Youden's index, this diagnostic signature has 79% sensitivity and 78% specificity to discriminate ACR biopsies from No Rejection biopsies (FIG. 3A). The Hosmer-Lemeshow test indicated an excellent fit of this model to the data (chi-square $\chi^2$=4.84, with 8 df, and P=0.77). The 3-gene signature also discriminated between the group of patients with biopsy specimens showing acute cellular rejection and the group of patients with stable graft function who did not undergo biopsy (FIG. 3B).

Figure 3C:
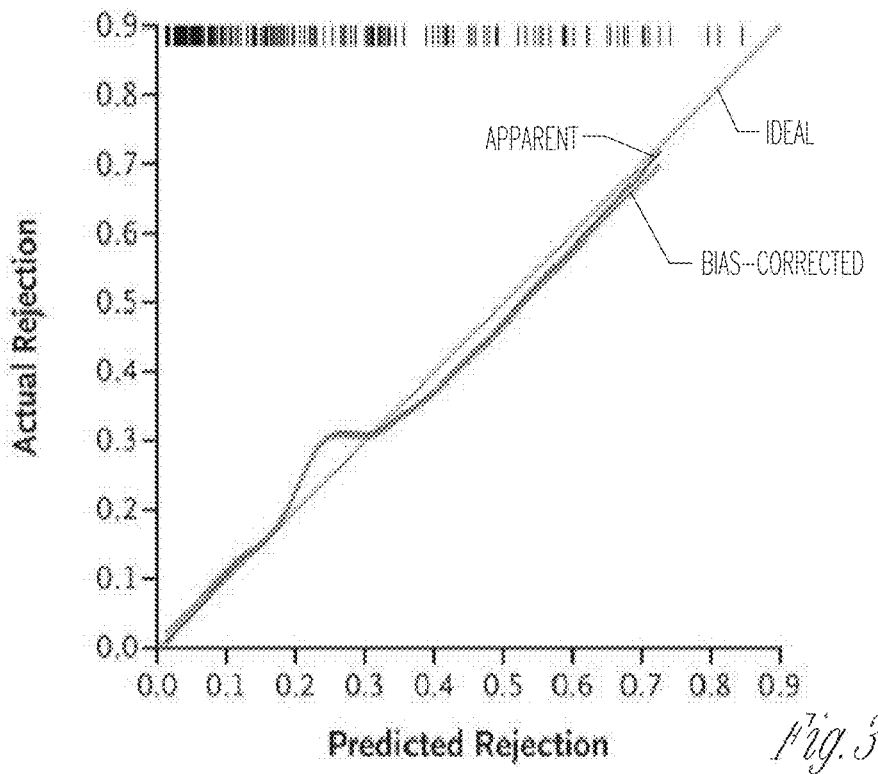

Bootstrap validation of this three-gene model yielded a cross-validated estimate of the AUC of 0.83, which is an estimate of the expected value of the AUC in independent samples (i.e., samples not used to derive the diagnostic signature). The calibration-curve intercept and slope of −0.06 and 0.92, respectively, revealed that the predicted probabilities of a biopsy showing acute cellular rejection, across the range of the diagnostic signature, tended to be only very slightly higher than the actual probabilities (FIG. 3C) and that the likelihood that the model was overfitted was small. The loess-smoothed estimates of the unadjusted and cross-validated calibration curves were overlaid on a diagonal reference line representing perfect model calibration (FIG. 3C). The close correspondence of the two curves to the reference line shows excellent fit and reflects the above interpretation of the intercept and slope estimates of the calibration curve.

External Validation

Among the 71 complementary DNA (cDNA) samples assayed for the levels of transcripts included in the diagnostic signature, 24 samples (from 21 patients) showed acute cellular rejection and 47 samples (from 43 patients) showed no rejection. Of the 24 specimens showing acute cellular rejection (from 17 for-cause and 7 surveillance biopsies), 11 were classified as Banff grade IA, 4 as grade IB, 7 as grade IIA, 1 as grade IIB, and 1 as grade III. Of the 47 biopsy specimens not showing acute cellular rejection, 19 were from for-cause biopsies and 28 from surveillance biopsies. Among the 71 specimens constituting the external-validation data set, the 36 for-cause biopsy specimens were from seven of the eight clinical sites that participated in the CTOT-01 study, and the 35 surveillance biopsy specimens were from five of these eight sites.

Figure 3D:
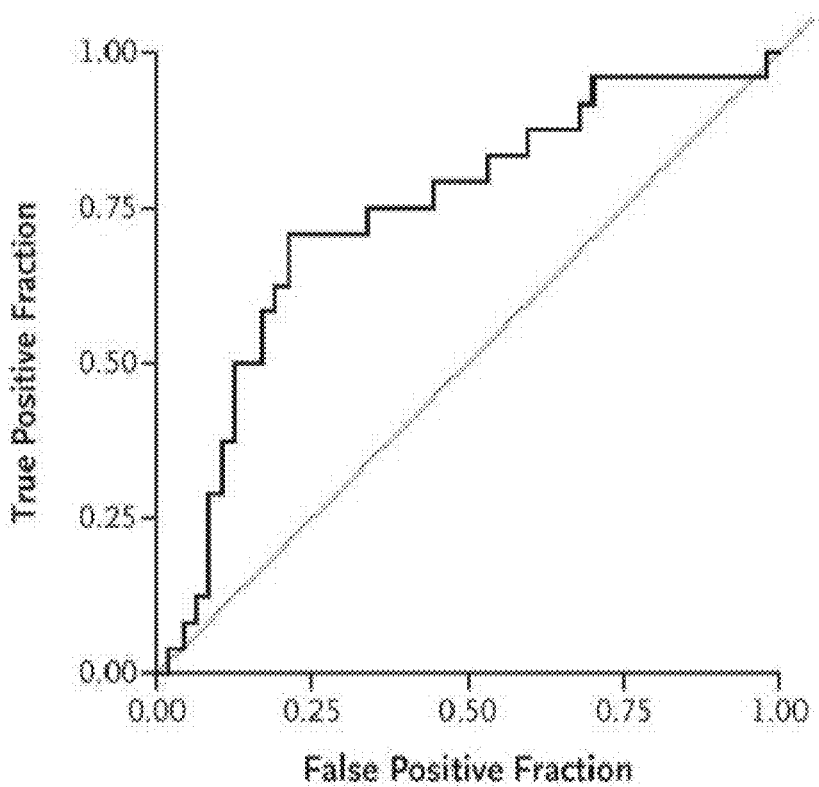

The ROC curve of the three-gene signature discriminating between biopsy specimens showing acute cellular rejection and those showing no rejection in the external-validation data set had an AUC of 0.74 (95% CI, 0.61 to 0.86; P<0.001) (FIG. 3D). This AUC was lower than the AUC of 0.85 (95% CI, 0.78 to 0.91; P<0.001) in the CTOT-04 data set (FIG. 3A), but the difference between the two AUCs was not significant (P=0.13). With the use of the cutoff value of −1.213 for the diagnostic signature in the CTOT-04 study, acute cellular rejection in the external validation data set was predicted with a specificity of 72% (95% CI, 62 to 83) and a sensitivity of 71% (95% CI, 53 to 89), values that were also lower than those in the CTOT-04 data set but not significantly (P>0.35 for both comparisons).

Prospective Trajectory of Diagnostic Signature

FIG. 5 displays the loess-smoothed, average within-person prospective trajectories of the diagnostic signature (i.e., trajectories of the signature as a function of the time since transplantation), with 95% confidence intervals, in the three groups of patients. The trajectories for the group of patients with specimens showing no rejection and for the group of patients with stable graft function and no biopsy were flat and remained below the −1.213 threshold that was diagnostic of acute cellular rejection throughout the first 400 days after transplantation. However, a progressive increase in the diagnostic score was seen in the urine samples from patients in whom acute cellular rejection developed.

Thus, even after the exclusion of all urine samples obtained after the development of acute cellular rejection and those that were matched to biopsy specimens showing acute cellular rejection and had been used to develop the diagnostic signature, there was a clear signal by approximately 80 days after transplantation that values were elevated in patients in whom acute cellular rejection subsequently developed. After approximately 160 days, the average value for the patients in whom acute cellular rejection subsequently developed was greater than or equal to the threshold level that was diagnostic for acute cellular rejection (FIG. 5D).

Retrospective Trajectory of Diagnostic Signature

Figure 4A:
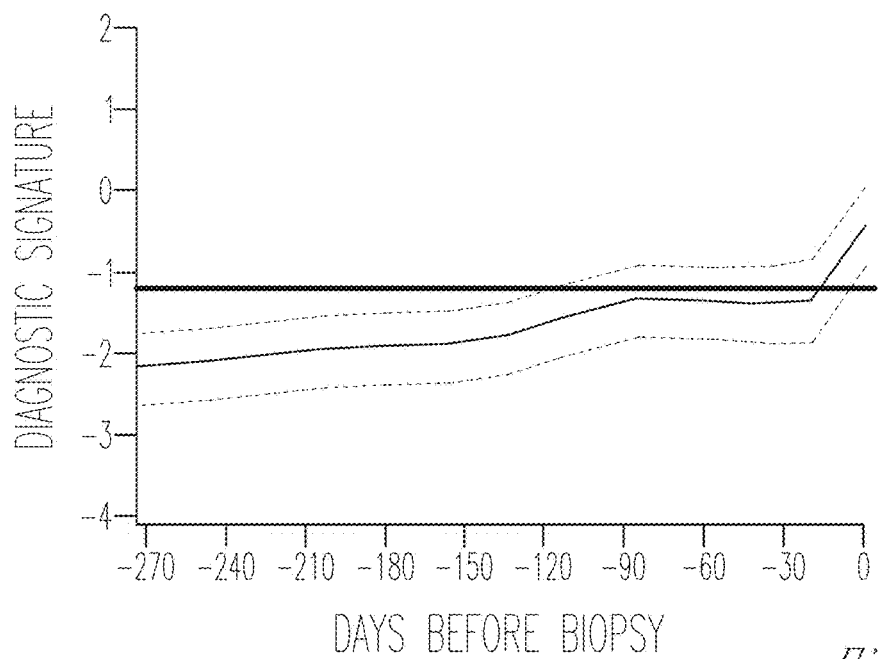
FIG. 4A-4D illustrate the average within-person retrospective trajectory of the diagnostic signature (i.e., the trajectory as a function of the time before biopsy) in urine samples obtained at or before biopsy that passed quality control. The data shown are for the group of 38 patients with first biopsy specimens showing acute cellular rejection (201 urine samples) (FIG. 4A) and the group of 113 patients with specimens showing no rejection (833 urine samples) (FIG. 4B). Only specimens obtained during the first 400 days after transplantation were included. The diagnostic signature remained relatively flat and well below the -1.213 threshold that was diagnostic of acute cellular rejection during the 270 days before biopsy in the group of patients with findings showing no rejection (FIG. 4C). There was a significant difference in the trajectories between the two groups, with a marked increase in the diagnostic signature during the 20-day period before the first specimen showing acute cellular rejection (P<0.001) (FIG. 4D). The y-axis values are diagnostic-signature scores without intrinsic units of measurement; they were calculated from the logistic-regression equation (-6.1487+0.8534 log 10[CD3ε/18S]+0.6376 log 10[IP-10/18S]+1.6464 log 10[18S]) as follows. Absolute levels of CD3ε mRNA, IP-10 mRNA, and 18S rRNA in the cells from each urine sample were measured by polymerase-chain-reaction assay, with the units of measurement being copies per microgram of total RNA for each mRNA measure and copies ($\times 10^{-6}$) per microgram of total RNA for 18S rRNA. The mRNA copy numbers were 18S-normalized by dividing the mRNA copy number by the 18S rRNA copy number in the same sample, and the ratio was log 10-transformed. In all the panels, the central lines indicate the trajectory, the related dashed lines show the 95% confidence interval, and the straight lines at about -1.2 the diagnostic threshold.
Figure 4B:
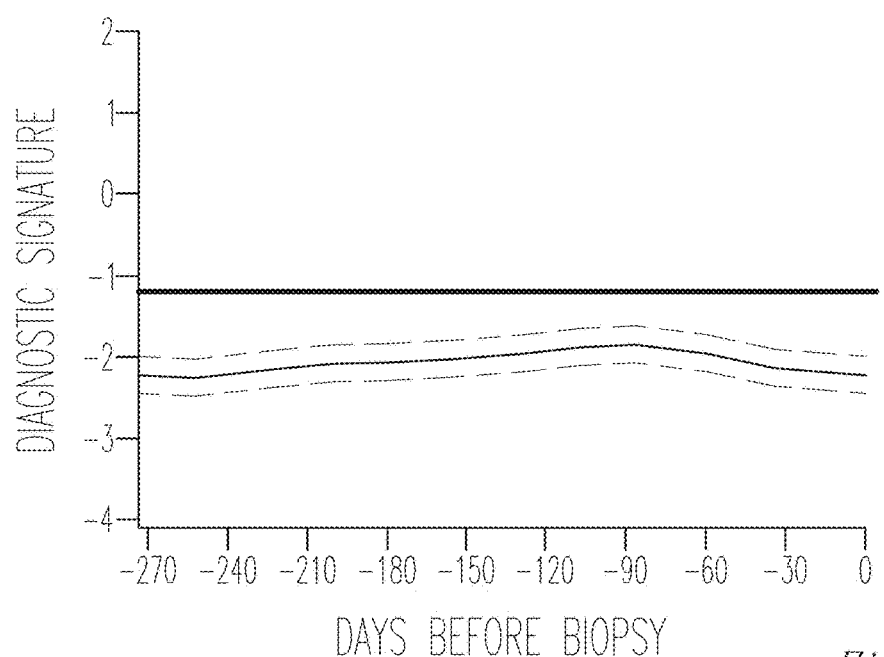
Figure 4C:
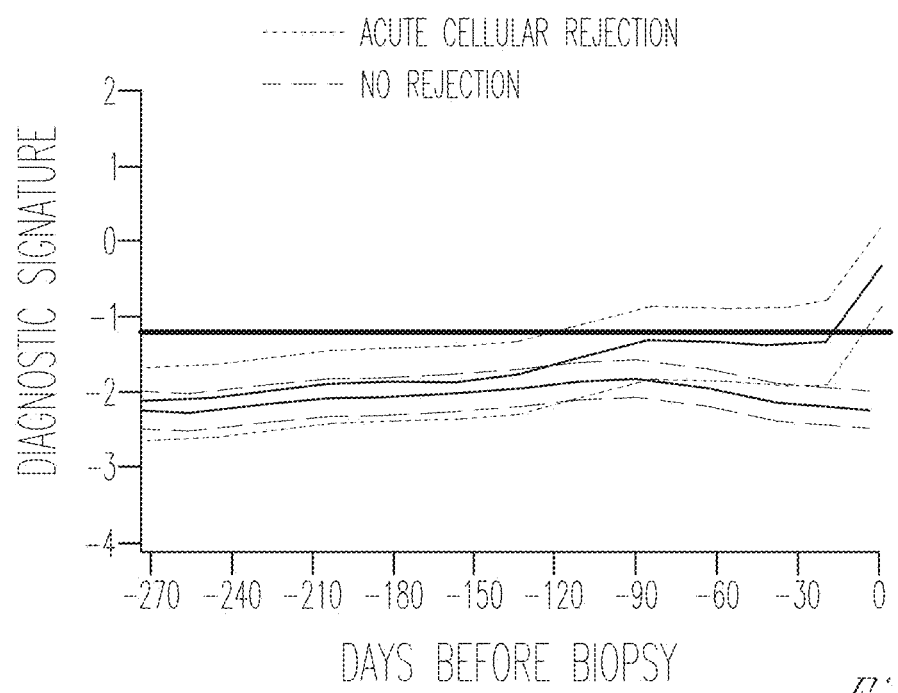
Figure 4D:
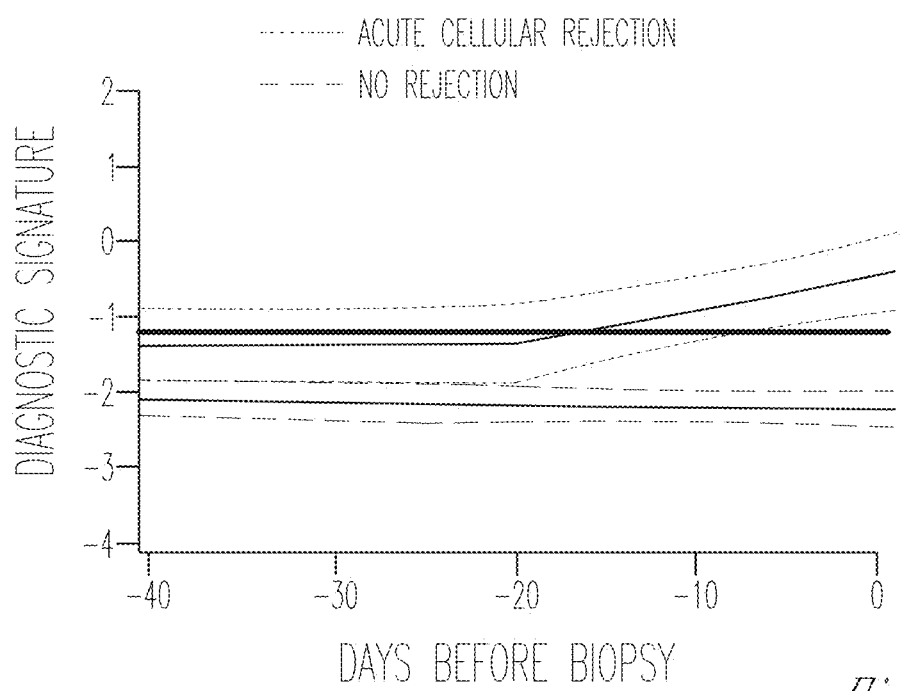

FIG. 4 shows the loess-smoothed, average within-person retrospective trajectories of the diagnostic signature (i.e., trajectories of the signature as a function of the time before biopsy), with 95% confidence intervals, for the group of patients with biopsy specimens showing acute cellular rejection (FIG. 4A) and the group with specimens showing no rejection (FIG. 4B). There was a significant difference between the trajectories for the two groups, with the signature remaining flat and well below the diagnostic threshold during the 270 days preceding a biopsy in the group with specimens showing no rejection, whereas a marked increase was observed in the diagnostic signature during the 20-day period leading up to the first specimen showing acute cellular rejection (FIGS. 4C and 4D) (P<0.001).

Additional Features

When urine samples matched to biopsy specimens showing acute cellular rejection were compared with urine samples matched to biopsy specimens showing borderline changes, acute antibody-mediated rejection, or chronic allograft nephropathy, the signature was diagnostic of acute cellular rejection with 71% specificity (95% confidence interval, 55 to 87) and 79% sensitivity (95% confidence interval, 67 to 91) (AUC, 0.78; 95% confidence interval, 0.68 to 0.89; P<0.001). The signature was diagnostic in patients who underwent for-cause biopsies as well as in those who underwent surveillance biopsies and was similarly diagnostic across transplantation sites (the site-by-signature interaction was not significant, P=0.30). The score of the diagnostic signature decreased after antirejection therapy for acute cellular rejection (P=0.05), but it was not associated with the Banff grade for acute cellular rejection (P=0.83) (Table 6 in the Examples). The urine samples from patients who received induction therapy with interleukin-2 receptor antibodies, as compared with those from patients who received T-cell-depleting antibodies, had a higher diagnostic score (P<0.001) (FIG. 6A-6C), especially during the first month after transplantation, but the signature was diagnostic of acute cellular rejection with either type of induction therapy.

The diagnostic signature was not associated with urinary tract infection (P=0.69), blood infection (P=0.94), or CMV infection (P=0.56) but was associated with BKV infection (P=0.03). The mean diagnostic score at 4 to 6 months was associated with a decline of 30% or more in renal allograft function from 6 to 12 months (odds ratio, 2.66; 95% CI, 1.45 to 4.87; P=0.002).

CD3ε mRNA, IP-10 mRNA and 18S rRNA are Sufficient

The rationale for not including perforin or granzyme B in the Diagnostic Signature was as follows. The inclusion of granzyme B and/or perforin was not able to significantly improve the diagnostic signature based on IP-10, CD3ε and 18S, due largely to the high correlations between the levels of CD3ε mRNA and the levels of granzyme B mRNA or perforin mRNA. The inclusion of granzyme B and/or perforin being unable to significantly improve the diagnostic signature should not detract from the fact that when considered alone, 18S-normalized levels of granzyme B and perforin are strongly associated with acute cellular rejection in the CTOT-04 study. Also, and as provided in the description of FIG. 3, the AUC for the combination of 18S-normalized perforin mRNA, 18S rRNA-normalized IP-10 mRNA and 18S rRNA was 0.84 (95% CI: 0.78 to 0.90; P<0.0001), only slightly lower than that of the final diagnostic signature, and this combination discriminated acute cellular rejection biopsies with a sensitivity of 77% and a specificity of 76%. Importantly, this signature correlated very highly (r=0.93) with the optimal 3-gene diagnostic signature (18S-normalized CD3ε mRNA, 18S-normalized IP-10 mRNA and 18S rRNA, all logged).

The data show that the signature is diagnostic for acute cellular rejection and distinguishes those with acute cellular rejection from patients with other types of rejection such as borderline rejection and acute antibody mediated rejection. These findings are of considerable clinical significance. The finding that the diagnostic signature score is marginally higher in Banff acute cellular rejection grade I compared to grades II or III is consistent with Banff grade I acute cellular rejection being primarily interstitial cell infiltration and tubulitis wherein relatively more cells would be expected to have access to urine compared to grade II/III acute cellular rejection which are characterized by mild to moderate intimal arteritis (grade II) or by transmural arteritis and/or arterial fibrinoid change and necrosis of medial smooth cells with accompanying lymphocytic vascular inflammation (grade III) wherein the brunt of the injury is borne by the arterial vessel wall.

The rationale for the thresholds used to qualify RNA in the CTOT-04 Study is as follows. A RNA sample was classified as quality control passed if the 18S rRNA copy number was greater than or equal to $5.0 \times 10^7$ per microgram of total RNA and its TGF-β1 mRNA copy number was greater than or equal to 100 copies per microgram of total RNA; 3559 (83%) urine samples passed both criteria. The rational for these thresholds included the following; during the development of our urinary cell mRNA profiling protocol, one of the challenges we faced was to ensure that there were indeed measurable cellular mRNAs in the total RNA isolated from the urinary cells. Existing parameters for assessing RNA quality such as RNA integrity number and the A260/280 ratio primarily assess integrity of total RNA rather than directly assess mRNA integrity. An mRNA integrity parameter was introduced to guarantee that there was cellular mRNA in a given urine specimen and the ubiquitously expressed TGF-β1 mRNA was chosen for this role.

Although the precise abundance of TGF-β1 copy number in human peripheral blood cells or renal tubular cells is not known, the inventors reasoned that the detection of 100 copies of TGF-β1 in the 2.5 µl cDNA used in the PCR assay would ensure that mRNA from about 10 urinary cells was indeed present. As reported by Zhang et al. (Science 276: 1268-72 (1997)) the abundance of most human mRNAs is 5 to 50 copies per cell. Moreover, the standard curve in the PCR assays was constructed using 25, 250, 2500, 25,000, 250,000 and $2.5 \times 10^6$ copies of the engineered Bak amplicon, and 100 copies were within the range of our standard curve and the $C_T$ in duplicate wells showing less than 0.5 $C_T$ difference.

Ribosomal RNA constitutes about 80-85% of the total cellular RNA and is more stable compared to mRNA. The inventors used $5 \times 10^7$ 18S ribosomal RNA copies per microgram of total RNA as an additional cutoff point to qualify a urine specimen. A threshold of $5 \times 10^7$ copies of rRNA ensured that 25,000 rRNA copies (rRNA from about 10 cells in view of data showing that 2501 copies of 18S rRNA are typically present in a single human peripheral blood mononuclear cell) were present in the 2.5 ul cDNA used in 1:2000 dilutions for measuring 18S rRNA abundance in the PCR assay.

Among the 4300 urine specimens profiled, 3559 (83.3%) urine specimens were classified as quality control passed based on TGF-β1 mRNA copy number being greater than or equal to 100 copies per microgram of total RNA and their 18S rRNA copy number being greater than or equal to $5 \times 10^7$ per microgram of total RNA. The developing reasons for the 17% of urine samples not passing copy number thresholds include: (i) paucity of cells in the urine specimen; (ii) the innate poor stability of mRNA and the low abundance (<50 copies) of the majority of mRNAs in the mRNA pool; and (iii) isolation of RNA from stored and shipped urine cell pellets. A more precise characterization of the urine specimens in this study might be "urine specimens with intact mRNA for measurement" and "urine specimens without intact RNA for measurement" rather than the terminology "QC-passed/failed" which could be incorrectly interpreted as technical/laboratory related reasons for not meeting the thresholds.

In a post hoc analysis, the inventors went back and determined the frequency of quantifiable mRNA for CD3ε, perforin, granzyme B, IP-10, CXCR3, CD103, or PI-9 (the mRNAs pre-specified for measurement in the CTOT-04 protocol) in the urine specimens classified as QC-failed based on TGF-β1 and 18S rRNA copy number thresholds. This analysis showed that more than 95% of the 741 QC-failed specimens had less than 100 copies of these mRNAs.

The rationale for the use of 18S rRNA to normalize mRNA is as follows. The strategy of absolute quantification of mRNA abundance rather than relative quantification (wherein the reference gene abundance is integral to the calculation of target gene abundance) facilitated the identification that 18S rRNA levels are higher in urine specimens from the acute cellular rejection biopsy group compared to the No Rejection biopsy group or the Stable (no biopsy) group. One consequence of 18S rRNA levels being higher is that 18S rRNA normalization of the target leads to underestimation of the increase in the target gene abundance in urine specimens from the acute cellular rejection biopsy group. This was seen from the finding that that the levels of CD103 (P<0.0001), CXCR3 (P<0.0001), PI-9 (P=0.002) and TGF-β1 (P=0.0001) are all significantly different between the acute cellular rejection biopsy group and the No Rejection biopsy group when non-normalized levels are used (Table 5B, analysis using non-normalized levels).

The reasons for the use of 18S rRNA levels to normalize target gene levels include: (i) to ensure that the differences in the levels of a target gene between the acute cellular rejection biopsy group and the No Rejection biopsy group or Stable (no biopsy) group are not due to reasons such as variations in RNA integrity and reverse transcription efficiency, with normalization serving as an internal control; and (ii) to demonstrate that increased levels of specific mRNAs (e.g., IP-10) in association with acute cellular rejection are above and beyond the increase in the transcriptional machinery of the cell from which the total RNA was isolated. The data provided in Table 5B show that 18S rRNA levels are about 2-fold higher in the acute cellular rejection biopsy group compared to the No Rejection biopsy group or the Stable (no biopsy) group (similar to the increases seen in CD103, CXCR3, PI-9, and TGF-β1) whereas the levels of mRNA for CD3ε, granzyme B, perforin and IP-10 are 10-fold higher or more in the acute cellular rejection biopsy group compared to the No Rejection biopsy group or the Stable (no biopsy) group. Also, scholarly guidelines on the reporting of real-time PCR experiments consider normalization to be an "essential component of a reliable PCR assay" (The MIQE Guidelines: Minimum Information for Publication of Quantitative Real-Time PCR Experiments; Bustin et al., Clin Chem 55:611-22 (2009)).

The basis for 18S rRNA levels being about 2-fold higher in the acute cellular rejection biopsy group compared to the No Rejection biopsy group or the Stable (no biopsy) group may reflect more than cell activation alone. It is however unlikely that the increase is due to a higher number of cells since irrespective of the RNA yield from a given cell pellet, reverse transcription of RNA to cDNA is adjusted to result in a final concentration of 1.0 microgram of cDNA in 100 µA solution prior to measurement of transcript abundance. This normalization of RNA yield from different urinary cell pellets, that is one urine cell pellet containing $1 \times 10^6$ urinary cells yielding a higher amount of RNA compared to another urinary cell pellet containing $1 \times 10^5$ urinary cells, would tend to minimize the cell number dependent differences in 18S rRNA abundance and for that matter all of the mRNAs measured in this study. On the other hand, differences in the types of cells contributing to the cell pellet could contribute to differences in transcript abundance. It is known that 18S rRNA abundance is lower in highly differentiated cells compared to less differentiated cells (Lodish, Annual Review of Biochemistry 45:39-72 (1976)), and a urine cell pellet that contains mostly highly differentiated renal tubular cells compared to a cell pellet that contains mostly activated lymphocytes would be expected to have lesser amounts of 18S rRNA.

The implications of immunosuppressive therapy relating to the Diagnostic Signature are as follows. The lower trajectory (lower diagnostic score) in those induced with T cell depleting antibodies compared to subjects induced with non-depleting antibodies is consistent with T cell depleting antibodies inducing a greater degree of immunosuppression and being associated with a lower incidence of acute rejection as compared to IL-2 receptor antagonists. The findings described herein, in addition to suggesting a mechanistic basis for the lower incidence of acute rejection for induction with depleting antibodies vs. non-depleting antibodies, indicate that the signature can serve as an accurate indicator of the kidney graft recipient's immune status and help personalize immunosuppressive therapy.

The impact of anti-rejection therapy on the diagnostic signature is as follows. A comparison of the diagnostic signature values showed a significant decrease following treatment of an episode of acute cellular rejection. While this decrease in the mean value of the diagnostic signature remained statistically significant in the subset of patients who responded to therapy, almost 30% of the responders did not show a numerical decrease in the diagnostic signature. (The number of non-responders to acute cellular rejection treatment [N=4] was too small to yield meaningful results.) These findings indicate that a successful clinical response is associated with a reduction or normalization of the signature in many, but not in all cases. This lack of complete resolution of the molecular signature is reminiscent of the previously published finding wherein almost two-thirds of kidney graft recipients with clinical reversal of acute rejection had residual inflammation in their follow-up graft biopsies (Gaber et al., Kidney Int 55:2415-22 (1999)). In the U.S. double blind, randomized, multicenter, phase III clinical trial of Thymoglobulin versus ATGAM in the treatment of acute graft rejection episodes after renal transplantation, a subset of patients (n=38) had both a baseline inclusion biopsy and a protocol biopsy one to two weeks following the end of therapy and it was found that "treatment was clinically successful in 94% of patients receiving Thymoglobulin and in 79% of patients receiving ATGAM, but only 35% and 33% of the respective biopsies demonstrated total resolution of the rejection on the repeat biopsies" (Gaber et al., Kidney Int 55:2415-22 (1999)).

The implications of infections upon the Diagnostic Signature are as follows. The data demonstrate that urinary tract infection, blood infection and CMV are not associated with the diagnostic score, giving strong assurance that these types of infections will not impact the diagnostic accuracy of the signature. Thus, these infections will not increase the diagnostic signature score and result in a false positive acute cellular rejection diagnosis. On the other hand, the association of BKV infection with the signature suggests that the presence or absence of BKV infections needs to be confirmed prior to ascribing an elevated diagnostic signature score to acute cellular rejection. In the clinical setting, this can and should be accomplished by screening for BKV in blood or urine, a routine clinical practice in many transplant centers.

Kits

The methods can also be performed by use of kits that are described herein. In general, kits can include a detection reagent that is suitable for detecting the presence of an RNA of interest.

The kits can include a panel of probe and/or primer sets. Such probe and/or primer sets are designed to detect expression of one or more genes and provide information about the rejection of a graft. Preferred probe sets comprise probes or primers that can be labeled (e.g., fluorescer, quencher, etc.). Unlabeled probes or primers can also be provided in the kits.

The probes and primers are useful for detection of CD3ε mRNA, IP-10 mRNA, and 18S rRNA. The probe and/or primer sets are targeted at the detection of gene transcripts that are informative about acute rejection. Probe and/or primer sets may also comprise a large or small number of probes or primers that detect gene transcripts that are not informative about transplant rejection. Such probes and primers are useful as controls and for normalization. Probe and/or primer sets can be provided in the kits as a dry material or dissolved in solution. In some embodiments, probe and/or primer sets can be affixed to a solid substrate to form an array of probes. Probe and/or primer sets can be configured for multiplex PCR. The probes and/or primers can be nucleic acids (e.g., DNA, RNA, chemically modified forms of DNA and RNA), LNA, or PNA, or any other polymeric compound capable of specifically interacting with the desired nucleic acid sequences.

The kits can include components for isolating and/or detecting mRNA in essentially any sample (e.g., urine, blood, etc.), and a wide variety of reagents and methods are, in view of this specification, known in the art. Hence, the kits can include vials, swabs, needles, syringes, labels, pens, pencils, or combinations thereof.

Commercially available components can also be included in the kits.

For example, the kit can include components from QIAGEN, which manufactures a number of components for RNA isolation, including RNEASY, a Total RNA System (involving binding total RNA to a silica-gel-based membrane and spinning the RNA); OLIGOTEX® for isolation of RNA utilizing spherical latex particles; and QIAGEN total RNA kit for In Vitro Transcripts and RNA clean-up.

The kits can include components for a fluorescence based real-time detection method. For example, the kits can include primers for generating cDNA and/or for amplification of mRNA and rRNA. The kits can include components for 5' nuclease assays employ oligonucleotide probes labeled with at least one fluorescer and at least one quencher. Prior to cleavage of the probe, the fluorescer excites the quencher(s) rather than producing a detectable fluorescence emission. The oligonucleotide probe hybridizes to a target oligonucleotide sequence for amplification in PCR. The nuclease activity of the polymerase used to catalyze the amplification of the primers of the target sequence serves to cleave the probe, thereby causing at least one fluorescer to be spatially separated from the quencher so that the signal from the fluorescer is no longer quenched. A change in fluorescence of the fluorescer and/or a change in fluorescence of the quencher due to the oligonucleotide probe being digested can be used to indicate the amplification of the target oligonucleotide sequence. Although some primers and probes are described in Table 4, other suitable primers and probes can be employed. Probes and primers can be designed using techniques available to those of skill in the art.

The kits can also include any of the following components: materials for obtaining a sample, enzymes, buffers, probes, primers for generating cDNA, primers for amplifying RNA or cDNA, materials for labeling nucleic acids, microarrays, one or more microarray reader, competitor nucleic acids, probes and/or primers for a housekeeping gene for normalization, control nucleic acids, and antibodies.

In further embodiments, kits can include a urine collection system. Urine collection systems can include essentially any material useful for obtaining and/or holding a urine sample. Urine collection systems may include, for example, tubing, a beaker, a flask, a vial, a test tube, a container, and/or a lid for a vial, test tube or container (e.g., a plastic container with a snap-on or screw top lid).

In certain embodiments, kits can also include a urine presentation system. A urine presentation system can include essentially any material that is useful for presenting the urine to be contacted with the appropriate detection or purification reagents. A urine presentation system may comprise, for example, a sample well, which may be part of a multi-well plate, a petri dish, a filter (e.g., paper, nylon, nitrocellulose, PVDF, cellulose, silica, phosphocellulose, or other solid or fibrous surface), a microchannel (which may be part of a microchannel array or a microfluidics device), a small tube such as a thin-walled PCR tube or a 1.5 ml plastic tube, a microarray to which urine or material obtained from urine may be applied, a capillary tube or a flat or curved surface with detection reagent adhered thereto, or a flat or curved surface with material that adheres to proteins or nucleic acids present in the urine sample.

Kits can include probes that may be affixed to a solid surface to form a customized array.

Kits may also comprise a sample preparation system. A sample preparation system comprises, generally, any materials or substances that are useful in preparing the urine sample to be contacted with the detection reagents. For example, a sample preparation system may comprise materials for separating urine sediments from the fluids, such as centrifuge tube, a microcentrifuge, or a filter (optionally fitted to a tube designed to permit a pressure gradient to be established across the filter). One example of a filter that can be used is a filter within a syringe, such as those available from Zymo Research (see website at zymoresearch.com/columns-plastics/column-filter-assemblies/zrc-gf-filter; e.g., ZRC-GF Filter™). Other components that can be included in the kit include buffers, precipitating agents for precipitating either wanted or unwanted materials, chelators, cell lysis reagents, RNase inhibitors etc.

Collection, presentation and preparation systems can accomplished in various ways. For example, a filter can be used to separate urine sediments from the fluids, and the filter may be coated with antibodies suitable for specifically detecting the desired proteins. One of skill in the art would, in view of this specification, readily understand many combinations of components that a kit of the invention may comprise.

Definitions

An "anti-rejection agent" is any substance administered to a subject for the purpose of preventing or ameliorating a rejection state. Anti-rejection agents include, but are not limited to, azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD 154, anti-CD3 antibody, thymoglobin, OKT3, corticosteroid, or a combination thereof. "Baseline therapeutic regimen" is understood to include those anti-rejection agents being administered at a baseline time, subsequent to the transplant. The baseline therapeutic regimen may be modified by the temporary or long-term addition of other anti-rejection agents, or by a temporary or long-term increase or decrease in the dose of one, or all, of the baseline anti-rejection agents.

The term "biopsy" refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. Biopsies also include a fine needle aspiration biopsy, a minicore needle biopsy, and/or a conventional percutaneous core needle biopsy.

A "sample" includes fluid samples obtained from a subject. A sample contains cells, proteins, nucleic acids or other cellular matter. A sample may also be the liquid phase of a body fluid from which sedimentary materials have been substantially removed. Exemplary samples include, but are not limited to, blood samples containing peripheral blood mononuclear cells (PBMCs), urine samples containing urinary cells, urine "supernatant" that is substantially free of cells, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft. A sample may also be obtained from essentially any body fluid including: blood (including peripheral blood), lymphatic fluid, sweat, peritoneal fluid, pleural fluid, bronchoalveolar lavage fluid, pericardial fluid, gastrointestinal juice, bile, urine, feces, tissue fluid or swelling fluid, joint fluid, cerebrospinal fluid, or any other named or unnamed fluid gathered from the anatomic area in proximity to the allograft or gathered from a fluid conduit in fluid communication with the allograft. A "post-transplantation sample" refers to a sample obtained from a subject after the transplantation has been performed.

"Baseline level of gene expression level" includes the particular gene expression level of a healthy subject or a subject with a well-functioning transplant. The baseline level of gene expression includes the gene expression level of a subject without acute rejection. The baseline level of gene expression can be a number on paper or the baseline level of gene expression from a control sample of a healthy subject or a subject with a well-functioning transplant.

The term "determining" is used herein to mean testing, assaying, and/or physically manipulating a sample to ascertain what the sample contains. In some cases, "determining" can also include quantifying a component of a sample.

The term "diagnosis" is used herein to refer to the identification or classification of a molecular or pathological state, disease or condition. For example, "diagnosis" may refer to identification of a particular type of acute rejection, e.g., acute cellular rejection.

The term "aiding diagnosis" is used herein to refer to methods that assist in making a clinical determination regarding the presence, degree or other nature, of a particular type of symptom or condition of acute rejection.

The term "prediction" or "predicting" is used herein to refer to the likelihood that a patient will develop acute rejection. Thus, prediction also includes the time period without acute rejection.

A "probe or primer" as used herein refers to a group of nucleic acids that may be used to detect one or more genes (e.g., perforin, granzyme B, IP-10, CD3-epsilong, 18S rRNA, FoxP3, CXCR3, CD103, TGF-β, PI-9, or TGF-βI). Detection may be, for example, through amplification as in PCR, QPCR, RT-PCR, or primer extension. Detection can also be through hybridization, or through selective destruction and protection, as in assays based on the selective enzymatic degradation of single or double stranded nucleic acids, or by detecting RNA affixed to a solid surface (e.g., a blot). Probes and/or primers may be labeled with one or more fluorescent labels, radioactive labels, fluorescent quenchers, enzymatic labels, or other detectable moieties.

Probes may be any size so long as the probe is sufficiently large to selectively detect the desired nucleic acid or to serve as a primer for amplification.

Primers can be polynucleotides or oligonucleotides capable of being extended in a primer extension reaction at their 3' end. In order for an oligonucleotide to serve as a primer, it typically needs only be sufficiently complementary in sequence to be capable of forming a double-stranded structure with the template, or target, under the conditions employed. Establishing such conditions typically involves selection of solvent and salt concentration, incubation temperatures, incubation times, assay reagents and stabilization factors known to those in the art. The term primer or primer oligonucleotide refers to an oligonucleotide as defined herein, which is capable of acting as a point of initiation of synthesis when employed under conditions in which synthesis of a primer extension product that is complementary to a nucleic acid strand is induced, as, for example, in a DNA replication reaction such as a PCR reaction. Like non-primer oligonucleotides, primer oligonucleotides may be labeled according to any technique known in the art, such as with radioactive atoms, fluorescent labels, enzymatic labels, proteins, haptens, antibodies, sequence tags, mass label or the like. Such labels may be employed by associating them, for example, with the 5' terminus of a primer by a plurality of techniques known in the art. Such labels may also act as capture moieties. A probe or primer may be in solution, as would be typical for multiplex PCR, or a probe or primer may be adhered to a solid surface, as in an array or microarray. It is well known that compounds such as PNAs may be used instead of nucleic acids to hybridize to genes. In addition, probes may contain rare or unnatural nucleic acids such as inosine.

As used herein, the term polynucleotide or nucleic acid includes nucleotide polymers of any number. The term polynucleotide includes a molecule comprising any number of nucleotides, preferably, less than about 200 nucleotides. More preferably, polynucleotides are between 5 and 100 nucleotides in length. Most preferably, polynucleotides are 15 to 100 nucleotides in length. The exact length of a particular polynucleotide, however, will depend on many factors, which in turn depend on its ultimate function or use. Some factors affecting the length of a polynucleotide are, for example, the sequence of the polynucleotide, the assay conditions in terms of such variables as salt concentrations and temperatures used during the assay, and whether or not the polynucleotide is modified at the 5' terminus to include additional bases for the purposes of modifying the mass:charge ratio of the polynucleotide, or providing a tag capture sequence which may be used to geographically separate a polynucleotide to a specific hybridization location on a DNA chip, for example.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "recipient" (or "host"). An organ, or graft, transplanted between two genetically different individuals of the same species is called an "allograft." A graft transplanted between individuals of different species is called a "xenograft."

As used herein, "transplant rejection" refers to a functional and structural deterioration of the organ due to an active immune response expressed by the recipient, and independent of non-immunologic causes of organ dysfunction. Acute transplant rejection can result from the activation of recipient's T cells and/or B cells; the rejection primarily due to T cells is classified as T cell mediated acute rejection or acute cellular rejection (ACR) and the rejection in which B cells are primarily responsible is classified as antibody mediated acute rejection (AMR). In some embodiments, the methods and compositions provided can detect and/or predict acute cellular rejection.

As used herein, "subject" means a mammal. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; or the like. The term "subject" does not denote a particular age or sex. Preferably the subject is a human patient. In some embodiments, the subject is a human who has received an organ transplant.

The term "up-regulation," "up-regulated," "increased expression," and "higher expression" are used interchangeably herein and refer to the increase or elevation in the amount of a target mRNA or a target protein. In some embodiments, up-regulation," "up-regulated," "increased expression," and "higher expression" includes increases above a baseline (e.g., a control, or reference) level of 10%, 15%, 20%, 25%, 30%, 35%, 40%, 45%, 50%, 55%, 60%, 65%, 70%, 75%, 80%, 85%, 90%, 95%, 100% or higher.

The term "hybridization" includes a reaction in which one or more nucleic acids or polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, primer extension reaction, or the enzymatic cleavage of a polynucleotide by a ribozyme.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide if hybridization can occur between one of the strands of the first polynucleotide and the second polynucleotide. "Complementarity" or "homology" is quantifiable in terms of the proportion of bases in opposing strands that are expected to hydrogen bond with each other, according to generally accepted base-pairing rules.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al. (1989); Nucleic Acid Hybridization, A Practical Approach, IRL Press, Washington D.C. 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed. In general, the stringency of hybridization is determined by the wash step. Hence, a wash step involving 0.1×SSPE, 1.0% SDS at a temperature of at least 42° C. can yield a high stringency hybridization product. In some instances the high stringency hybridization conditions include a wash in 1×SSPE, 1.0% SDS at a temperature of at least 50° C., or at about 65° C.

"Medium stringency conditions" when used in reference to nucleic acid hybridization include conditions equivalent to binding or hybridization at 42 □° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed. Hence, a wash step involving 1.0×SSPE, 1.0% SDS at a temperature of 42° C. can yield a medium stringency hybridization product.

"Low stringency conditions" include conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed. Hence, a wash step involving 5×SSPE, 1.0% SDS at a temperature of 42° C. can yield low stringency hybridization product.

A "gene product" includes a peptide, polypeptide, or structural RNA generated when a gene is transcribed and/or translated. While an mRNA encoding a peptide or polypeptide can be translated to generate the peptide or polypeptide, a structural RNA (e.g., an rRNA) is not translated. In some embodiments, the target gene expresses perforin, granzyme B, IP-10, CD3-epsilon, 18S rRNA, FoxP3, CXCR3, CD103, TGF-β, PI-9, or TGF-β1.

The term "level of gene expression" as used herein refers to quantifying gene expression. In some embodiments, to accurately assess whether increased mRNA or rRNA is significant, it is preferable to "normalize" gene expression to accurately compare levels of expression between samples, i.e., it is a baseline level against which gene expression is compared. Quantification of gene expression can be accomplished by methods known in the art, such as, for example, reverse transcription polymerase chain reaction (RT-PCR), TAQMAN® assays or the like. Gene expression can also be quantified by detecting a protein, peptide or structural RNA gene product directly, in a variety of assay formats known to those of ordinary skill in the art. For example, proteins and peptides can be detected by an assay such as an enzyme linked immunosorbent assay (ELISA), radioimmunoassay (RIA), immunofluorimetry, immunoprecipitation, equilibrium dialysis, immunodiffusion, immunoblotting, mass spectrometry and other techniques. See, e.g., Harlow and Lane, Antibodies: A Laboratory Manual, Cold Spring Harbor Laboratory, 1 88; Weir, D. M., Handbook of Experimental Immunology, 1986, Blackwell Scientific, Boston.

As used herein, the term "biomarker" includes a polynucleotide or polypeptide molecule which is present or increased in quantity or activity in subjects having acute rejection or where the acute rejection is anticipated.

As used herein, the term "panel of biomarkers" includes a group of markers, the quantity or activity of each member of which is correlated with subjects having acute rejection or where the acute rejection is anticipated. In certain embodiments, a panel of markers may include only those markers which are either increased in quantity or activity in those subjects. In some embodiments, the panel of markers include one, two, three, four, five, six, seven, eight, or nine or more of perforin, granzyme B, IP-10, 18S rRNA, CD3- epsilon, FoxP3, CXCR3, CD103, PI-9, TGF-β, or TGF-β1. For example, the panel can include 18S rRNA, CD3-epsilon, and IP-10.

The present description is further illustrated by the following examples, which should not be construed as limiting in any way.

Example 1: Clinical Trials in Organ Transplantation

Figure 1A:
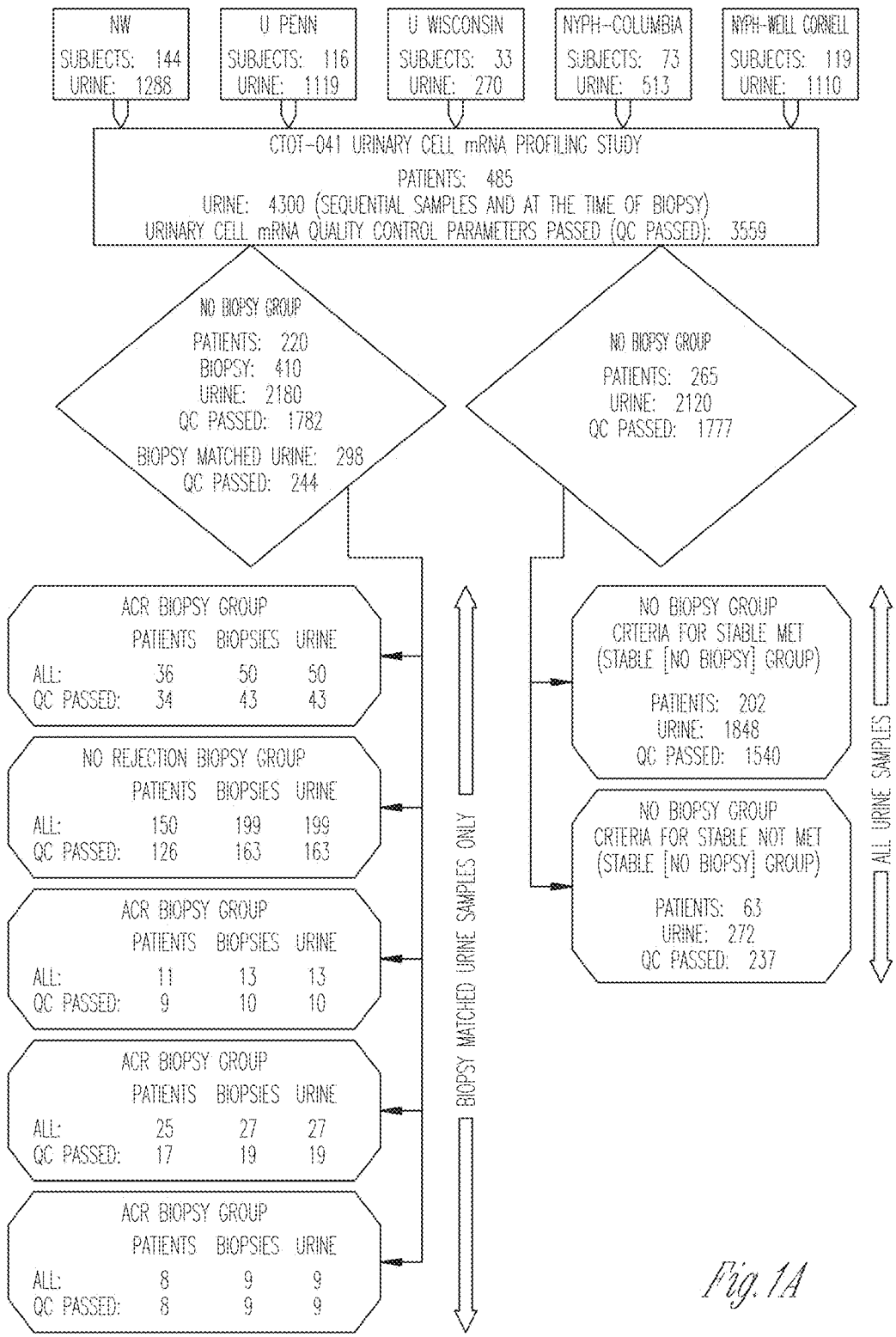
FIG. 1A-1B are flow charts showing information about clinical trials.
Figure 1B:
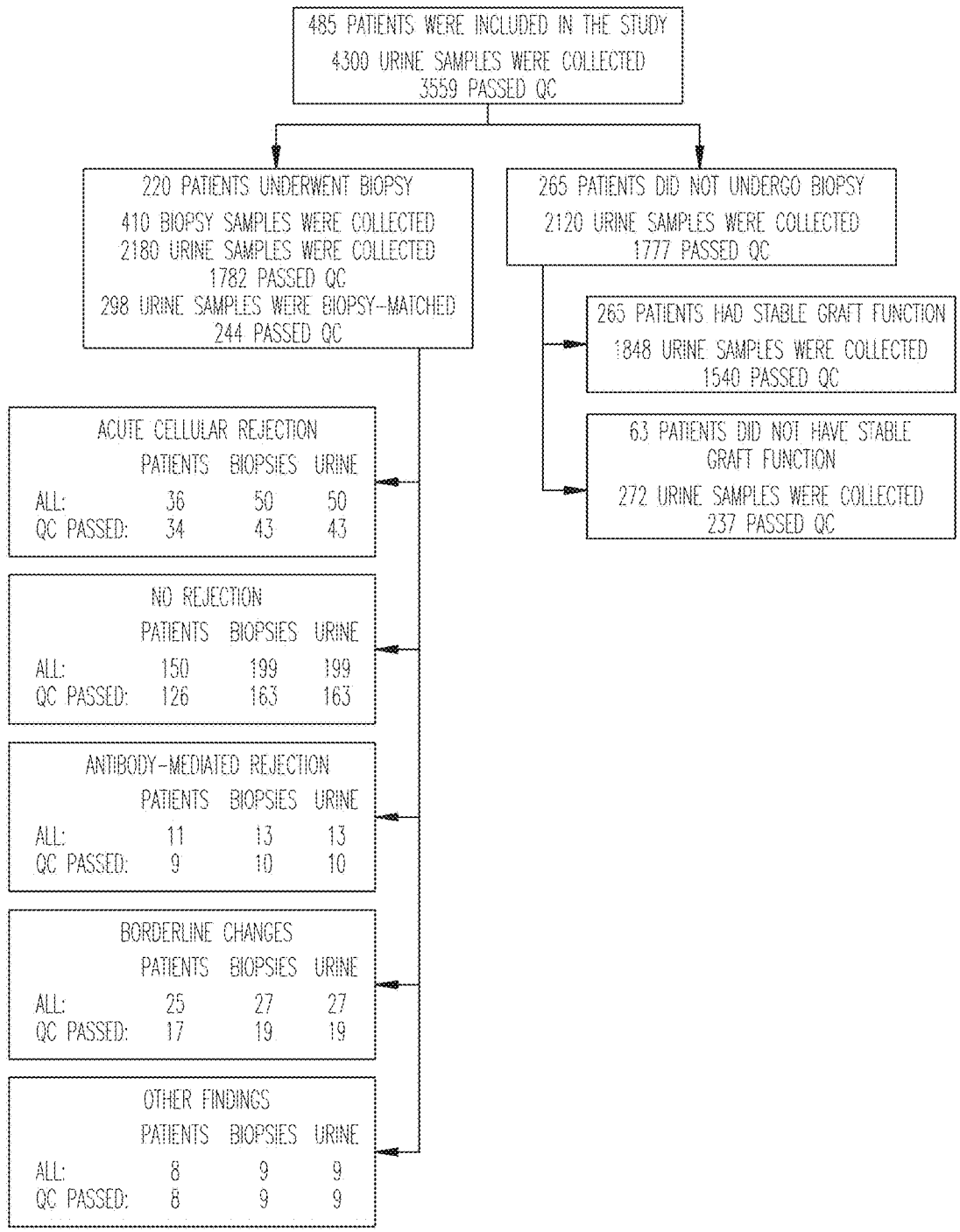

To overview the CTOT-04 prospective observational study, 497 patients with ESRD were enrolled at 5 clinical sites and 492 received a kidney transplant. Urine specimens (4300 separate samples) were collected for urinary cell mRNA profiling from 485 patients (FIG. 1). The institutional review board at each site approved the study and each patient gave written informed consent. A NIH-sponsored Statistical and Clinical Coordinating Center (SACCC) was responsible for data management and data analysis.

The CTOT-04 multicenter, prospective observational study was initiated in April 2006 with a target enrollment of 495 kidney transplant recipients from 5 clinical sites. At its conclusion in January 2008, 497 patients with end stage renal disease (ESRD) had been enrolled. Five of the 497 patients enrolled in CTOT-04 did not receive a kidney graft, and 7 of the 492 transplanted patients did not provide urine specimens. The demographic and clinical characteristics of the 485 kidney transplant recipients—urinary cell mRNA profiling study cohort—and their organ donors are summarized in Table 1. Among the 485 patients, 220 patients underwent at least one renal allograft biopsy and the remaining 265 patients did not undergo a biopsy. Table 1 also shows the characteristics of the recipients who underwent a kidney allograft biopsy and those who did not undergo a biopsy.

TABLE 1

Characteristics of CTOT-04 Kidney Transplant Recipients and their Organ Donors.

|  | Total* (N = 485) | Patients with Biopsies (N = 220) | Patients without Biopsies (N = 265) |
|---|---|---|---|
| Recipient Characteristics | | | |
| Age, years | | | |
| Mean (SD) | 48.3 (13.17) | 47.7 (12.46) | 48.9 (13.73) |
| Median | 49 | 47 | 50 |
| Min†, Max | 2, 77 | 3.5, 76 | 2, 77 |
| Gender, N (%) | | | |
| Female | 197 (40.6) | 75 (34.1) | 122 (46.0) |
| Male | 288 (59.4) | 145 (65.9) | 143 (54.0) |
| Ethnicity, N (%) | | | |
| Hispanic or Latino | 72 (14.8) | 33 (15.0) | 39 (14.7) |
| Not Hispanic or Latino | 386 (79.6) | 174 (79.1) | 212 (80.0) |
| Unknown or Not Reported | 27 (5.6) | 13 (5.9) | 14 (5.3) |
| Race, N (%) | | | |
| Black or African American | 138 (28.5) | 75 (34.1) | 63 (23.8) |
| White | 277 (57.1) | 122 (55.5) | 155 (58.5) |
| Asian | 23 (4.7) | 12 (5.5) | 11 (4.2) |
| American Indian or Alaska Native | 2 (0.4) | 0 | 2 (0.8) |
| Other | 33 (6.8) | 8 (3.6) | 25 (9.4) |
| More Than One Race | 3 (0.6) | 0 | 3 (1.1) |
| Unknown or Not Reported | 9 (1.9) | 3 (1.4) | 6 (2.3) |
| Induction Therapy | | | |
| IL-2 Receptor Antibody, number of patients | 54 | 28 | 26 |
| Total number of biopsies |  | 72 |  |
| (For-cause/Surveillance) |  | (65/7) |  |
| CAMPATH-1H, number of patients | 127 | 86 | 41 |
| Total number of biopsies |  | 156 |  |
| (For-cause/Surveillance) |  | (77/79) |  |
| Thymoglobulin, number of patients | 247 | 79 | 168 |
| Total number of biopsies |  | 136 |  |
| (For-cause/Surveillance) |  | (136/0) |  |
| More than one induction therapy, number of patients | 21 | 12 | 9 |
| Total number of biopsies |  | 21 |  |
| (For-cause/Surveillance) |  | (21/0) |  |
| No Induction Therapy, number of patients | 4 | 3 | 1 |
| Total number of biopsies |  | 8 |  |
| (For-cause/Surveillance) |  | (8/0) |  |
| Missing Information, number of patients | 32 | 12 | 20 |
| Total number of biopsies |  | 17 |  |
| (For-cause/Surveillance) |  | (14/3) |  |
| BMI | | | |
| Mean (SD) | 28.0 (6.15) | 28.9 (6.47) | 27.3 (5.74) |
| Median | 27 | 28 | 26 |
| Min, Max | 3, 56 | 16, 56 | 3, 43 |
| <18.5 | 11 (2.3) | 4 (1.8) | 7 (2.6) |

TABLE 1-continued

Characteristics of CTOT-04 Kidney Transplant Recipients and their Organ Donors.

|  | Total* (N = 485) | Patients with Biopsies (N = 220) | Patients without Biopsies (N = 265) |
| --- | --- | --- | --- |
| 18.5-24.9 | 133 (27.4) | 60 (27.3) | 73 (27.5) |
| 25.0-29.9 | 142 (29.3) | 67 (30.5) | 75 (28.3) |
| ≥30.0 | 136 (28.0) | 73 (33.2) | 63 (23.8) |
| Missing | 63 (13.0) | 16 (7.3) | 47 (17.7) |
| Donor Characteristics | | | |
| Age | | | |
| Mean (SD) | 40.4 (14.73) | 41.0 (14.73) | 39.9 (14.74) |
| Median | 41 | 42 | 41 |
| Min†, Max | 5, 76 | 5, 75 | 12, 76 |
| Missing | 4 | 1 | 3 |
| Gender, N (%) | | | |
| Female | 228 (47.0) | 116 (52.7) | 112 (42.3) |
| Male | 257 (53.0) | 104 (47.3) | 153 (57.7) |
| Ethnicity, N (%) | | | |
| Hispanic or Latino | 79 (16.3) | 33 (15.0) | 46 (17.4) |
| Not Hispanic or Latino | 350 (72.2) | 164 (74.5) | 186 (70.2) |
| Unknown or Not Reported | 56 (11.5) | 23 (10.5) | 33 (12.5) |
| Race, N (%) | | | |
| Black or African American | 76 (15.7) | 49 (22.3) | 27 (10.2) |
| White | 353 (72.8) | 152 (69.1) | 201 (75.8) |
| Asian | 14 (2.9) | 7 (3.2) | 7 (2.6) |
| American Indian or Alaska Native | 2 (0.4) | 1 (0.5) | 1 (0.4) |
| Other | 3 (0.6) | 0 | 3 (1.1) |
| Unknown or Not Reported | 37 (7.6) | 11 (5.0) | 26 (9.8) |
| Source of Donor, N (%) | | | |
| Deceased | 215 (44.3) | 101 (45.9) | 114 (43.0) |
| Living/related | 159 (32.8) | 65 (29.5) | 94 (35.5) |
| Living/unrelated | 111 (22.9) | 54 (24.5) | 57 (21.5) |
| Cause of Death, N (%) | | | |
| Anoxia, N (%) | 36 (16.7) | 16 (15.8) | 20 (17.5) |
| Cerebrovascular Accident/Injury/Stroke, N (%) | 65 (30.2) | 41 (40.6) | 24 (21.1) |
| Head Injury/Trauma, N (%) | 47 (21.9) | 18 (17.8) | 29 (25.4) |
| Intracranial Bleed, N (%) | 14 (6.5) | 8 (7.9) | 6 (5.3) |
| Motor Vehicle Accident, N (%) | 4 (1.9) | 1 (1.0) | 3 (2.6) |
| Other, N (%) | 17 (7.9) | 10 (9.9) | 7 (6.1) |
| Unknown, N (%) | 27 (12.6) | 5 (5.0) | 22 (19.3) |
| Missing, N (%) | 3 (1.4) | 2 (2.0) | 1 (0.9) |

*Out of the 497 subjects enrolled, 492 received a kidney transplant; baseline characteristics are reported for the 485 transplant subjects who also provided urine specimens; 220 had at least one biopsy and 265 had no recorded biopsy.
†Minimum age is shown in months and all other ages in years.

The inclusion criteria were: (1) male and female recipients of all races, 0-80 years of age; (2) patients undergoing primary or re-do living or deceased donor and kidney transplantation; and (3) ability to provide informed consent. The exclusion criteria were: (1) need for combined organ transplantation; (2) recipients of previous non-renal solid organ and/or islet cell transplantation; (3) infection with HCV or HIV; and (4) inability or unwillingness to provide informed consent.

The CTOT-04 trial was designed to be an observational study with each of the 5 participating sites being able to use site-specific immunosuppression and infection protocols. The rationale for the study design included the consideration that the urine mRNA profiling results should be generalizable to the kidney transplant population and not be restricted by the clinical therapeutic regimens.

The original target sample size of 450 was based on at least 400 subjects being available for subsample analyses. With 400 subjects and a 10% acute rejection rate (40 subjects with acute rejection and 360 subjects without acute rejection), the study would have 96% power to detect a standardized odds ratio of 2.0 using an alpha=0.05, two-tailed significance in a logistic regression.

Characteristics of the 64 patients in the external-validation data set are provided in Table 2.

TABLE 2

Characteristics of CTOT-01 Kidney Transplant Recipients Used as the External-Validation Set and their Organ Donors

|  | Total (N = 64) |
| --- | --- |
| Recipient Characteristics | |
| Age, years | |
| Mean (SD) | 44.3 (15.41) |
| Median | 47 |
| Min†, Max | 9, 70 |

TABLE 2-continued

Characteristics of CTOT-01 Kidney Transplant Recipients
Used as the External-Validation Set and their Organ Donors

| | Total (N = 64) |
|---|---|
| Gender, N (%) | |
| Female | 32 (50) |
| Male | 32 (50) |
| Ethnicity, N (%) | |
| Hispanic or Latino | 3 (4.7) |
| Not Hispanic or Latino | 51 (79.7) |
| Unknown or Not Reported | 10 (15.6) |
| Race, N (%) | |
| Black or African American | 24 (37.5) |
| White | 35 (54.7) |
| Asian | 2 (3.1) |
| American Indian or Alaska Native | 1 (1.6) |
| Other | 1 (1.6) |
| More Than One Race | 1 (1.6) |
| Induction Therapy | |
| IL-2 Receptor Antibody | 21 (32.8) |
| Anti-thymocyte globulin | 33 (51.6) |
| More than one induction therapy | 4 (6.3) |
| No Induction Therapy | 5 (7.8) |
| Missing Information | 1 (1.6) |
| BMI | |
| Mean (SD) | 27.3 (5.75) |
| Median | 27 |
| Min, Max | 16, 48 |
| <18.5 | 1 (1.6) |
| 18.5-24.9 | 22 (34.4) |
| 25.0-29.9 | 16 (25.0) |
| ≥30.0 | 21 (32.8) |
| Missing | 4 (6.3) |
| Donor Characteristics | |
| Age | |
| Mean (SD) | 42.9 (13.09) |
| Median | 43 |
| Min†, Max | 18, 71 |
| Gender, N (%) | |
| Female | 37 (57.8) |
| Male | 27 (42.2) |
| Ethnicity, N (%) | |
| Hispanic or Latino | 2 (3.1) |
| Not Hispanic or Latino | 41 (64.1) |
| Unknown or Not Reported | 21 (32.8) |
| Race, N (%) | |
| Black or African American | 14 (21.9) |
| White | 43 (67.2) |
| Asian | 1 (1.6) |
| American Indian or Alaska Native | 2 (0.4) |
| Other | 2 (3.1) |
| Unknown or Not Reported | 2 (3.1) |
| Source of Donor, N (%) | |
| Deceased | 25 (39.1) |
| Living | 39 (60.9) |
| Cause of Death, N (%) | |
| Anoxia, N (%) | 2 (8.0) |
| Cerebrovascular Accident/Injury/Stroke, N (%) | 8 (32.0) |
| Head Injury/Trauma, N (%) | 5 (20.0) |
| Intracranial Bleed, N (%) | 1 (4.0) |
| Other, N (%) | 5 (20.0) |
| Unknown, N (%) | 4 (16.0) |

Urine samples used as the external validation set were independently collected, blinded urine samples from the Clinical Trials in Organ Transplantation-01 (CTOT-01) study, a NIH-sponsored study initiated at the same time as the CTOT-04 study. A total of 280 subjects received a kidney transplant under the CTOT-01 protocol. Post-transplant follow-up yielded 180 surveillance biopsies at Month 6, 108 for-cause biopsies during the first 6 months post-transplant, and 52 for-cause biopsies after the first 6 months. Out of these 340 biopsies, all 24 acute cellular rejection (ACR) biopsies and a random selection of 47 non-acute cellular rejection (No Rejection) biopsies in 64 subjects were used to construct the external validation set by the NIH-sponsored SACCC, independent of the CTOT-04 investigators. Power calculations showed that if the population sensitivity and specificity of the diagnostic signature were both 75%, a sample size of 22 acute cellular rejections and 44 no rejection biopsies would provide 98% power to detect a significant 2×2 association between the diagnostic signature (dichotomized at the pre-specified cutoff point) and biopsy status using a two-tailed, alpha=0.05 test.

Example 2: Collection of Urine Samples and RNA Measurements

This Example describes some of the materials and methods that have been used in the development of the invention.
Collection of Urine Samples and Preparation of Urine Cell Pellets Urine samples (about 50 ml) from the enrolled kidney transplant recipients were collected longitudinally with the pre-specified schedule for collection being post-transplant days 3, 7, 15 and 30 and months 2, 3, 4, 5, 6, 9 and 12, and at the time of any renal allograft biopsy and prior to treatment and 2-weeks after biopsy. All centers followed an identical protocol with respect to urine sample collection and urine cell pellets were prepared at the clinical sites with the use of a standard protocol for urine cell sedimentation, stored at −80° C. and shipped in batches, to the Gene Expression Monitoring (GEM) Core at Weill Cornell Medical College, New York, N.Y. (WCMC).

Four thousand three hundred urine cell pellets from 4300 urine specimens collected from 485-kidney transplant recipients were prepared at the clinical sites and shipped to the GEM Core for the isolation of RNA from the urine cell pellet, measurement of mRNAs and the reporting of assay results to the NIH-sponsored Statistical and Clinical Coordinating Center (SACCC).
Isolation of Total RNA from Urinary Cell Pellet Total RNA was isolated from urinary cell pellets using the PureLink Micro-to-Midi total RNA purification system (Cat. 12183-018, Invitrogen). In brief, the urinary cell pellet was lysed by adding one volume of lysis buffer and vortexing. Following the addition of an equal volume of 100% ethanol, the sample was transferred to an RNA spin cartridge. The cartridge was then washed 3 to 4 times with the wash buffers provided in the kit and the total RNA was eluted from the cartridge with 30 μl of RNase-free water.

The quantity (absorbance at 260 nm) and purity (ratio of the absorbance at 260 and 280 nm) of the RNA isolated from the urine cell pellet were measured using the NanoDrop® ND-1000 UV-Vis spectrophotometer (Thermo Scientific). A RNA sample was classified as quality control passed if the 18S rRNA copy number was greater than or equal to $5 \times 10^7$ and its TGF-β1 mRNA copy number was greater than or equal to 100 copies in one microgram of RNA; 3559 (83%) urine samples passed both criteria. The median (25th percentile and $75^{th}$ percentile) of the quantity of total RNA isolated from 4299 samples, those that passed quality control parameters and those that failed are shown in Table 3. This table also shows the median (25th percentile and 75th percentile) of the purity of total RNA isolated for all 4300 samples and separately for those that passed versus failed quality control.

TABLE 3

Quantity and Purity of RNA Isolated from Urine Cell Pellets.*

RNA Quantity

| Total RNA Quantity (ng) | Total Sample (N = 4299) | QC Passed† (N = 3559) | QC Failed (N = 740) | P Value‡ QC passed vs. QC failed |
|---|---|---|---|---|
| Median | 504.00 | 559.90 | 259.50 | <0.0001 |
| 25% Percentile | 283.30 | 332.90 | 173.10 | |
| 75% Percentile | 894.00 | 973.60 | 477.30 | |

RNA Purity

| A260/280 Ratio | Total sample (n = 4300) | QC Passed† (n = 3559) | QC Failed (n = 741) | P Value‡ QC passed vs. QC failed |
|---|---|---|---|---|
| Median | 1.79 | 1.80 | 1.70 | <0.0001 |
| 25% Percentile | 1.64 | 1.67 | 1.51 | |
| 75% Percentile | 1.89 | 1.89 | 1.85 | |

*Total RNA was isolated from the urine cell pellets with the use of a commercial kit (PureLink Micro-to-Midi total RNA purification system, Invitrogen) and the quantity (absorbance at 260 nm) and purity (ratio of the absorbance at 260 and 280 nm) of the RNA isolated from the urine cell pellet was measured using the NanoDrop ® ND-1000 UV-Vis spectrophotometer (Thermo Scientific).
†A RNA sample was classified as quality control passed if the 18S rRNA copy number was greater than or equal to 5.00E+07 and TGF-β1 mRNA copy number was greater than or equal to 100 copies in one microgram of RNA.
‡Two-tailed P value is based on the Mann-Whitney test.

The GEM Core isolated RNA from the pellet, assessed RNA quantity and purity (Table 3) and quantified absolute levels of the mRNAs pre-specified in the CTOT-04 protocol: CD3ε, perforin, granzyme B, PI-9, CD103, IP-10, CXCR3, TGF-β1, and 18S rRNA, using Core designed oligonucleotide primers and TaqMan probes (Table 4) in the preamplification enhanced quantitative real-time PCR (QPCR) assay and reported the assay results to the SACCC. The Core was blind to all clinical information, including kidney allograft biopsy results, prior to transfer of the mRNA dataset to the SACCC.

Reverse Transcription to Complementary DNA

The total RNA was reverse transcribed (RT) to cDNA using the TaqMan reverse transcription kit (Cat. N808-0234, Applied Biosystems) on the same day the total RNA was isolated. The RT was at the concentration of 1.0 μg of total RNA in 100 μl volume and the reaction contained the final concentration of 1×TaqMan RT buffer, 5.5 mM of Magnesium Chloride, 500 μM each of 4 dNTPs, 2.5 μM of Random Hexamer, 0.4 Unit/μl of RNase inhibitor, and 1.25 Unit/μl of MultiScribe Reverse Transcriptase. The sample was incubated at 25° C. for 10 min, 48° C. for 30 min, and 95° C. for 5 min.

Design of Gene Specific Oligonucleotide Primers and Taqman Probes

The GEM Core designed gene specific oligonucleotide primers and TaqMan fluorogenic probes (hydrolysis probes) for the measurement of levels of mRNAs pre-specified in the CTOT-04 Protocol: CD3ε, perforin, granzyme B, IP-10, CXCR3, CD103, TGF-β1, PI-9 and 18S rRNA. The sequence and location of the gene specific oligonucleotide primer pairs and TaqMan probes are provided in Table 4.

TABLE 4

Oligonucleotide Primers and TaqMan Probes used to Measure Levels of mRNA.*

| Type of mRNA | GenBank Accession Number | Sequence | Location |
|---|---|---|---|
| CD3-epsilon | NM_000733 | Sense: 5'-AAGAAATGGGTGGTATTACACAGACA-3' SEQ ID NO: 4 | 131-156 |
| | | Antisense: 5'-TGCCATAGTATTTCAGATCCAGGAT-3' SEQ ID NO: 5 | 233-209 |
| | | Probe: 5'-FAM-CCATCTCTGGAACCACAGTAATATTGACATGCC-TAMRA-3' SEQ ID NO: 6 | 170-202 |
| Perforin | M28393 | Sense: 5'-GGACCAGTACAGCTTCAGCACTG-3' SEQ ID NO: 7 | 492-514 |
| | | Antisense: 5'-GCCCTCTTGAAGTCAGGGTG-3' SEQ ID NO: 8 | 587-568 |
| | | Probe: 5'-FAM-TGCCGCTTCTACAGTTTCCATGTGGTACAC-TAMRA-3' SEQ ID NO: 9 | 526-555 |
| Granzyme B | J04071 | Sense: 5'-GCGAATCTGACTTACGCCATTATT-3' SEQ ID NO: 10 | 534-557 |
| | | Antisense: 5'-CAAGAGGGCCTCCAGAGTCC-3' SEQ ID NO: 11 | 638-619 |
| | | Probe: 5'-FAM-CCCACGCACAACTCAATGGTACTGTCG-TAMRA-3' SEQ ID NO: 12 | 559-585 |

TABLE 4 -continued

Oligonucleotide Primers and TaqMan Probes used to Measure Levels of mRNA.*

| Type of mRNA | GenBank Accession Number | Sequence | Location |
|---|---|---|---|
| IP-10 | NM_001565.1 | Sense: 5'-TGTCCACGTGTTGAGATCATTG-3' SEQ ID NO: 13 | 235-256 |
| | | Antisense: 5'-GGCCTTCGATTCTGGATTCA-3' SEQ ID NO: 14 | 309-290 |
| | | Probe: 5'-FAM TACAATGAAAAAGAAGGGTGAGAA-MGB-3' SEQ ID NO: 15 | 258-281 |
| CXCR3 | NM_001504 | Sense: 5'-ACCCAGCAGCCAGAGCAC-3' SEQ ID NO: 16 | 41-58 |
| | | Antisense: 5'-CAACCTCGGCGTCATTTAGC-3' SEQ ID NO: 17 | 117-98 |
| | | Probe: 5'-FAM-CTTGGTGGTCACTCACCTCAAGGACCAT-TAMRA-3' SEQ ID NO: 18 | 69-96 |
| CD103 | XM_008508 | Sense: 5'-CGTGCTCAGCTCCCTTCTG-3' SEQ ID NO: 19 | 211-229 |
| | | Antisense: 5'-CCTGGTGTCCTCTTGGTTCTG-3' SEQ ID NO: 20 | 297-277 |
| | | Probe: 5'-FAM-ACCAAGACCCCAGCACCAACCATACCT-TAMRA-3' SEQ ID NO: 21 | 231-257 |
| TGF-β1 | NM_000660 | Sense: 5'-GCGTGCTAATGGTGGAAACC-3' SEQ ID NO: 22 | 1170-1189 |
| | | Antisense: 5'-CGGAGCTCTGATGTGTTGAAGA-3' SEQ ID NO: 23 | 1263-1242 |
| | | Probe: 5'-FAM-ACAACGAAATCTATGACAAGTTCAAGCAGAGTACACA-TAMRA-3' SEQ ID NO: 24 | 1191-1227 |
| PI-9 | NM_004155 | Sense: 5'-TCAACACCTGGGTCTCAAAAAA-3' SEQ ID NO: 25 | 508-529 |
| | | Antisense: 5'-CAGCCTGGTTTCTGCATCAA-3' SEQ ID NO: 26 | 590-571 |
| | | Probe: 5'-FAM-AGCTACCCGGCAACAACTCTTCAATTTTACCT-TAMRA-3' SEQ ID NO: 27 | 536-567 |
| 18S rRNA | K03432 | Sense: 5'-GCCCGAAGCGTTTACTTTGA-3' SEQ ID NO: 28 | 929-948 |
| | | Antisense: 5'-TCCATTATTCCTAGCTGCGGTATC-3' SEQ ID NO: 29 | 1009-986 |
| | | Probe: 5'-FAM-AAAGCAGGCCCGAGCCGCC-TAMRA-3' SEQ ID NO: 30 | 965-983 |

* The sequences and the locations of the oligonucleotide primers and probes the inventors designed and validated for the measurement of mRNA levels and 18S ribosomal RNA (rRNA) in the urine are shown. The fluorogenic TaqMan probes were labeled with 6-carboxy-fluorscein (FAM) at the 5' end and with 6-carboxy-tetramethylrodamine (TAMRA) or minor groove binder (MGB) at the 3' end. FAM functioned as the reported dye and TAMRA or MGB as the quencher.

mRNA Measurement via Preamplification Enhanced Quantitative Real Time PCR

PCR analysis was performed by a two-step process, a preamplification step (Muthukumar et al., N Engl J Med 353:2342-51 (2005)) followed by measurement of mRNA with an ABI Prism 7500/7900HT Fast detection system. A preamplification protocol was developed that allows quantification of multiple mRNAs from small amounts of cDNA. The preamplification reaction for each sample was set up in a 0.2 ml PCR tube with a final reaction volume of 10.0 µl containing 3.0 µl cDNA (from reverse transcription of 1 µg total RNA in 100 µl buffer), 1.0 µl 10× buffer, 0.6 µl MgCl$_2$ (25 mM), 0.4 µl 4×dNTP (10 mM each), 0.4 µl Ampli-Taq gold (5 U/µl), 0.15 µl primer mix per gene (50 µM sense and 50 µM antisense primer) and 1.0 µl water to a final volume of 10 µl. Following vortexing, the PCR was set up in a Veriti thermal cycler (Applied Biosystems) and the PCR reaction profile consisted of an initial hold at 95° C. for 10 min, 10 cycles of denaturing at 95° C. for 15 seconds and primer annealing and extension at 60° C. for 1 min. At the end of 10 cycles of amplification, 140 µl of TE buffer was added to the PCR reaction and 2.5 µl of diluted PCR amplicons were then used for quantification of mRNA using the real-time quantitative PCR assay.

Method for Absolute Quantification of mRNAs

Absolute mRNA levels were calculated using a previously described standard curve method developed by the inventors (Muthukumar et al., N Engl J Med 353:2342-51 (2005)). The standard curve was established using PCR generated 73-bp mouse Bak amplicon as the standard. The Bak amplicon was generated in a PCR using a GeneAmp 9600 thermal cycler with a final volume of 100 µl containing 3 µL cDNA and 1.6 µL of 4×dNTP (10 mM each), 10 µL 10× buffer, 1.6 µl AmpliTaq gold DNA polymerase (5 U/µl), 6.0 MgCl$_2$ and 2.0 µl Bak-specific oligonucleotide primer pair (50 µM each) (sense primer: 5' CCCACATCTGGAGCAGAGTCA 3' [192-212, SEQ ID NO:31]; antisense primer: 5' CAGATGCCATTTTTCAGGTCTTG 3' [264-242, SEQ ID NO:32], accession no. Y13231). The PCR product was separated by electrophoresis with a 2% agarose gel and the amplicon size (73 bp) was confirmed using a DNA size standard of pUC mix marker 8 (Crystalgen). The Bak amplicon was isolated and purified from the gel with the QIAquick gel extraction kit (QIAGEN). The absolute quantity of the purified amplicon was measured by A260 and converted to the number of copies using the molecular weight of DNA. The Bak amplicon was diluted to a concentration of $10^7$ copies/µL (stock solution). When a standard curve was to be established for the real-time quantitative PCR assay, the stock solution was diluted over 6 orders of magnitude (1,000,000, 100,000, 10,000, 1,000, 100, and 10 copies per 1 µL) (work solution). Work solution (2.5 µL) was added to duplicate wells and amplified with Bak-specific primer pair and Bak-specific fluorogenic TaqMan probe (5' FAM CAGGTGACAAGTGACGGTGGTCTCCA TAMRA 3' [215-240; SEQ ID NO:33]). The threshold cycles ($C_T$) were then plotted against the log of the initial amount of the Bak amplicon to develop the standard curve.

In this study a single Bak standard curve was applied for quantification of all target genes instead of gene specific standard curves. To ensure the accuracy of quantification of target genes with single Bak standard curve, the amplification efficiency of Bak and all individual target genes were determined. This evaluation demonstrated that the amplification efficiency is ≥90% using the primer-probe set in real-time PCR assays for Bak and for all other target mRNAs (CD3ε, perforin, granzyme B, IP-10, CXCR3, CD103, TGF-β1, PI-9) and 18S rRNA. Thus, there was minimal bias due to different amplification efficiencies of target genes and the Bak amplicon.

The strategy of absolute quantification of the levels of mRNAs instead of relative quantification (Schmittgen & Livak, Nat Protoc 3:1101-8 (2008)) using the comparative $C_T$ method ($2^{-\Delta\Delta C_T}$ Method), facilitated not only absolute quantification of levels of mRNA for CD3ε, perforin, granzyme B, IP-10, CXCR3, CD103, TGF-β1, PI-9 (target genes) but also absolute quantification of levels of reference gene 18S rRNA. Because $\Delta C_T = C_T$ target gene $- C_T$ reference gene, alterations in the abundance of the reference gene could be masked when the comparative $C_T$ method is used and mRNA levels are reported as a relative quantity. The comparative $C_T$ method is also contingent upon inclusion of the $\Delta C_T$ of the calibrator (control) in the calculation and it is not always clear what the appropriate calibrator (control) should be when measuring the in-vivo abundance of mRNAs. These limitations are not applicable to the standard curve method used in this study to measure levels of mRNAs in urinary cells. The method used for the absolute quantification helped identify that 18S rRNA levels are higher in urine samples matched to acute cellular rejection (ACR) biopsies than those matched to No Rejection biopsies or urine samples obtained from the Stable (no biopsy) group (Table 5A-5B) and are in accord with the findings that activated cells express 18S rRNA in higher abundance compared to resting or well differentiated cells. Indeed, with the use of the primers and TaqMan probes used in this study, it was found that phytohaemagglutinin (PHA) activated human peripheral blood mononuclear cells express higher levels of 18S rRNA compared to resting cells: $2.39 \times 10^{10}$ 18S rRNA copies per microgram of RNA in human peripheral blood mononuclear cells activated with the mitogen PHA for 72 hours vs. $9.21 \times 10^9$ 18S rRNA copies per microgram of RNA in human peripheral blood mononuclear cells not stimulated with PHA (quiescent/unactivated cells).

The standard curve copy numbers in the PCR assays ranged from 25 to 2.5 million copies, and for data analysis, mRNA copy numbers less than 25 (including 0) were scored as 12.5 copies per 1 microgram rRNA prior to normalization by 18S rRNA copy number and $\log_{10}$ transformation.

Example 3: Kidney Allograft Biopsy Findings

This Example describes some of the analyses performed on biopsy samples.

Recording of Kidney Allograft Biopsy Findings

Each on-site pathologist classified the biopsies using the Banff schema (Racusen et al., Am J Transplant 3:708-14 (2003)) in existence at the time the CTOT-04 protocol was developed and the biopsy results were recorded prospectively using the SACCC Biopsy Form with fields for reason for biopsy (Suspected rejection, Graft dysfunction, Other), adequacy of the biopsy specimen (Yes/No) and recoding of the biopsy results (for adequate biopsies) using the Banff classification and checking one of the following: Normal; Borderline; Antibody mediated rejection (Grade I-ATN); Antibody mediated rejection (Grade II-Capillary); Antibody mediated rejection (Grade III-Arterial); Mild acute cellular rejection (Grade IA); Mild acute cellular rejection (Grade IB); Moderate acute cellular rejection (Grade IIA); Moderate acute cellular rejection (Grade IIB); Severe acute cellular rejection (Grade III); Mild chronic allograft nephropathy (Grade I); Moderate chronic allograft nephropathy (Grade II); severe chronic allograft nephropathy (Grade III); N/A. The Other Findings in the biopsies were also recorded, checking all that applied, using the following: Acute tubular necrosis; Calcineurin toxicity; Bacterial infection/Pyelonephritis; Cytomegalovirus infection; Polyoma/BK nephropathy; Recurrent disease; Obstruction; Post-transplant lymphoproliferative diseases (PTLD); Glomerulosclerosis; Vascular narrowing; Interstitial fibrosis; Tubular atrophy; Other. The pathology form had an additional field to specify Other Findings.

Kidney Allograft Biopsies and Urine Specimens for mRNA Profiling

There were 424-recorded biopsies of which 410 biopsies from 220 patients were judged adequate for biopsy diagnosis. The reason for performing 321 of these 410 biopsies was listed as suspected rejection/graft dysfunction (designated as for-cause biopsy in this report) in the biopsy form and the reason for the remaining 89 biopsies was listed as Other/protocol (designated as surveillance biopsy in this report). Among the 410 biopsies, 112 (105 for-cause and 7 surveillance biopsies) did not have a matched urine specimen (urine collected minus 3 days to plus 1 day of the biopsy) and the remaining 298 biopsies (216 for-cause and 82 surveillance biopsies) had matched urine specimens. Eighty-eight percent (n=265) of the 298 matched urine specimens were collected on the day of biopsy, 3.0% (n=9) three days, 1.3% (n=4) two days and 3.3% (n=10) one day prior to biopsy and 3.3% (n=10) one day after the biopsy. Among the 298-matched urine specimens, 244 (81%) passed urine QC parameters pre-specified prior to data analysis.

Acute Cellular Rejection (ACR) Biopsy Group

Among the 71 biopsies (63 for-cause and 8 surveillance biopsies) from 51 patients classified as Banff acute cellular rejection (ACR) grade IA or higher, 21 did not have matched urine specimens and 43 of the 50 biopsy matched urine specimens passed PCR assay QC parameters. Among the 43 acute cellular rejection biopsies (38 for-cause and 5 surveillance biopsies) from 34 patients that had matched urine specimens that passed QC, 19 biopsies were graded as mild acute cellular rejection grade IA, 10 as mild acute cellular rejection grade IB, 11 as Moderate acute cellular rejection grade IIA, 2 as Moderate acute cellular rejection grade IIB and 1 as severe acute cellular rejection grade III. Urinary cell mRNA levels in the 43 QC-passed urine specimens matched to the 43 acute cellular rejection biopsies were used to generate the box and whisker plots shown in FIG. 2. The median, $25^{th}$ and $75^{th}$ percentiles of the $\log_{10}$ transformed ratios of mRNA copies per microgram of total RNA to 18S rRNA copies ($\times 10^{-6}$) per microgram of total RNA are reported in Table 5A, and the non-normalized, non-log transformed absolute mRNA copy numbers per microgram of total RNA and 18rRNA copies ($\times 10^{-6}$) per microgram of RNA are reported in Table 5B.

No Rejection Biopsy Group

There were 259 biopsies (190 for-cause and 69 surveillance biopsies) from 173 patients classified as Normal or N/A on the basis of these biopsies not showing histologic features of acute cellular rejection, AMR, Borderline, CAN changes, bacterial infection/pyelonephritis, or BKV/polyoma nephropathy (No Rejection biopsies). Several of the biopsies classified as No Rejection biopsies displayed histological changes such as acute tubular necrosis (ATN) (n=66), tubular atrophy (n=54), interstitial fibrosis (n=49), glomerulosclerosis (n=23), vascular narrowing (n=17), calcineurin toxicity (n=10), and/or recurrent disease (n=2) and several biopsies displayed more than one abnormality such as the presence of both interstitial fibrosis and tubular atrophy. Sixty of the 259 No Rejection biopsies did not have matched urine specimens and 36 of the matched urine specimens failed PCR assay QC parameters, resulting in 163 No Rejection biopsies (107 for-cause and 56 surveillance biopsies) with 163 matched, QC-passed urine specimens from 126 patients. The urinary cell mRNA levels in the 163 QC-passed urine specimens matched to the 163 No Rejection biopsies were used to generate the box and whisker plots shown in FIG. 2. The median, 25th and 75th percentiles of the $\log_{10}$ transformed ratios of mRNA copies per microgram of total RNA to 18S rRNA copies ($\times 10^{-6}$) per microgram of total RNA are reported in Table 5A, and the non-normalized, non-log transformed absolute mRNA copy numbers copies per microgram of total RNA and 18S rRNA copies ($\times 10^{-6}$) per microgram of total RNA are reported in Table 5B.

TABLE 5A 18S rRNA Normalized, $\log_{10}$ - Transformed Levels of mRNA in Urinary Cells.

| Type of mRNA | Acute Cellular Rejection (N = 43 samples 34 patients) | No Rejection Group (N = 163 samples 126 patients) | Stable (No Biopsy) Group (N = 1540 samples 201 patients) | P Value† | Borderline (N = 19 samples 17 patients) | Antibody Mediated Rej (N = 10 samples 9 patients) | Other (N = 9 samples 8 patients) | | P Value‡ ACR Vs. | P-Value‡ No Reject Vs. | P Value‡ Stable Vs. |
|---|---|---|---|---|---|---|---|---|---|---|---|
| CD3ε | 0.601 (-0.233, 0.995) | -0.504 (-1.074, 0.247) | -0.236 (-0.891, 0.341) | <0.0001 | -0.024 (-0.703, 0.305) | 0.022 (-0.306, 0.385) | -0.052 (-0.541, 0.429) | No rejection Stable Borderline | <0.0001 <0.0001 0.04 | 0.11 0.24 | 0.38 |
| Perforin | 0.289 (-0.160, 0.817) | -0.689 (-1.215, 0.028) | -0.688 (-1.279, -0.056) | <0.0001 | -0.327 (-0.612, 0.087) | -0.560 (-0.933, -0.164) | -0.107 (-0.654, 0.287) | No rejection Stable Borderline | <0.0001 <0.0001 0.01 | 0.30 0.15 | 0.07 |
| Granzyme B | 0.261 (-0.222, 0.721) | -0.523 (-0.910, 0.078) | -0.430 (-1.039, 0.140) | <0.0001 | -0.424 (-1.168, 0.368) | -0.063 (-1.072, 0.380) | 0.354 (-0.662, 0.611) | No rejection Stable Borderline | <0.0001 <0.0001 0.01 | 0.80 0.95 | 0.94 |
| IP-10 | -0.114 (-0.655, 0.489) | -1.029 (-1.534, -0.362) | -0.874 (-1.424, -0.186) | <0.0001 | -0.903 (-1.205, -0.531) | -0.986 (-1.399, 0.150) | 0.314 (-0.028, 0.948) | No rejection Stable Borderline | <0.0001 <0.0001 0.002 | 0.09 0.61 | 0.91 |
| CXCR3 | 0.082 (-0.680, 0.338) | -0.241 (-0.872, 0.259) | -0.055 (-0.718, 0.455) | 0.06 | -0.458 (-0.932, 0.229) | -0.419 (-1.186, 0.074) | -0.289 (-1.340, 0.006) | No rejection Stable Borderline | 0.10 0.66 0.21 | 0.02 0.66 | 0.21 |
| CD103 | -0.929 (-1.619, -0.517) | -1.298 (-1.748, -0.830) | -1.308 (-1.779, -0.848) | 0.13 | -1.145 (-1.948, -0.483) | -1.184 (-2.040, -1.014) | -1.369 (-1.534, -1.018) | No rejection Stable Borderline | 0.05 0.05 0.59 | 0.96 0.70 | 0.72 |
| TGF-B1 | 0.928 (0.499, 1.181) | 0.756 (0.356, 1.113) | 0.837 (0.424, 1.242) | 0.11 | 0.584 (0.372, 1.341) | 1.088 (1.004, 1.288) | 0.709 (0.139, 0.830) | No rejection Stable Borderline | 0.08 0.51 0.16 | 0.05 0.55 | 0.28 |
| PI-9 | 0.604 (0.155, 0.782) | 0.383 (-0.105, 0.816) | 0.445 (-0.137, 0.962) | 0.37 | 0.239 (-0.104, 0.681) | 0.787 (0.714, 0.984) | 0.438 (0.332, 0.907) | No rejection Stable Borderline | 0.14 0.42 0.18 | 0.28 0.75 | 0.49 |

TABLE 5A-continued 18S rRNA Normalized, Log$_{10}$ - Transformed Levels of mRNA in Urinary Cells.

| Type of mRNA | Acute Cellular Rejection (N = 43 samples 34 patients) | No Rejection Group (N = 163 samples 126 patients) | Stable (No Biopsy) Group (N = 1540 samples 201 patients) | P Value† | Borderline (N = 19 samples 17 patients) | Antibody Mediated Rej (N = 10 samples 9 patients) | Other (N = 9 samples 8 patients) | | P Value‡ ACR Vs. | P-Value‡ No Reject Vs. | P Value‡ Stable Vs. |
|---|---|---|---|---|---|---|---|---|---|---|---|
| 18S rRNA | 3.365 (2.798, 3.740) | 2.857 (2.427, 3.276) | 2.951 (2.491, 3.339) | 0.0002 | 2.994 (2.370, 3.442) | 3.145 (2.919, 3.221) | 3.310 (2.791, 3.326) | No rejection Stable Borderline | 0.0001 0.0001 0.04 | 0.16 0.47 | 0.83 |

* Levels of mRNA were measured with the use of preamplification enhanced real time quantitative PCR assays using gene specific oligonucleotide pairs and TaqMan probes. Median Copy Number (lower, upper quartiles) of each mRNA measure, normalized by 18s rRNA and log$_{10}$-transformed are shown. Matched (urine collected minus 3 days to plus 1 day of biopsy) and quality control passed urine samples were included for those who underwent a biopsy, whereas all quality control passed urine samples collected longitudinally were included for the Stable (no biopsy) group.
†P values calculated using Kruskal-Wallis test of no differences among the Acute Cellular Rejection biopsy group, No Rejection biopsy group and Stable (no biopsy) group.
‡P values calculated using Mann-Whitney test of no difference between two groups.

TABLE 5B

Absolute Levels of mRNA in Urinary Cells.*

| Type of mRNA | Acute Cellular Rejection (N = 43 samples 34 patients) | No Rejection Group (N = 163 samples 126 patients) | Stable (No Biopsy) Group (N = 1540 samples 201 patients) | P Value† | Borderline (N = 19 samples 17 patients) | Antibody Mediated Rej (N = 10 samples 9 patients) | Other (N = 9 samples 8 patients) | | P Value‡ ACR Vs. | P-Value‡ No Reject Vs. | P Value‡ Stable Vs. |
|---|---|---|---|---|---|---|---|---|---|---|---|
| CD3ε | 8826 (2253, 21790) | 356 (13, 1812) | 497 (102, 2431) | <0.0001 | 944 (81, 4388) | 943 (240, 2138) | 3192 (536, 4713) | No rejection Stable Borderline | <0.0001 <0.0001 0.001 | 0.06 0.23 | 0.51 |
| Perforin | 4119 (1093, 11148) | 223 (13, 1208) | 201 (13, 985) | <0.0001 | 398 (192, 1564) | 273 (153, 1646) | 1595 (470, 2900) | No rejection Stable Borderline | <0.0001 <0.0001 0.0003 | 0.72 0.20 | 0.13 |
| Granzyme B | 3304 (743, 11571) | 337 (64, 1332) | 342 (63, 1663) | <0.0001 | 614 (13, 1944) | 1123 (60, 2578) | 4605 (110, 10574) | No rejection Stable Borderline | <0.0001 <0.0001 0.0009 | 0.60 0.72 | 0.87 |
| IP-10 | 1445 (236, 7362) | 75 (13, 382) | 130 (13, 683) | <0.0001 | 196 (13, 798) | 76 (13, 2104) | 4203 (859, 15162) | No rejection Stable Borderline | <0.0001 <0.0001 0.0003 | 0.02 0.43 | 0.94 |
| CXCR3 | 2122 (618, 6348) | 393 (123, 1616) | 770 (180, 2899) | <0.0001 | 325 (60, 1782) | 203 (67, 2472) | 664 (68, 1837) | No rejection Stable Borderline | <0.0001 0.001 0.01 | 0.003 0.78 | 0.22 |
| CD103 | 234 (63, 596) | 13 (13, 135) | 13 (13, 162) | <0.0001 | 13 (13, 272) | 13 (13, 161) | 59 (13, 236) | No rejection Stable Borderline | <0.0001 <0.0001 0.04 | 0.35 0.35 | 0.56 |
| TGF-B1 | 15142 (5187, 57855) | 4589 (896, 14668) | 5838 (1544, 21690) | 0.0001 | 5022 (992, 22670) | 15439 (8379, 28928) | 3169 (1510, 14065) | No rejection Stable Borderline | <0.0001 0.0002 0.01 | 0.05 0.72 | 0.73 |
| PI-9 | 9782 (1680, 28890) | 1756 (335, 9000) | 2153 (409, 11798) | 0.002 | 2180 (765, 9355) | 7527 (4389, 14564) | 5586 (1329, 6358) | No rejection Stable Borderline | 0.0002 0.001 0.05 | 0.22 0.64 | 0.99 |
| 18S rRNA | 2320 (628, 5500) | 720 (267, 1866) | 894 (310, 2180) | 0.0002 | 985 (234, 2770) | 1398 (830, 1664) | 2040 (619, 2120) | No rejection Stable Borderline | 0.0001 0.0001 0.04 | 0.16 0.47 | 0.83 |

*Median absolute copy number (lower, upper quartiles) of each mRNA measure, without 18S rRNA normalization and without log-transformation and median absolute copy number (lower, upper quartiles) of 18S rRNA (×10$^{-6}$) without log-transformation are shown. Matched (urine collected minus 3 days to plus 1 day of biopsy) and quality control passed urine samples were included for those who underwent a biopsy, whereas all quality control passed urine samples collected longitudinally were included for the Stable (no biopsy) group.
†P values calculated using Kruskal-Wallis test of no differences among the Acute Cellular Rejection biopsy group, No Rejection biopsy group and Stable (no biopsy) group.
‡P values calculated using Mann-Whitney test of no difference between two groups.

Acute Antibody Mediated Rejection Biopsies Group.

Among the 25 Banff acute antibody mediated rejection biopsies (23 for-cause and 2 surveillance biopsies) from 16 patients, 8 were graded as AMR grade I-ATN, 15 as AMR grade II-capillary, 1 as AMR grade III-arterial and 1 was not graded. Among the 25 AMR biopsies, 12 biopsies did not have matched urine specimens, and 3 of the matched urine specimens failed PCR assay QC parameters. Among the 10 AMR biopsies (8 for-cause and 2 surveillance biopsies) with matched urine specimens, 4 were graded as AMR grade I-ATN and the remaining 6 biopsies were graded as AMR grade II-capillary. Urinary cell mRNA levels in the 10 QC-passed urine specimens matched to 10 AMR biopsies from 9 patients were used to calculate the median, $25^{th}$ and $75^{th}$ percentiles of the $\log_{10}$ transformed ratios of mRNA copies per microgram of total RNA to 18S rRNA copies ($\times 10^{-6}$) per microgram of total RNA reported in Table 5A and the non-normalized, non-log transformed absolute mRNA copy numbers per microgram of total RNA and 18S rRNA copies ($\times 10^{-6}$) per microgram of total RNA reported in Table 5B.

Borderline Biopsies Group.

Among the 36 Banff Borderline biopsies (26 for-cause and 10 surveillance biopsies) from 29 patients, 9 biopsies did not have matched urine specimens, and 8 of the matched urine specimens failed PCR assay QC parameters. Urinary cell mRNA levels in the 19 QC-passed urine specimens matched to 19 Borderline biopsies (14 for-cause and 5 surveillance) from 17 patients were used to calculate the median, $25^{th}$ and $75^{th}$ percentiles of the $\log_{10}$ transformed ratios of mRNA copies per microgram of total RNA to 18S rRNA copies ($\times 10^{-6}$) per microgram of total RNA reported in Table 5A, and the non-normalized, non-log transformed absolute mRNA copy numbers copies per microgram of total RNA and 18S rRNA copies ($\times 10^{-6}$) per microgram of total RNA reported in Table 5B.

Other Biopsy Group

Seventeen biopsies (all for-cause) from 13 patients showed evidence of BKV/polyoma nephropathy (n=16) or bacterial infection/Pyelonephritis (n=1). Two biopsies (all for-cause) from 2 patients were classified as chronic allograft nephropathy. Among these 19 biopsies, matched urine was available in 9, all passing QC parameters, and urinary cell mRNA levels in these 9 urine specimens from 8 patients were used to calculate the median, $25^{th}$ and $75^{th}$ percentiles of the $\log_{10}$ transformed ratios of mRNA copies per microgram of total RNA to 18S rRNA copies ($10^{-6}$) per microgram of total RNA reported in Table 5A, and the non-normalized, non-log transformed absolute mRNA copy numbers copies per microgram of total RNA and 18S rRNA copies ($10^{-6}$) per microgram of total RNA reported in Table 5B.

No Biopsy Group:

There were 265 kidney transplant recipients who never had a recorded biopsy and 202 of them met the following criteria and were included in the Stable (no biopsy) group: (i) average of serum creatinine values assessed at 6, 9, and 12 months post-transplantation less than or equal to 2.0 mg/dl (in 3 of 202 patients, 6-, 9-, and 12-month creatinine levels were not available but their 24-month creatinine level was less than or equal to 2.0 mg/dl); (ii) no graft loss or death during the first 12 months following transplantation; (iii) no treatment for acute rejection; and (iv) no cytomegalovirus or BK virus infection. These 202 patients prospectively provided a total of 1848 urine specimens for mRNA profiling and 1540 urine specimens passed QC parameters; the urinary cell mRNA levels in these 1540 QC-passed urine specimens from 201 patients were used generate the box and whisker plots shown in FIG. 2. The median, $25^{th}$ and $75^{th}$ percentiles of the $\log_{10}$ transformed ratios of mRNA copies per microgram of total RNA to 18S rRNA copies ($10^{-6}$) per microgram of total RNA are reported in Table 5A, and the non-normalized, non-log transformed absolute mRNA copy numbers per microgram of total RNA, and 18S rRNA copies ($10^{-6}$) per microgram of total RNA are reported in Table 5B.

Of the remaining 63 of 265 patients who did not have a biopsy, 47 had no serum creatinine values beyond 5 months post-transplantation, 4 had serum creatinine values at 6-, 9-, and/or 12-months that averaged>2.0 mg/dl, 9 were treated for CMV, BKV infection or both, 1 lost his/her graft within the first 12 months, and 2 patients died within the first 12 months. A total of 272 urine specimens collected from these 63 patients who failed to meet the criteria for the Stable (no biopsy) group were mRNA profiled and 237 passed QC parameters. The urinary cell mRNA data from these 63 patients were not analyzed.

Example 4: Statistical Analysis

Figure 2:
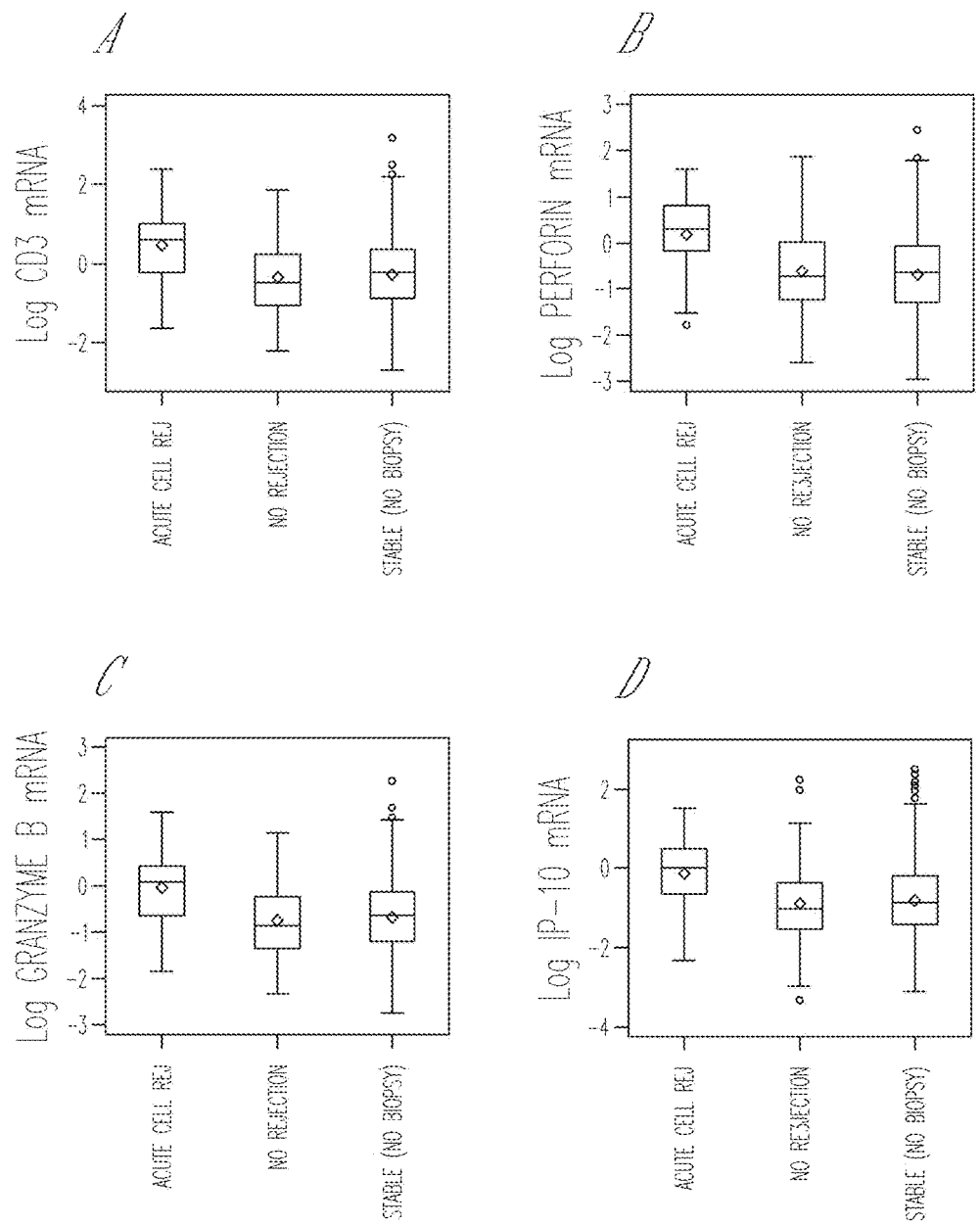
FIG. 2A-2H graphically illustrate the levels of mRNA in urinary cells. Box-and-whisker plots show the $\log_{10}$-transformed ratios of mRNA copies per microgram of total RNA to 18S ribosomal RNA (rRNA) copies ($\times 10^{-6}$) per microgram of total RNA for CD3ε (FIG. 2A), perforin (FIG. 2B), granzyme B (FIG. 2C), interferon-inducible protein 10 (IP-10) (FIG. 2D), CXCR3 (FIG. 2E), CD103 (FIG. 2F), transforming growth factor β1 (TGF-β1) (FIG. 2G), and proteinase inhibitor 9 (PI-9) (FIG. 2F) in 43 urine samples matched to 43 biopsy specimens (from 34 patients) showing acute cellular rejection, 163 urine samples matched to 163 biopsy specimens (from 126 patients) showing no rejection, and 1540 longitudinally collected urine samples from 201 patients with stable graft function who did not undergo biopsy. The horizontal line within each box represents the median, the bottom and top of each box represent the 25th and 75th percentile values, and the I bars represent the 10th and 90th percentile values; the diamond indicates the mean, and circles indicate outliers. The mRNA levels of CD3ε, perforin, granzyme B, and IP-10 differed significantly among the three groups (P<0.001 for all comparisons), but not the levels of CXCR3 (P=0.06), CD103 (P=0.13), TGF-β1 (P=0.11), and proteinase inhibitor 9 (PI-9; P=0.38). P values are based on the Kruskal-Wallis test, with the $\log_{10}$-transformed, 18S-normalized mRNA levels treated as the dependent variable. Pairwise group comparisons by means of the Mann-Whitney test showed that the mRNA levels for CD3, perforin, granzyme B, and IP-10 in patients with acute cellular rejection were significantly higher than the levels in those with specimens showing no rejection (P<0.001 for each mRNA) and in those with stable graft function (P<0.001 for each mRNA).
Figure 2:
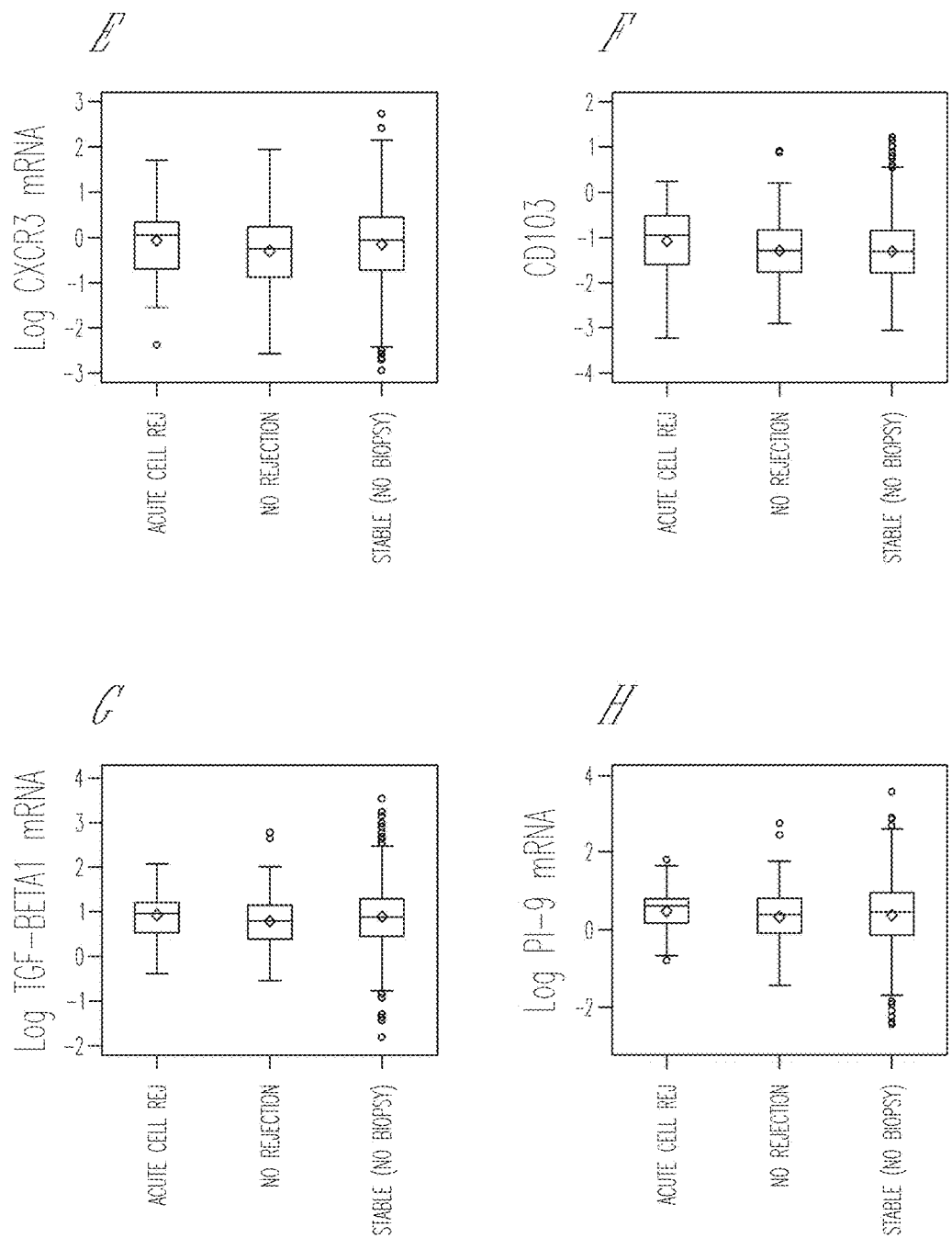

Each mRNA measure was initially normalized by dividing its copy number by the copy number of 18S rRNA ($\times 10^{-6}$). The distribution of each 18S-normalized mRNA measure exhibited considerable positive skewness, which was substantially reduced by use of a log transformation. Box and whisker plots, and the non-parametric Kruskal-Wallis and Mann-Whitney tests were used to examine biopsy group differences in each 18S-normalized mRNA measurement (FIG. 2 and Table 5A). Data analysis performed using non-normalized mRNA measures are presented in Table 5B.

Fitting the Model

Logistic regression analyses predicting biopsy status (Acute Cellular Rejection vs. No Rejection biopsies) from all possible combinations of the eight log-transformed, 18S-normalized mRNA measures and log-transformed 18S rRNA obtained from the matched urine samples were performed. From among those models in which each of the predictors was statistically significant at P<0.05, one was provisionally selected that had the greatest log-likelihood and greatest area under the receiver-operating-characteristic (ROC) curve as the best-fitting model. After internal validation (described below), the regression estimates for this best-fitting model defined a new diagnostic signature whose ability to accurately discriminate acute cellular rejection biopsies from No Rejection biopsies was then evaluated. The ability of this diagnostic signature to discriminate (i.e., correctly classify) the 43 acute cellular rejection biopsies from the 163 No Rejection biopsies was evaluated by the area under the ROC curve (AUC) of the fitted model, as well as sensitivity and specificity for diagnosing acute cellular rejection. An AUC of 1.0 indicates perfect concordance; i.e., every acute cellular rejection biopsy has a higher score on the diagnostic signature than every non-acute cellular rejection biopsy. An AUC of 0.50 would indicate that the ability of the diagnostic signature to differentiate an acute cellular rejection biopsy from a biopsy without acute cellular rejection is no better than chance. Sensitivity and specificity were based on selection of the cutpoint on the ROC that maximized Youden's index (=sensitivity+specificity−1) (Le C T, Statistical Methods in Medical Research 15:571-84 (2006)). The ability of the model to accurately predict the probability of an acute cellular rejection was assessed with the Hosmer-Lemeshow test (Tripepi et al., Nephrol Dial Transplant 25:1402-5 (2010)). A secondary analysis examining the ability of the diagnostic signature to discriminate urine samples matched to acute cellular rejection biopsies from urine samples provided by Stable (no biopsy) patients was also performed.

Bootstrap Model Selection and Internal Validation of the Fitted Model.

The generalizability of the initial model selection to other data sets was initially evaluated using bootstrap re-sampling methods as implemented in Harrell's rms software package (Efron & Tibshirani, An Introduction to the Bootstrap, New York: Chapman and Hall (1993); Harrell et al, Stat Med 15:361-87 (1996); Austin & Tu, The American Statistician 58:131-7 (2004)). Backward elimination with SLS=0.50 (SLS: Significance Level to Stay in the model) was used to identify the best subset of the 9 candidate predictors (Eight 18S-normalized mRNA measures and 18S rRNA) in each of 500 data sets obtained by sampling with replacement from the test data set. The software uses the proportion of samples in which each predictor remains in the final backwards elimination model to inform the selection of a "best" subset of predictors.

To evaluate the internal validity of the 3-gene model, it was fit to 500 new bootstrap samples of the data from which optimism-adjusted (Schmittgen & Livek, Nat Protoc 3:1101-8 (2008)) estimates of the AUC, Cox's intercept and slope were obtained (Cox, Biometrika 45:562-5 (1958); Miller et al., Med Decis Making 13:49-58 (1993); Steyerberg E. Clinical prediction models: A practical approach to development, validation and updating. New York: Springer (2009); Steyerberg, Epidemiology 21:128-38 (2010)). The calibration plot was also obtained from optimism-adjusted estimates of the AUC, Cox's intercept and slope (Harrell et al. Stat Med 15:361-87 (1996)). Cox's intercept (also called "calibration in the large") is an estimate of the degree to which the predicted acute cellular rejection probabilities are biased high or low relative to the observed probabilities, while the slope is a measure of over-fitting of the model (Tripepi et al., Nephrol Dial Transplant 25:1402-5 (2010); Efron B, Tibshirani R. An introduction to the bootstrap. New York: Chapman and Hall; (1993)). An intercept value of 0.0 would indicate no bias, while a slope of 1.0 would indicate no overfitting. Slope values<0.90 are generally regarded as indicating overfitting problems.

Example 5: External Validation of the Diagnostic Signature

Since an external validation set represents the most robust approach for the validation of prediction models, an external validation study of the diagnostic signature developed in the CTOT-04 study was undertaken. Biopsy matched urine samples from all 24 Banff acute cellular rejection (ACR) biopsies and a random selection of 47 non-ACR (No Rejection) biopsies from 64 kidney graft recipients enrolled in the NIH-CTOT-01 study were used by SACCC to construct an external validation set. The samples used as the external validation set were independently collected, blinded urine samples from the CTOT-01 study. The 64 subjects from which the samples were collected are described in Table 2.

A total of 280 subjects received a kidney transplant under the CTOT-01 protocol. Post-transplant follow-up yielded 180 surveillance biopsies at Month 6, 108 for-cause biopsies during the first 6 months post-transplant, and 52 for-cause biopsies after the first 6 months. Out of these 340 biopsies, all 24 acute cellular rejection biopsies and a random selection of 47 non-acute cellular rejection (No Rejection) biopsies in 64 subjects were used to construct the external validation set (Table 2) by the NIH-sponsored SACCC, independent of the CTOT-04 investigators. The intent of the random sampling was to have twice as many non-acute cellular rejection biopsies as acute cellular rejection biopsies, all with matching specimens (one non-acute cellular rejection biopsy was inadvertently selected twice, resulting in 47 rather than the targeted 48 non-acute cellular rejection biopsies). Power calculations had shown that if the population sensitivity and specificity of the diagnostic signature were both 75%, a sample size of 22 acute cellular rejections and 44 no rejection biopsies would provide 98% power to detect a significant 2×2 association between the diagnostic signature (dichotomized at the pre-specified cutpoint) and biopsy status using a two-tailed, alpha=0.05 test; even if the population sensitivity and specificity of the diagnostic signature were each only 70%, the validation study would have 88% power to reject the null hypothesis of no association.

The external validation study, with the Weill Cornell Gene Expression Monitoring (GEM) Core remaining blinded regarding diagnostic status until PCR assay results were reported to the NIH-sponsored SACCC, was carried out in the following fashion: (1) the CTOT-01 gene expression core at the Cleveland Clinic provided to the Weill Cornell CTOT-04 gene expression monitoring core an aliquot of stored cDNA from the total RNA originally isolated from the urine cell pellets of the CTOT-01 subjects; (2) the Weill Cornell gene expression core measured levels of 18S rRNA and TGF-$\beta$1 to ensure that the CTOT-01 samples met the CTOT-04 quality control criteria—TGF-$\beta$1 mRNA copy number being greater than or equal to 100 copies and the 18S rRNA copy number being greater than or equal to $5 \times 10^7$ in one microgram of total RNA; (3) the Weill Cornell gene expression monitoring core measured levels of CD3$\epsilon$ mRNA, IP-10 mRNA and 18S rRNA (the three genes used to calculate the diagnostic signature) using the same protocol to measure transcript levels as was used in the CTOT-04 study, and reported the transcript levels to the NIH-sponsored SACCC; (4) the SACCC then un-blinded the diagnostic status of the 71 biopsies and independent data analyses were performed.

Among the 71 cDNA samples assayed for the levels of transcripts included in the diagnostic signature, 21 subjects provided 24 samples with Banff acute cellular rejection grade IA or higher and 43 subjects provided the remaining 47 samples with No Rejection biopsies (biopsies without acute cellular rejection, antibody mediated rejection (AMR) or Borderline changes). Of the 24 acute cellular rejection biopsies, 11 were classified as Banff acute cellular rejection grade IA, 4 as IB), 7 as IIA, 1 as IIB), and 1 as III and these resulted from 17 for-cause biopsies and 7 surveillance biopsies. Of the 47 non-acute cellular rejection biopsies, 19 were for-cause biopsies and 28 were surveillance biopsies.

In the process of confirming that the 71 cDNA samples satisfied the QC criteria used in CTOT-04, the original Cleveland Clinic PCR assay results for 18s rRNA and TGF-$\beta$1 mRNA were compared to Cornell's assay results. Although the correlations between corresponding measures were satisfactory (0.76 for 18s and 0.74 for TGF-$\beta$1), the mean levels were substantially lower for the Cornell PCR assays. Therefore the ratio of TGF-$\beta$1 copy number from the Cleveland Clinic Core and the TGF-$\beta$1 copy number from the Weill Cornell Core was calculated (TGF-$\beta$1 was measured at both Cores using identical oligonucleotide primer pair and TaqMan probe) and used this correction factor (i.e., multiplier) to adjust the values for CD3$\epsilon$ mRNA copy number (not measured originally by the Cleveland Clinic Core) and IP-10 mRNA copy number (measured originally by the Cleveland Clinic Core but using a different set of primers and probe than the ones used at the Weill Cornell Core). These adjusted values and the 18S rRNA copy numbers from the Cleveland Clinic Core were then used in the CTOT-04 equation to calculate CTOT-01 values of the diagnostic signature.

Longitudinal Trajectories.

Once the diagnostic signature had been identified and validated, the prospective trajectory, from the time of transplant, of this signature in three patient groups was examined. In the Stable (no biopsy) group and the group who had no abnormal biopsies (Only No Rejection Biopsies group) all QC-passed urine samples collected during the first 400 days post-transplant were included. For those patients who experienced an acute cellular rejection and had no antibody mediated rejection, borderline or BKV nephropathy biopsies prior to their first acute cellular rejection biopsy, all QC-passed urine samples were included that were collected from the time of transplant until either four days prior to the first acute cellular rejection biopsy or 400 days post-transplant, whichever came first. For each of these three groups, the pooled within-person average trajectory was estimated by fitting a LOESS (locally estimated scatterplot smoothing) model predicting the diagnostic signature from days post-transplantation, with the patient as a covariate.

This same methodology was used to examine the retrospective trajectories of the diagnostic signature, looking backwards from the time of biopsy in two groups—the group with biopsy findings showing acute cellular rejection and the group with biopsy findings showing no rejection. For biopsies of both types that occurred during the first 400 days post-transplant, all QC-passed urine samples obtained prior to or at the time of the biopsy were included. Again, a LOESS model, using the patient as a covariate, was used to estimate and compare the average within-person retrospective trajectories for these two groups.

All analyses were performed with the use of SAS software, version 9.3 (SAS Institute), or Harrell's R package RMS software, version 2.12.2 (see website at cran.r-project.org/web/packages/rms/rms).

Example 6: Additional Tests of Diagnostic Signature

This Example provides additional information regarding the development of the diagnostic signature.

Accuracy of the Diagnostic Signature Across Transplant Sites

The total number of acute cellular rejection biopsies with matched and QC-passed urine samples was 43 and among the 43, 22 acute cellular rejection biopsies were from Northwestern University Feinberg School of Medicine, Chicago, Ill., 10 from Hospital of University of Pennsylvania, Philadelphia, Pa.; 1 from University of Wisconsin Hospital and Clinics, Madison, Wis.; 7 from New York Presbyterian Hospital-Columbia University Medical Center, New York, N.Y. and 3 from New York Presbyterian Hospital-Weill Cornell Medical Center, New York, N.Y. The total number of No Rejection biopsies with matched and QC-passed urine samples was 163 and among the 163, 88 No Rejection biopsies were from Northwestern University Feinberg School of Medicine, Chicago, Ill., 15 from Hospital of University of Pennsylvania, Philadelphia, Pa.; 5 from University of Wisconsin Hospital and Clinics, Madison, Wis.; 28 from New York Presbyterian Hospital-Columbia University Medical Center, New York, N.Y. and 27 from New York Presbyterian Hospital-Weill Cornell Medical Center, New York, N.Y. Excluding the University of Wisconsin data, where there was only one acute cellular rejection biopsy, the AUCs of the diagnostic signature for the other four centers were 0.85, 0.89, 0.82, and 0.90, respectively (all P<0.0001), indicating that the diagnostic signature discriminates acute cellular rejection from No rejection biopsies similarly across these 4 centers; all four 95% CI for these AUCs included the range 0.83 to 0.89. Recognizing that the statistical power would be relatively low, also performed was a logistic regression predicting acute cellular rejection vs. No rejection biopsy from the diagnostic signature, center (treated as a categorical factor), and the center×signature interaction term; the interaction term did not remotely approach statistical significance (P=0.30); hence, there was no signal suggesting that the relationship of the diagnostic signature to biopsy status differs by center.

External Validation of the Diagnostic Signature

The receiver operating characteristic curve portraying the ability of the 3-gene diagnostic signature—calculated from 18S-normalized CD3ε mRNA, 18S-normalized IP-10 mRNA, and 18S rRNA (all logged)—to discriminate acute cellular rejection biopsies from No Rejection biopsies in the CTOT-01 external validation urine samples had an area under the curve (AUC) of 0.74 (95% CI: 0.61 to 0.86, P=0.0002) (FIG. 3D). The AUC for the diagnostic signature in the validation CTOT-01 cohort was lower than the original CTOT-04 AUC of 0.85 (95% CI: 0.78 to 0.91, P<0.0001) (FIG. 3A), but not significantly lower (P=0.13).

Using the original CTOT-04 diagnostic signature cutoff value of −1.213, acute cellular rejection in the CTOT-01 external validation set was predicted with a specificity of 72% (95% CI: 62% to 83%) and a sensitivity of 71% (95% CI: 53% to 89%). The differences between these and the corresponding values in CTOT-04 did not approach statistical significance (both P>0.35).

Specificity of the Diagnostic Signature

The 3-gene diagnostic signature (18S-normalized CD3ε mRNA, 18S-normalized IP-10 mRNA and 18S rRNA, all logged) was generated by comparing levels of mRNA in matched urine specimens from kidney graft recipients with biopsy confirmed Banff acute cellular rejection (acute cellular rejection biopsy group, 43 samples from 34 patients) with levels of mRNA in matched urine specimens from kidney graft recipients with normal biopsy results or non-specific findings (163 samples from 126 patients, No Rejection Biopsy Group), and did not include levels of mRNA in matched urine specimens from those with biopsies showing borderline changes, acute antibody mediated rejection, chronic allograft nephropathy or BK viral-associated nephropathy.

The "No Rejection biopsy group" included biopsies that displayed histological features such as acute tubular necrosis (n=67), tubular atrophy (n=61), interstitial fibrosis (n=52), glomerulosclerosis (n=23), vascular narrowing (n=17), calcineurin toxicity (n=12) and/or recurrent disease (n=2) and not infrequently more than one type of allograft pathology was observed in a single biopsy. Also, 107 of the 163 biopsies were performed for suspected rejection/graft dysfunction (for-cause biopsies) and the remaining 56 biopsies were surveillance (protocol) biopsies.

Inclusion of Additional Biopsy Diagnoses

The performance of the 3-gene diagnostic signature was analyzed after inclusion in the non-acute cellular rejection group of ALL matched and QC-passed urine samples from the kidney graft recipients with biopsies showing borderline changes (19 samples from 17 patients), acute antibody mediated rejection ([AMR], 10 samples from 9 patients), chronic allograft nephropathy ([CAN], 2 samples from 2 patients) or BK viral-associated nephropathy ([BKVN], 6 samples from 5 patients).

A comparison of the levels of mRNA in the 43 matched urine specimens from 34 kidney graft recipients with biopsy confirmed Banff acute cellular rejection grade 1A or higher with all available non-acute cellular rejection biopsy matched, QC-passed urine samples (n=200 samples) from 143 patients showed that the signature is diagnostic of acute cellular rejection with 77% specificity (95% CI: 71 to 83%) and 79% sensitivity (95% CI: 67 to 91%) (AUC=0.83, 95% CI: 0.77 to 0.89, P<0.0001) and that the performance of the signature is very similar to the original analysis that was restricted to acute cellular rejection vs. No Rejection biopsy group (that is without inclusion of the 37 urine samples from those with borderline changes, acute antibody mediated rejection (AMR), chronic allograft nephropathy or BK viral-related nephropathy).

Also analyzed was the performance of the 3-gene diagnostic signature comparing levels of mRNA in the 43 matched urine specimens from 34 kidney graft recipients with biopsy confirmed Banff acute cellular rejection grade 1A or higher with levels of mRNA in just the 31 matched and QC-passed urine samples from the kidney graft recipients with biopsies showing Borderline changes (19 samples from 17 patients), acute antibody mediated rejection (10 samples from 9 patients), or chronic allograft nephropathy (2 samples from 2 patients). Despite the sample size for the comparison group being very much smaller than in the previous analyses, this analysis showed that the signature is diagnostic of acute cellular rejection with 71% specificity (95% CI: 55 to 87%) and 79% sensitivity (95% CI: 67 to 91%) (AUC=0.78, 95% CI: 0.68 to 0.89, P<0.0001) and that its performance was not significantly different from that observed when comparing the acute cellular rejection biopsy group with the No Rejection biopsy group.

Banff Acute Cellular Rejection Biopsy Grade and the Diagnostic Signature Score.

There was a progressive trend towards lower diagnostic signature scores when comparing Banff grades II and III to grade I but the differences among the acute cellular rejection Banff grades (IA, IB, IIA, IIB, and III) were not statistically significant (P=0.99, One Way ANOVA) (see Table 6). While the mean score of the diagnostic signature was numerically higher in Banff grade I vs. Banff grades II+III but this difference was not statistically significant (−0.3687 vs. −0.4582, P=0.83, 2-tailed t-test for two-group comparison)

TABLE 6

Biopsy Banff Grade and Mean Diagnostic Score.

| Biopsy Group | N | Mean* |
|---|---|---|
| Mild acute cellular rejection (Grade IA) | 19 | −0.368 |
| Mild acute cellular rejection (Grade IB) | 10 | −0.370 |
| Moderate acute cellular rejection (Grade IIA) | 11 | −0.423 |
| Moderate acute cellular rejection (Grade IIB) | 2 | −0.536 |
| Severe acute cellular rejection (Grade III) | 1 | −0.685 |

*Percutaneous needle biopsies of the kidney allografts were categorized with the use of Banff Classification and the mean levels of the diagnostic signature (CD3ε +IP10 +18s) were compared across acute cellular rejection Banff grades IA, IB, IIA, IIB, and III in a one-way analysis of variance. There were no significant differences among the Banff grades (P = 0.99).

The Diagnostic Signature in For-Cause Versus Surveillance Biopsies.

The 3-gene signature was diagnostic of acute cellular rejection with 80% specificity (95% CI: 73 to 88%) and 79% sensitivity (95% CI: 66 to 92%) (AUC=0.85, 95% CI: 0.79 to 0.92, P<0.0001) when the data were analyzed using only the 38 for-cause acute cellular rejection biopsies and the 107 for-cause No Rejection biopsies. The performance characteristics of the diagnostic signature were nearly identical to the original analysis using both for-cause biopsies and protocol biopsies (43 acute cellular rejection biopsies vs. 163 No Rejection biopsies, 78% specificity [95% CI: 71 to 84%] and 79% sensitivity [95% CI: 67 to 91%] [AUC=0.85, 95% CI: 0.78 to 0.91, P<0.0001]).

The 3-gene signature was also strongly associated with the biopsy diagnosis when the analysis was restricted to surveillance No Rejection biopsies. Analysis of 43 acute cellular rejections vs. 56 surveillance No Rejection biopsies showed that acute cellular rejection was predicted with 73% specificity (95% CI: 62 to 85%) and 79% sensitivity (95% CI: 67 to 91%) and the AUC was 0.83 (95% CI: 0.75 to 0.91, P<0.0001).

The Diagnostic Signature in Clinical Versus Subclinical Acute Cellular Rejection Among the 43 acute cellular rejection biopsies from the CTOT-04 patients, 38 biopsies were for-cause biopsies and the remaining 5 were surveillance biopsies and among the 163 No Rejection biopsies, 107 were for-cause biopsies and 56 were surveillance biopsies.

The mean levels of the 3-gene diagnostic signature did not differ significantly between the 38 for-cause acute cellular rejection biopsies and the 5 surveillance acute cellular rejection biopsies (P=0.78). The same is true for comparison of the 107 for-cause and the 56 surveillance No Rejection biopsies (P=0.66). Sensitivity of diagnostic signature was 79% in 38 for-cause biopsies and 80% in surveillance biopsies (No difference: P=1.00). Specificity of the diagnostic signature was 80% in the 107 for-cause biopsies and 73% in the surveillance biopsies (P=0.32)

Early or Late Acute Cellular Rejection and the Diagnostic Signature.

In order to examine whether the diagnostic signature tends to be higher (or lower) at the time of an early acute cellular rejection compared to a late acute cellular rejection, the 43 acute cellular rejections with matching urine samples were arbitrarily classified as early acute cellular rejections based on the acute cellular rejection occurring during the first 180 days post-transplantation or late acute cellular rejections based on the acute cellular rejection occurring thereafter; 19 acute cellular rejections qualified as early acute cellular rejections and the remaining 24 acute cellular rejections as late acute cellular rejections. The mean diagnostic signature score at the time of biopsy was −0.43 (95% CI: −1.04 to +0.18) for the early acute cellular rejections and −0.37 (95% CI: −0.88 to +0.14) for the late acute cellular rejections (P=0.87 by t-test). The correlation between the diagnostic signature at the time of acute cellular rejection and time since transplant (treated continuously) was also evaluated, and the analysis showed absolutely no relationship (r=0.00, P=0.97). Thus the level of the diagnostic signature at the time of an acute cellular rejection did not vary by time since transplant.

Figure 5A:
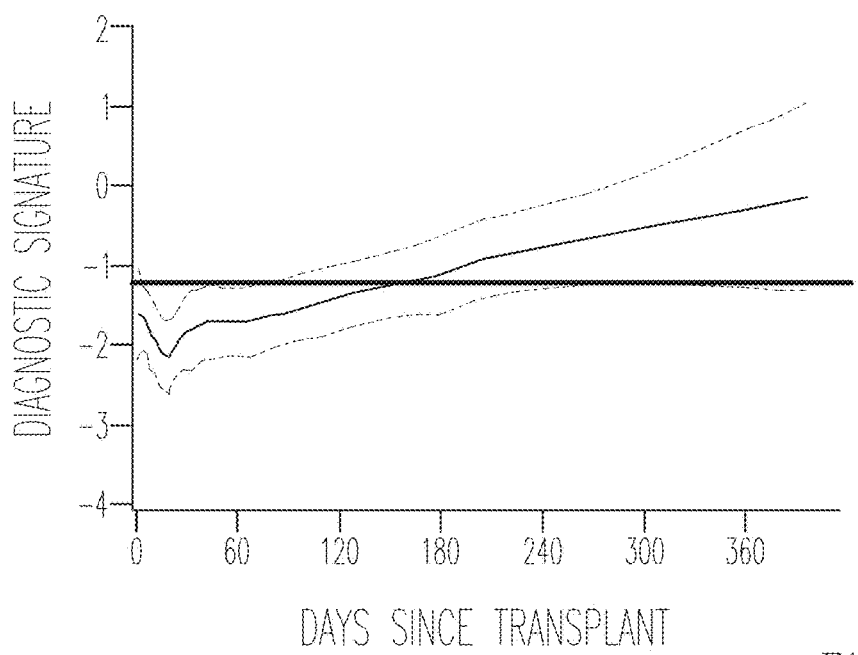
FIG. 5A-5D illustrate the average within-person prospective trajectory of the diagnostic signature. Sequential urine specimens were collected from study participants as per the CTOT-04 study protocol on post-transplant days 3, 7, 15 and 30 and months 2, 3, 4, 5, 6, 9 and 12. The average within-person trajectories and 95% confidence bands of the diagnostic signature for the ACR group (n=195 QC-passed urine samples obtained prior to 3 days before the first ACR biopsy from 38 patients who had no abnormal biopsy prior to their first ACR biopsy) (FIG. 5A), No Rejection Biopsy group (n=960 QC-passed urine samples from 132 patients for whom all biopsies were rejection free) (FIG. 5B), Stable (no biopsy) group (n=1491 QC-passed urine samples from 201 patients) (FIG. 5C). In all panels, the central lines of the loess curves indicate the trajectory, the associated dashed lines show the 95% confidence interval, and the straight lines at about -1.2 shown the diagnostic threshold. On average, the diagnostic signature in the No Rejection Biopsy group and in the Stable (no biopsy) group remained well below the -1.213 threshold diagnostic for ACR throughout the first 400 days post-transplant whereas a progressive increase in the signature was seen in the urine samples of those who went on to develop ACR. By about 80 days post-transplant there was a clear signal that the future ACR patients have elevated values (the lower bound of the 95% confidence band for this group exceeds the upper bound of the 95% confidence bands for the two other groups), and beyond about 160 days the average value for the future ACR patients is greater than or equal to the threshold diagnostic for ACR (FIG. 5D). The y-axis values are diagnostic-signature scores without intrinsic units of measurement; they were calculated from the logistic-regression equation (-6.1487+0.8534 $\log_{10}$[CD3ε/18S]+0.6376 $\log_{10}$[IP-10/
Figure 5B:
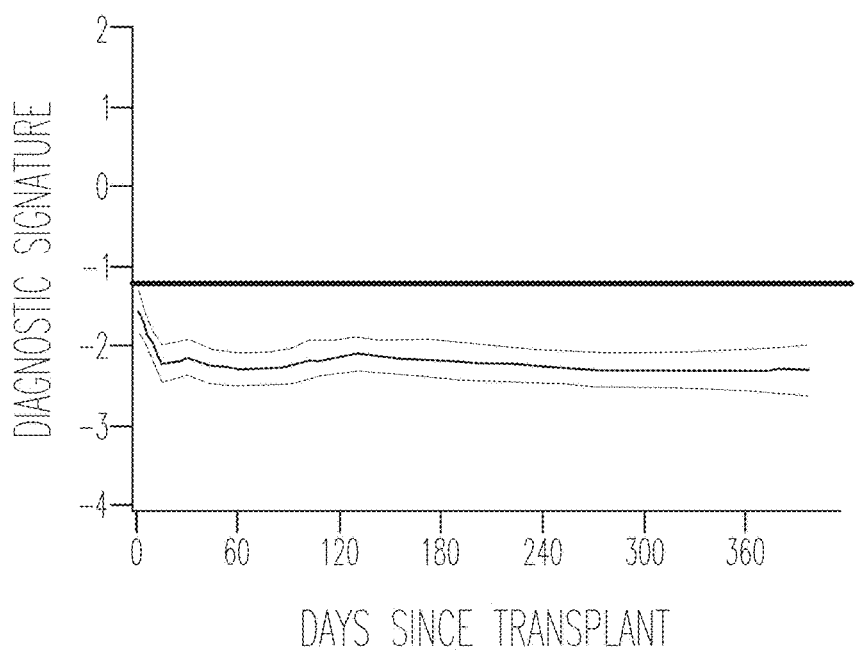
Figure 5C:
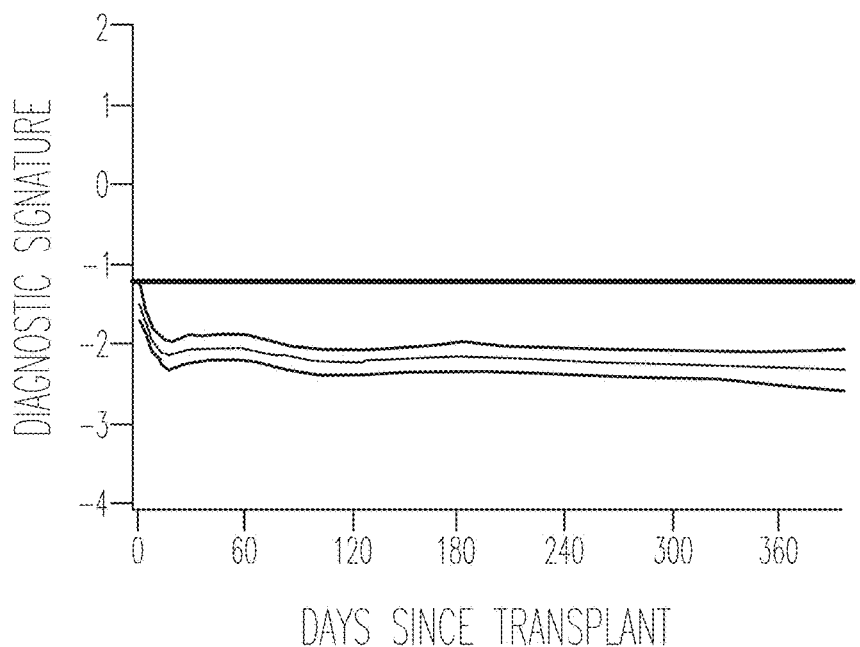
Figure 5D:
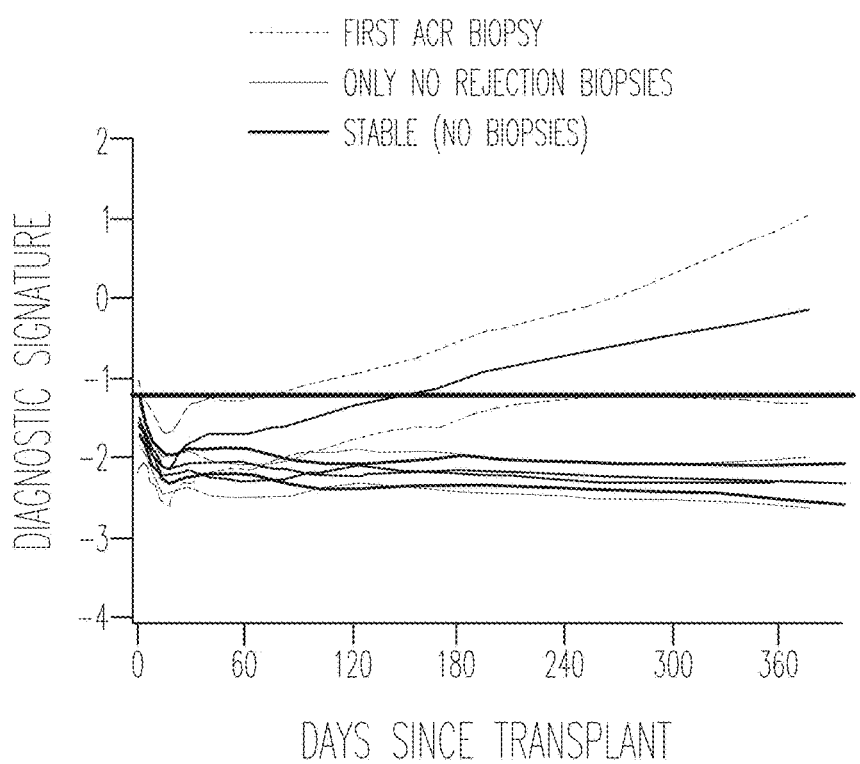

Prospective Trajectory of the Diagnostic Signature as a Function of Time Since Transplant FIG. 5 displays the loess-smoothed average within-person trajectories and 95% confidence bands of the diagnostic signature for the acute cellular rejection group (FIG. 5A), No Rejection Biopsy group (FIG. 5B), and the Stable (no biopsy) group (FIG. 5C). The trajectories in the No Rejection Biopsy group and in the Stable (no biopsy) group were flat and remained below the −1.213 threshold diagnostic for acute cellular rejection throughout the first 400 days post-transplant whereas a progressive increase in the diagnostic signature was seen in urine samples from patients in whom acute cellular rejection developed. Thus, even after the exclusion of all urine samples obtained after the development of acute cellular rejection and those that were matched to biopsy specimens showing acute cellular rejection and had been used to develop the diagnostic signature, there was a clear signal by approximately 80 days after transplantation that the diagnostic signature scores were elevated in whom acute cellular rejection subsequently developed. After approximately 160 days, the average score for the patients in whom acute cellular rejection developed was greater than or equal to the threshold level that was diagnostic for acute cellular rejection (FIG. 5D).

Immunosuppressive Therapy and the Diagnostic Signature.

The CTOT-04 study was an observational study that did not dictate post-transplant immunosuppressive therapy, with each site using their ongoing clinical protocol. Among the 485 kidney transplant recipients profiled, 77.1% received T cell depleting antibodies (CAMPATH-1H [26.2%, n=127] and Thymoglobulin [50.9%, n=247]), 11.1% (n=54) received interleukin-2 receptor monoclonal antibody (Basiliximab), 4.3% (n=21) received more than one type of induction therapy, 0.8% (n=4) received no induction therapy, and for 6.6% (n=32) no information was available (Table 1).

Impact of Induction Therapy on the Diagnostic Signature.

The type of induction therapy (T cell depleting vs. non-depleting) had a significant impact on the score and trajectory of the diagnostic signature. FIGS. 6A-6C show LOESS curves (mean and 95% confidence intervals [shaded area]) portraying how the diagnostic signature during days 5-180 post-transplant varies among those who received T cell depleting antibodies (Thymoglobulin/CAMPATH-1H) or non-depleting anti-IL-2 receptor antibodies (Basiliximab). The within-person trajectories shown include only those patients in the Stable (no biopsy) group and the Only No Rejection Biopsy group.

FIG. 6A shows that the diagnostic signature score of those who received Thymoglobulin/CAMPATH-1H is flat during the first 6 months of transplantation. FIG. 6B shows that those who received anti-IL-2 receptor antibodies exhibited a substantially elevated diagnostic signature early on, decreasing rapidly during the first 30 days, and then more gradually through the next two months post-transplant. FIG. 6C shows both trajectories to highlight the difference in trajectories, especially during the first month post-transplant, based on whether patients received T cell depleting or non-depleting induction therapy. The difference between the 29 patients who received Basiliximab and the 265 patients who received either Thymoglobulin or CAMPATH-1H is substantive and significant ($\chi^2=16.44$, df=3, p=0.0009).

Type of Induction Therapy and Accuracy of the Diagnostic Signature.

With respect to whether the signature is diagnostic of acute cellular rejections irrespective of the type of induction therapy, two different strategies were used to examine whether the relationship of the diagnostic signature to biopsy group (acute cellular rejection vs. No Rejection Biopsy) differed for T cell depleting vs. non-depleting induction therapies. First, separate ROC curves were created for those who received basiliximab and those who received Thymoglobulin/Campath-1H. The AUCs were 0.72 (95% CI: 0.50 to 0.94, p=0.05) and 0.87 (95% CI: 0.64 to 1.00, p=0.002), respectively, and not significantly different. Second, a logistic regression was performed predicting acute cellular rejection diagnosis from the diagnostic signature, induction therapy, and the interaction of the two; if the relationship of the diagnostic signature to diagnosis differed by induction therapy, the interaction term would be expected to be statistically significant; it was not (P=0.11). These two different statistical approaches demonstrate that the signature is diagnostic of acute cellular rejection in those induced either with T cell depleting antibodies or with IL-2 receptor antibodies.

Induction Vs. No Induction.

In CTOT-04, almost all patients received induction therapy and only 4 of 485 patients were managed with no induction therapy. The very small number of patients managed without induction therapy did not allow a meaningful comparison of Any Induction vs. No Induction groups.

Maintenance Immunosuppressive Therapy.

Calcineurin inhibitors (CNI) were the mainstay of post-transplant immunosuppressive therapy at all 5 sites and 5305 of 5749 maintenance therapy records (92.28%) were CNI entries with 5107 of 5305 entries for tacrolimus and the remaining 208 for cyclosporine as the CNI. For patients in the Stable (no biopsy) group or the Only No Rejection biopsy group, the diagnostic signature score was significantly lower (−0.37 points, P=0.04) at visits when patients had been on a CNI maintenance regimen compared to no-CNI maintenance regimen after controlling for other maintenance drugs such as mycophenolic acid (MPA) and steroids. This pattern was not observed in the small acute cellular rejection biopsy group (N=38, P=0.75).

MPA maintenance regimen vs. no-MPA maintenance regimen, after controlling for other maintenance drugs such as CNI and steroids did not significantly impact the diagnostic signature in either the No Rejection biopsy plus Stable (no biopsy) patients (P=0.72) or in the acute cellular rejection biopsy group (P=0.31).

Steroid maintenance regimen vs. no-steroid maintenance regimen, after controlling for other maintenance drugs such as CNI and MPA, did not have a significant impact in the No Rejection biopsy group plus the Stable (no biopsy) patients (P=0.14). The diagnostic signature score however was significantly higher for those on steroid maintenance in the acute cellular rejection biopsy group (P=0.03).

Anti-Rejection Therapy and the Diagnostic Signature.

Of the 43 acute cellular rejection biopsies with paired urine samples, 32 had QC-passed urine samples 14±7 days post-acute cellular rejection biopsy. A comparison of the diagnostic signature values showed a significant decrease from −0.37 at the time of acute cellular rejection biopsy to −0.86 at 14±7 days post biopsy (P=0.05). The decrease in the value for the diagnostic signature was further compared to whether the patient was a responder, defined as the follow-up estimated glomerular filtration rate (eGFR) being no higher than it was at the time of the acute cellular rejection biopsy, or a non-responder to the initial anti-rejection therapy. Estimated glomerular filtration rate data were available at the time of biopsy and at the follow up time for 25 of the 32 samples, and among these 25 samples, 21 were from responders and the remaining 4 were from non-responders based on the above criterion. In the 21 responders, the value for the diagnostic signature decreased significantly from the baseline value of −0.43 to −1.08 at 14±7 days post biopsy (P=0.05); in the small number of non-responders, the decrease in the value from +0.12 to −0.80 was even greater than in the responders (0.92 vs. 0.65), but was not statistically significant (P=0.20). Of note, the non-responders had higher levels of the diagnostic signature at the time of biopsy and two weeks later. Furthermore, even among the clinical responders, 7 of 21 did not show a numerical decrease in the value of the diagnostic signature.

Infections and the Diagnostic Signature.

Eighty four kidney graft recipients had 128 infections that could be classified into 2 broad categories—(i) urinary tract infection (UTI) independent of the type of organism involved; (ii) blood infections independent of the type of organism or organ involved. The patients had two types of blood infections: (i) CMV; and (ii) BKV. There was some overlap in these categories (e.g., both UTI and septicemia). Nineteen of these 84 patients with infections also experienced an episode of acute cellular rejection.

The impact of infections on urinary cell mRNA profiles was first examined independent of the impact of acute cellular rejection by conducting analyses restricted to the 65 patients who had infections but did not experience an episode of acute cellular rejection. A total of 491 QC-passed urine samples were available from the 65 non-acute cellular rejection patients for calculating the diagnostic score and data analysis. Among the 491 samples, 434 samples were from the same 65 patients when they did not have infections, 32 samples from those with an on-going UTI, 37 samples from those with an on-going blood infection, 14 samples from those with on-going BKV and 12 samples from those with on-going CMV.

The mean diagnostic score in the 65 patients when they had no recorded infection was −2.14 (95% CI: −2.38 to −1.90, n=434 samples). The mean at the time of BKV infection was −1.23 (95% CI: −2.01 to −0.45; 14 samples). The mean was −2.39 (95% CI: −3.22 to −1.56; 12 samples) at the time of CMV infection. The mean was −2.03 (95% CI: −2.55 to −1.51; 32 samples) at the time of a UTI. And, the mean was −1.95 (95% CI: −2.47 to −1.43; 37 samples) at the time of a blood infection. In a multilevel linear model evaluating the independent effect of each type of infection, statistically controlling for the effects of the other three types of infection, BKV infection was associated with the diagnostic signature (P=0.03) but UTI (P=0.69), blood infection (P=0.94) and CMV (P=0.56) were not. Because BKV infection alone was associated with the signature, the presence or absence of BKV infection was examined irrespective of the presence or absence of other infections in a second multilevel linear model, and the results showed that the presence of infection increased the diagnostic signature score by 0.93 (95% CI: 0.16 to 1.69) (P=0.02).

A total of 149 QC-passed urine samples were available from the 19 patients who experienced an acute cellular rejection as well as infections. Among the 149 samples, 20 samples were from the patients with an on-going infection, and among these, 17 samples were from those with an on-going blood infection, 7 from those with on-going BKV, 4 from those with an on-going urinary tract infection, and 2 from those with on-going CMV infection (the number of samples exceeds 20 since some had more than one type of infection, e.g., blood and urinary tract infections). Among the 19 patients with infections and acute cellular rejection, 4 urine samples from 4 patients were obtained at the time of an acute cellular rejection biopsy and the diagnostic signature scores for these 4 samples were: 0.712, 0.901, −0.210 and −1.206. Thus, in every instance the diagnostic signature score was above the diagnostic threshold for acute cellular rejection diagnosis, suggesting that the presence of infection at the time of an acute cellular rejection does not result in a false negative diagnosis of acute cellular rejection.

There was no standardized monitoring for EBV in CTOT-04.

Diagnostic Signature and Future Graft Function.

Also investigated was whether the mean diagnostic score at 4-6 months is predictive of a 30% or greater decline in renal allograft function from 6 to 12 months. The 4-6 month time points were chosen because immunosuppressive therapy is more or less in a steady state by 3-months post transplantation. Analysis of the diagnostic score at 4-6 months after transplantation showed that the score is associated with an elevated risk of a ≥30 percent decrease in estimated glomerular filtration rate from 6 to 12 months (Odds Ratio=2.66, 95% CI=1.45 to 4.87, P=0.002).

The average within-person trajectories of all three groups (acute cellular rejection biopsy group, No rejection biopsy group, Stable [no biopsy] group) decreased from post-transplant day 3 to day 7 and subsequently either remained flat (No rejection biopsy group and Stable [no biopsy] group) or increased (acute cellular rejection biopsy group) (FIG. 5). A multilevel linear model was used to evaluate whether there were reliable individual differences in the slope of the diagnostic signature trajectory across days 7, 15 and 30 and found that with 3 or fewer values of the diagnostic signature obtained so close in time, there were no reliable individual differences in patients' slopes. More specifically, the estimated variability of the slopes in a latent growth curve model was zero.

Also analyzed, was whether the mean of the diagnostic signature averaged across days 7, 15 and 30 predicted future acute cellular rejection, after excluding those who experienced an acute cellular rejection within the first two months post-transplantation. Note that 31 patients had a first acute cellular rejection 2 months post-transplant or later. The early diagnostic signature did not differentiate the acute cellular rejection group from those 121 patients for whom all their biopsies showed no evidence of rejection (OR=1.08 per 1-point increase in the mean diagnostic signature, 95% CI: 0.55 to 2.15, P=0.82). When the Stable (no biopsy) patients were added to the comparison group, the results were similar (OR=1.15 per 1-point increase in the mean diagnostic signature, 95% CI: 0.60 to 2.19, P=0.67).

REFERENCES

Each of the following references is specifically incorporated herein by reference in its entirety.

1. Hariharan S, Johnson C P, Bresnahan B A, Taranto S E, McIntosh M J, Stablein D. Improved graft survival after renal transplantation in the United States, 1988 to 1996. N Engl J Med 2000; 342:605-12.
2. Pallardo Mateu L M, Sancho Calabuig A, Capdevila Plaza L, Franco Esteve A. Acute rejection and late renal transplant failure: risk factors and prognosis. Nephrol Dial Transplant 2004; 19 Suppl 3:iii38-42.
3. Tonelli M, Wiebe N, Knoll G, et al. Systematic review: kidney transplantation compared with dialysis in clinically relevant outcomes. Am J Transplant 2011; 11:2093-109.
4. Langone A J, Chuang P. The management of the failed renal allograft: an enigma with potential consequences. Semin Dial 2005; 18:185-7.
5. Williams W W, Taheri D, Tolkoff-Rubin N, Colvin R B. Clinical role of the renal transplant biopsy. Nat Rev Nephrol 2012; 8:110-21.

6. Furness P N, Taub N. International variation in the interpretation of renal transplant biopsies: report of the CERTPAP Project. Kidney Int 2001; 60:1998-2012.
7. Li B, Hartono C, Ding R, et al. Noninvasive diagnosis of renal-allograft rejection by measurement of messenger RNA for perforin and granzyme B in urine. N Engl J Med 2001; 344:947-54.
8. Kong J, Yamagi K, Muthukumar T, Ding R, Dadhania D, Sharma V. K, Hartono C, Serur D, Seshan S, Li B, Suthanthiran M. An mRNA profile that includes measurement of transcripts for CD3, perforin and granzyme B in urinary cells accurately distinguishes acute rejection from other causes of renal allograft dysfunction. J AM Soc Nephrol 2001; 12: A4885.
9. Ding R, Li B, Muthukumar T, et al. CD103 mRNA levels in urinary cells predict acute rejection of renal allografts. Transplantation 2003; 75:1307-12.
10. Muthukumar T, Ding R, Dadhania D, et al. Serine proteinase inhibitor-9, an endogenous blocker of granzyme B/perforin lytic pathway, is hyperexpressed during acute rejection of renal allografts. Transplantation 2003; 75:1565-70.
11. Tatapudi R R, Muthukumar T, Dadhania D, et al. Noninvasive detection of renal allograft inflammation by measurements of mRNA for IP-10 and CXCR3 in urine. Kidney Int 2004; 65:2390-7.
12. Muthukumar T, Dadhania D, Ding R, et al. Messenger RNA for FOXP3 in the urine of renal-allograft recipients. N Engl J Med 2005; 353:2342-51.
13. Racusen L C, Colvin R B, Solez K, et al. Antibody-mediated rejection criteria—an addition to the Banff 97 classification of renal allograft rejection. Am J Transplant 2003; 3:708-14.
14. Steyerberg E W, Vickers A J, Cook N R, et al. Assessing the performance of prediction models: a framework for traditional and novel measures. Epidemiology 2010; 21:128-38.
15. Efron B, Tibshirani R. An introduction to the bootstrap. New York: Chapman and Hall; 1993.
16. Harrell F E, Jr., Lee K L, Mark D B. Multivariable prognostic models: issues in developing models, evaluating assumptions and adequacy, and measuring and reducing errors. Stat Med 1996; 15:361-87.
17. Austin P, Tu J. Bootstrap methods for developing predictive models. The American Statistician 2004; 58:131-7.
18. Cox D R. Two further applications of a model for binary regression. Biometrika 1958; 45:562-5.
19. Miller M E, Langefeld C D, Tierney W M, Hui S L, McDonald C J. Validation of probabilistic predictions. Med Decis Making 1993; 13:49-58.
20. Le C T. A solution for the most basic optimization problem associated with an ROC curve. Statistical Methods in Medical Research 2006; 15:571-84.
21. Tripepi G, Jager K J, Dekker F W, Zoccali C. Statistical methods for the assessment of prognostic biomarkers (part II): calibration and re-classification. Nephrol Dial Transplant 2010; 25:1402-5.
22. Strom T B, Tilney N L, Carpenter C B, Busch G J. Identity and cytotoxic capacity of cells infiltrating renal allografts. New England Journal of Medicine 1975; 292: 1257-63.
23. Schenk A D, Rosenblum J M, Fairchild R L. Chemokine-directed strategies to attenuate allograft rejection. Clinics in Laboratory Medicine 2008; 28:441-54, vii.
24. Schmittgen T D, Livak K J. Analyzing real-time PCR data by the comparative C(T) method. Nat Protoc 2008; 3:1101-8.
25. Lodish H F. Translational control of protein synthesis. Annual Review of Biochemistry 1976; 45:39-72.
26. Almond P S, Matas A, Gillingham K, et al. Risk factors for chronic rejection in renal allograft recipients. Transplantation 1993; 55:752-6; discussion 6-7.
27. Humar A, Payne W D, Sutherland D E, Matas A J. Clinical determinants of multiple acute rejection episodes in kidney transplant recipients. Transplantation 2000; 69:2357-60.
28. Cook N R. Use and misuse of the receiver operating characteristic curve in risk prediction. Circulation 2007; 115:928-35.
29. Ding R, Medeiros M, Dadhania D, et al. *Noninvasive diagnosis of BK virus nephritis by measurement of messenger RNA for BK virus VP1 in urine.* Transplantation 2002; 74:987-94.
30. Steyerberg E. Clinical prediction models: A practical approach to development, validation and updating. New York: Springer; 2009.
31. Zhang L, Zhou W, Velculescu V E, et al. Gene expression profiles in normal and cancer cells. Science 1997; 276: 1268-72.
32. Roge R, Thorsen J, Torring C, Ozbay A, Moller B K, Carstens J. Commonly used reference genes are actively regulated in in vitro stimulated lymphocytes. Scand J Immunol 2007; 65:202-9.
33. Bustin S A, Benes V, Garson J A, et al. The MIQE guidelines: minimum information for publication of quantitative real-time PCR experiments. Clin Chem 2009; 55:611-22.
34. Brennan D C, Daller J A, Lake K D, Cibrik D, Del Castillo D. Rabbit antithymocyte globulin versus basiliximab in renal transplantation. N Engl J Med 2006; 355: 1967-77.
35. Hanaway M J, Woodle E S, Mulgaonkar S, et al. Alemtuzumab induction in renal transplantation. N Engl J Med 2011; 364:1909-19.
36. Gaber L W, Moore L W, Gaber A O, Tesi R J, Meyer J, Schroeder T J. Correlation of histology to clinical rejection reversal: a thymoglobulin multicenter trial report. Kidney Int 1999; 55:2415-22.
37. Dadhania D, Snopkowski C, Ding R, Muthukumar T, Lee J, Bang H, Sharma V K, Seshan S, August P, Kapur S, Suthanthiran M. Validation of noninvasive diagnosis of BK virus nephropathy and identification of prognostic biomarkers. Transplantation. 2010; 90:189-97.
38. WO 2011/112719 A1 by Mankkkam et al., which is specifically incorporated herein by reference in its entirety.
27. Anglicheau D, Suthanthiran M. Noninvasive prediction of organ graft rejection and outcome using gene expression patterns. Transplantation 2008; 86: 192-9.

The contents of all cited references (including literature references, issued patents, and published patent applications as cited throughout this application) are hereby expressly incorporated by reference in their entireties.

The specific methods, compositions, and devices described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which are not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acids or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements of the invention are intended to describe and summarize features of the methods, devices, and compositions according to the foregoing description in the specification.

Statements:

1. A method for detecting developing or existing dysfunction or rejection of a kidney transplant in a subject comprising: determining whether CD3ϵ mRNA, IP-10 mRNA, and 18S rRNA are expressed at higher levels in cells of a urine sample obtained from the subject than a baseline, control or reference level of urinary cell expression of CD3ϵ mRNA, IP-10 mRNA, and 18S rRNA, to thereby detect developing or existing dysfunction or rejection of the kidney transplant in the subject.

2. The method of statement 1, wherein one or more CD3ϵ mRNA, IP-10 mRNA, and 18S rRNA expression level is at least 5%, 10%, 15%, 20%, 25%, 30%, 35%, 40%, 45%, 50%, 55%, 60%, 65%, 70%, 75%, 80%, 85%, 90%, 95%, or 100% higher in the cells of the urine sample obtained from the subject than in the baseline, control or reference level of urinary cell expression of CD3ϵ mRNA, IP-10 mRNA, and 18S rRNA.

3. The method of statement 1 or 2, wherein the baseline, control or reference level of urinary cell expression of CD3ϵ mRNA, IP-10 mRNA, or 18S rRNA is the respective amount of urinary cell expression of CD3ϵ mRNA, IP-10 mRNA, or 18S rRNA expressed by one or more healthy persons or one or more persons with a well-functioning (e.g., stable) transplanted organ.

4. The method of any of statements 1-3, wherein the baseline, control or reference level of urinary cell expression of CD3ϵ mRNA, IP-10 mRNA, and 18S rRNA is the respective amount of urinary cell expression of CD3ϵ mRNA, IP-10 mRNA, and 18S rRNA expressed by a population of healthy persons or a population of persons with a well-functioning (e.g., stable) transplanted organ.

5. The method of any of statements 1-4, comprising isolating and/or purifying RNA from the urine sample obtained from the subject.

6. The method of any of statements 1-5, comprising hybridizing at least one probe or primer to RNA from the urine sample obtained from the subject.

7. The method of any of statements 1-6, comprising hybridizing at least two probes or primers to RNA from the urine sample obtained from the subject.

8. The method of any of statements 1-7, comprising hybridizing at least three probes or primers to RNA from the urine sample obtained from the subject.

9. The method of any of statements 1-8, comprising hybridizing at least one probe or primer to RNA from the urine sample obtained from the subject, wherein the probe or primer can hybridize to a CD3ϵ mRNA, IP-10 mRNA, or 18S rRNA.

10. The method of any of statements 1-9, comprising hybridizing at least one probe or primer to RNA from the urine sample obtained from the subject, wherein the probe or primer can hybridize under stringent conditions to a CD3ϵ mRNA, IP-10 mRNA, or 18S rRNA.

11. The method of statement 10, wherein the stringent conditions comprise one or more washes in 0.2×SSC, 0.1% SDS at 60° C.

12. The method of any of statements 1-11, comprising hybridizing one or more probes or primers that can hybridize to an RNA with a sequence that has at least 70%, or at least 80%, or at least 90%, or at least 95%, or at least 96%, or at least 97%, or at least 98%, or at least 99% sequence identity or complementarity to SEQ ID NO:1 (18S rRNA).

13. The method of any of statements 1-12, comprising hybridizing one or more probes or primers that can hybridize to an RNA with a sequence that has at least 70%, or at least 80%, or at least 90%, or at least 95%, or at least 96%, or at least 97%, or at least 98%, or at least 99% sequence identity or complementarity to SEQ ID NO:2 (CD3ϵ mRNA).

14. The method of any of statements 1-12, comprising hybridizing one or more probes or primers that can hybridize to an RNA with a sequence that has at least 70%, or at least 80%, or at least 90%, or at least 95%, or at least 96%, or at least 97%, or at least 98%, or at least 99% sequence identity or complementarity to SEQ ID NO:3 (IP-10 mRNA).

15. The method of any of statements 1-14, comprising hybridizing one or more probe or primer to RNA from the urine sample obtained from the subject, wherein the one or more probe or primer has a sequence that is selected from the group consisting of SEQ ID NO:28, 29, 30, or any combination thereof (18S rRNA).

16. The method of any of statements 1-15, comprising hybridizing one or more probe or primer to RNA from the urine sample obtained from the subject, wherein the one or more probe or primer has a sequence that is selected from the group consisting of SEQ ID NO:4, 5, 6, or any combination thereof (CD38).

17. The method of any of statements 1-16, comprising hybridizing one or more probe or primer to RNA from the urine sample obtained from the subject, wherein the one or more probe or primer has a sequence that is selected from the group consisting of SEQ ID NO:13, 14, 15, or any combination thereof (IP-10).

18. The method of any of statements, 6-17, wherein the at least one probe or primer is labeled with a detectable label.

19. The method of any of statements 1-18, comprising normalizing the amount (or copy number) of CD3ε mRNA against the amount (or copy number) of a housekeeping gene.

20. The method of any of statements 1-19, comprising normalizing the amount (or copy number) of IP-10 mRNA against the amount (or copy number) of a housekeeping gene.

21. The method of statement 19 or 20, wherein the housekeeping gene is 2-Microglobulin (β2M), Glucose-6-phosphate dehydrogenase (G6PDH), 5-aminolevulinate synthase (ALAS or ALAS 1) Hypoxanthinephosphoribosyltransferase (HPRT), Porphobilinogen deaminase (PBGD), or 18S rRNA.

22. The method of any of statements 19-21, wherein the housekeeping gene is 18S rRNA.

23. The method of any of statements 19-22, wherein normalizing the amount of CD3ε mRNA comprises dividing a determined absolute urinary CD3ε mRNA copy number per microgram of total RNA from a sample by a determined absolute urinary 18S rRNA copy number per microgram of total RNA times $10^{-6}$ from the same sample:

Sample's normalized $CD3\varepsilon$ mRNA amount =

$$\frac{\text{determined absolute } CD3\varepsilon \text{ mRNA copy number/}\mu\text{g total } RNA}{\text{determined absolute } 18S \text{ } rRNA \text{ copy number/}\mu\text{g total } RNA \times 10^{-6}}.$$

24. The method of any of statements 19-23, wherein normalizing the amount of IP-10 mRNA comprises dividing a determined absolute urinary IP-10 mRNA copy number per microgram of total RNA from a sample by a determined absolute urinary 18S rRNA copy number per microgram of total RNA times $10^{-6}$ from the same sample:
Sample's normalized IP-10 mRNA amount=
determined absolute IP-10 mRNA copy number/μg total RNA
determined absolute 18S rRNA copy number/μg total RNA×$10^{-6}$.

25. The method of any of statements 1-24, comprising ascertaining a diagnostic signature of developing or existing dysfunction or rejection of a kidney transplant in the subject with the following algorithm:

signature=−6.1487+0.8534 $\log_{10}(CD3\varepsilon/18S)$+0.6376 $\log_{10}(IP\text{-}10/18S)$+1.6464 $\log_{10}(18S)$ where:
 CD3ε refers to an absolute urinary CD3ε mRNA copy number per microgram of total RNA;
 IP-10 refers to an absolute urinary IP-10 mRNA copy number per microgram of total RNA;
 18S refers to an absolute urinary 18S rRNA copy number per microgram of total RNA times $10^{-6}$.

26. The method of statement 25, wherein the subject has an existing dysfunction or rejection of a kidney transplant when the signature is greater than −1.21.

27. The method of statement 25 or 26, wherein the subject has an existing dysfunction or rejection of a kidney transplant when the signature is greater than −1.213.

28. The method of statement 25, wherein the subject will develop dysfunction or rejection of a kidney transplant when the signature is greater than −1.21.

29. The method of statement 25 or 28, wherein the subject will develop dysfunction or rejection of a kidney transplant when the signature is greater than −1.213.

30. The method of any of statements 1-29, comprising monitoring a subject over time for developing or existing dysfunction or rejection of a kidney transplant in a subject.

31. The method of any of statements 1-30, comprising monitoring a subject over time for developing or existing dysfunction or rejection of a kidney transplant in a subject by collecting urine samples from the subject and performing the method with those urine samples.

32. The method of any of statements 1-31, comprising monitoring a subject over time and informing the subject if there is continuing rise in the diagnostic signature over time.

33. The method of any of statements 1-32, comprising informing the subject of a developing or existing dysfunction or rejection of a kidney transplant in the subject.

34. The method of any of statements 1-33, comprising informing the subject of a developing or existing dysfunction or rejection of a kidney transplant in the subject, when the CD3ε mRNA, IP-10 mRNA, and 18S rRNA are expressed at higher levels in cells of a urine sample obtained from the subject than a baseline, control or reference level of urinary cell expression of CD3ε mRNA, IP-10 mRNA, and 18S rRNA.

35. The method of any of statements 25-34, comprising informing the subject when the signature is greater than −1.21 of a developing or existing dysfunction or rejection of a kidney transplant in the subject.

36. The method of any of statements 25-35, comprising informing the subject when the signature is greater than −1.213 of a developing or existing dysfunction or rejection of a kidney transplant in the subject.

37. The method of any of statements 1-36, comprising treating a developing or existing dysfunction or rejection of a kidney transplant in the subject.

38. The method of any of statements 1-37, comprising treating a developing or existing dysfunction or rejection of a kidney transplant in the subject when the CD3ε mRNA, IP-10 mRNA, and 18S rRNA are expressed at higher levels in cells of a urine sample obtained from the subject than a baseline, control or reference level of urinary cell expression of CD3ε mRNA, IP-10 mRNA, and 18S rRNA.
39. The method of any of statements 25-38, comprising treating a developing or existing dysfunction or rejection of a kidney transplant in the subject when the signature is greater than −1.21.
40. The method of any of statements 25-39, comprising treating a developing or existing dysfunction or rejection of a kidney transplant in the subject when the signature is greater than −1.213.
41. The method of any of statements 36-40, wherein treating comprises plasmapheresis, administration of an anti-rejection agent, increasing a dosage of an anti-rejection agent that the subject is receiving or any combination thereof.
42. The method of statement 41, wherein the anti-rejection agent is azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD 154, anti-CD3 antibody, thymoglobin, OKT3, corticosteroid, or a combination thereof.
43. A composition comprising one or more probes or primers for each of CD3ε mRNA, IP-10 mRNA, and 18S rRNA.
44. The composition of statement 43, further comprising nucleotide triphosphates selected from the group consisting of ATP, CTP, GTP, UTP, TTP, or any combination thereof.
45. The composition of statement 43 or 44, further comprising a reverse transcriptase, DNA polymerase, or a combination thereof.
46. The composition of statement 45, wherein the DNA polymerase is heat stable.
47. The composition of statement 45 or 46, wherein the DNA polymerase has 5' to 3' exonuclease activity.
48. A device comprising one or more probes or primers for each of CD3ε mRNA, IP-10 mRNA, and 18S rRNA, covalently linked to a solid support.
49. A device consisting essentially of one or more probes or primers for each of CD3ε mRNA, IP-10 mRNA, and 18S rRNA, covalently linked to a solid support.
50. The device of statement 48 or 49, further comprising a control probe or primer.
51. The device of statement 50, wherein the control probe or primer does not hybridize to a CD3ε mRNA, IP-10 mRNA, or 18S rRNA.
52. The device of statement 50 or 51, wherein the control probe or primer can hybridize to an RNA that is not informative about transplant rejection.
53. A kit comprising one or more probes or primers for each of CD3ε mRNA, IP-10 mRNA, and 18S rRNA, and instructions for use in detecting developing or existing dysfunction or rejection of a kidney transplant in a subject.
54. The kit of statement 53 further comprising one or more of any of the following: urine collection components, RNA isolation components, RNA storage components, buffers, nucleotide triphosphates, DNA polymerases, reverse transcriptases, labels, label detectors, recording devices, or any combination thereof.
55. A diagnostic signature defined as:

signature=−6.1487+0.8534 log$_{10}$(CD3ε/18S)+0.6376 log$_{10}$(IP-10/18S)+1.6464 log$_{10}$(18S)

which relates the 18S-normalized CD3ε mRNA [i.e. log$_{10}$(CD3ε/18S)], the 18S-normalized IP-10 mRNA [i.e. log$_{10}$(IP-10/18S)], and 18S rRNA [i.e. log$_{10}$(18S)], (all logged) obtained from the urine of humans with kidney allografts to kidney allograft status (CD3 and IP-10: Absolute mRNA copy number in one microgram of total RNA; 18S rRNA: Absolute 18S ribosomal RNA copy number×10$^{-6}$ in microgram of total RNA).
56. A method to diagnose acute cellular rejection in kidney allografts, as indicated by a value of the diagnostic signature of statement 55 greater than −1.21.
57. A method to predict the likelihood of the occurrence of acute cellular rejection of a kidney allograft in a human by detecting a continuing rise in the diagnostic signature of statement 55 over time.
58. A method to monitor the efficacy of immunosuppressive therapy of a human with a kidney allograft by monitoring the diagnostic signature of statement 55 wherein an increase in the value of this diagnostic signature over time is indicative of reduced efficacy, and a reduction in the value of this diagnostic signature over time is indicative of increased efficacy.
59. A method to treat humans with a kidney allograft by monitoring the value of the diagnostic signature of statement 55, wherein an increase in the treatment regimen is required if the value of this diagnostic signature increases over time.
60. A method to diagnose acute cellular rejection in kidney allografts, comprising:
(a) obtaining cells from urine of a subject with a kidney allograft;
(b) quantifying expression of CD3ε mRNA, IP-10, mRNA, and 18S rRNA in the cells from the urine, to obtain quantified CD3ε, IP-10 and 18S RNA levels;
(c) converting the quantified CD3ε, IP-10 and 18S RNA levels into a diagnostic signature defined as:

signature=−6.1487+0.8534 log$_{10}$(CD3ε/18S)+0.6376 log$_{10}$(IP-10/18S)+1.6464 log$_{10}$(18S)

which relates the 18S-normalized CD3ε mRNA [i.e. log$_{10}$(CD38/18S)], the 18S-normalized IP-10 mRNA [i.e. log$_{10}$(IP-10/18S)], and 18S rRNA [i.e. log$_{10}$(18S)], (all logged) obtained from cells in the urine of the subject with the kidney allograft to kidney allograft status (CD3 and IP-10: Absolute mRNA copy number in one microgram of total RNA; 18S rRNA: Absolute 18S ribosomal RNA copy number×10$^{-6}$ in microgram of total RNA).
61. The method of statement 60, comprising monitoring the subject's diagnostic signature over time by repeating each of steps (a), (b) and (c) at least one more time.
62. The method of statement 60 or 61, comprising monitoring the subject's diagnostic signature over time by repeating each of steps (a), (b) and (c) daily, twice weekly, weekly, bi-weekly, twice monthly, monthly, twice yearly, yearly, or a combination thereof.
63. The method of any of statements 60-62, comprising diagnosing acute cellular rejection of the kidney allograft when the subject's diagnostic signature increases compared to a previously obtained diagnostic signature for the subject.
64. The method of any of statements 60-63, further comprising treating the subject for acute cellular rejection of the kidney allograft.

The Abstract is provided to allow the reader to quickly ascertain the nature and gist of the technical disclosure. The Abstract is submitted with the understanding that it will not be used to interpret or limit the scope or meaning of the claims.

What is claimed:

1. A method comprising treating a developing or existing dysfunction or rejection of a kidney transplant in a subject when a urinary RNA sample has a diagnostic signature greater than −1.21, and the signature is determined by a method comprising:
   (a) determining an absolute urinary CD3ε mRNA, IP-10 mRNA, and 18S rRNA copy numbers per microgram of total RNA in the urine RNA sample using at least one probe or primer with a SEQ ID NO: 4, 5, 6, 13, 14, 15, 28, 29, or 30 sequence; and
   (b) ascertaining a diagnostic signature of developing or existing dysfunction or rejection of a kidney transplant in the subject with the following algorithm:

$$\text{signature}=-6.1487+0.8534 \log_{10}(CD3\varepsilon/18S)+0.6376 \log_{10}(IP\text{-}10/18S)+1.6464 \log_{10}(18S)$$

where:
   CD3ε is an absolute urinary CD3ε mRNA copy number per microgram of total RNA in the urine sample;
   IP-10 is an absolute urinary IP-10 mRNA copy number per microgram of total RNA in the urine sample; and
   18S is an absolute urinary 18S rRNA copy number per microgram of total RNA in the urine sample times $10^{-6}$;

to thereby detect and treat a developing or existing dysfunction or rejection of a kidney transplant in the subject.

2. The method of claim 1, comprising hybridizing the at least one probe or primer to RNA from the urine sample, wherein the at least one probe or primer can hybridize to a CD3ε mRNA, IP-10 mRNA, or 18S rRNA.

3. The method of claim 1, comprising hybridizing the at least one probe or primer to RNA from the urine sample, wherein at least one probe or primer can hybridize to an nucleic acid sequence that has at least 70% sequence identity or complementarity to SEQ ID NO:1, SEQ ID NO:2, or SEQ ID NO:3.

4. The method of claim 1, comprising normalizing the amount or copy number of CD3ε mRNA or IP-10 mRNA in the sample against the amount or copy number of 18S rRNA in the sample.

5. The method of claim 1, wherein the subject has an existing dysfunction or rejection of a kidney transplant when the signature is greater than −1.21.

6. The method of claim 1, wherein the subject will develop dysfunction or rejection of a kidney transplant when the signature is greater than −1.21.

7. The method of claim 1, comprising monitoring a subject over time for developing or existing dysfunction or rejection of a kidney transplant in a subject.

8. The method of claim 1, comprising monitoring a subject over time and informing the subject if there is continuing rise in the value of the diagnostic signature over time.

9. The method of claim 1, comprising informing the subject of a developing or existing dysfunction or rejection of a kidney transplant in the subject.

10. The method of claim 1, comprising informing the subject of a developing or existing dysfunction or rejection of a kidney transplant in the subject when the signature is greater than −1.21.

11. The method of claim 1, comprising treating a developing or existing dysfunction or rejection of a kidney transplant in the subject.

12. The method of claim 1, comprising treating a developing or existing dysfunction or rejection of a kidney transplant in the subject, wherein treating comprises plasmapheresis, administration of an anti-rejection agent, increasing a dosage of an anti-rejection agent that the subject is receiving or any combination thereof.

13. A composition consisting essentially of at least one probe or primer with a SEQ ID NO: 4, 5, 6, 13, 14, 15, 28, 29, or 30 sequence for each of CD3ε mRNA, IP-10 mRNA, and 18S rRNA; and an optional control or reference probe or primer.

14. A device consisting essentially of at least one probe or primer with a SEQ ID NO: 4, 5, 6, 13, 14, 15, 28, 29, or 30 sequence for each of CD3ε mRNA, IP-10 mRNA, and 18S rRNA covalently linked to a solid support, and an optional control or reference probe or primer covalently linked to a solid support.

15. A kit consisting essentially of at least one probe or primer with a SEQ ID NO: 4, 5, 6, 13, 14, 15, 28, 29, or 30 sequence for each of CD3ε mRNA, IP-10 mRNA, and 18S rRNA, and instructions for use in detecting potential or existing dysfunction or rejection of a kidney transplant in a subject.

16. The kit of claim 15, comprising a filter to collect cells from a urine sample.

17. The method of claim 1, wherein determining absolute urinary CDR mRNA, IP-10 mRNA, and 18S rRNA copy numbers per microgram of total RNA in the urine RNA sample comprises measurement of CD3ε mRNA, mRNA, and 18S rRNA by nucleic acid amplification and determination of CD3ε mRNA, IP-10 mRNA, and 18S rRNA copy numbers per microgram of total RNA with a standard curve.

* * * * *

UNITED STATES PATENT AND TRADEMARK OFFICE
CERTIFICATE OF CORRECTION

PATENT NO. : 9,758,828 B2
APPLICATION NO. : 14/170132
DATED : September 12, 2017
INVENTOR(S) : Suthanthiran et al.

It is certified that error appears in the above-identified patent and that said Letters Patent is hereby corrected as shown below:

On the Title Page

On page 2, in Column 1, item (56), under "Other Publications", Line 41, delete "Receipients"," and insert --Recipients",-- therefor In the Claims In Column 83, Line 4, in Claim 17, delete "CDR" and insert --CD3ε-- therefor In Column 83, Line 6, in Claim 17, delete "mRNA," and insert --IP-10 mRNA,-- therefor Signed and Sealed this
Thirty-first Day of July, 2018

Andrei Iancu
*Director of the United States Patent and Trademark Office*